United States Patent
Cooks et al.

(10) Patent No.: US 9,546,979 B2
(45) Date of Patent: Jan. 17, 2017

(54) ANALYZING A METABOLITE LEVEL IN A TISSUE SAMPLE USING DESI

(71) Applicant: Purdue Research Foundation, West Lafayette, IN (US)

(72) Inventors: Robert Graham Cooks, West Lafayette, IN (US); Kevin Scott Kerian, Lafayette, IN (US); Alan Keith Jarmusch, Lafayette, IN (US); Ahmed Mohamed Hamid, West Lafayette, IN (US); Livia Schiavinato Eberlin, Lafayette, IN (US)

(73) Assignee: PURDUE RESEARCH FOUNDATION, West Lafayette, IN (US)

(*) Notice: Subject to any disclaimer, the term of this patent is extended or adjusted under 35 U.S.C. 154(b) by 438 days.

(21) Appl. No.: 13/909,619

(22) Filed: Jun. 4, 2013

(65) Prior Publication Data
US 2013/0273560 A1    Oct. 17, 2013

Related U.S. Application Data

(63) Continuation-in-part of application No. 13/475,305, filed on May 18, 2012, now Pat. No. 9,157,921.
(Continued)

(51) Int. Cl.
G01N 24/00    (2006.01)
G01N 27/62    (2006.01)
(Continued)

(52) U.S. Cl.
CPC .............. *G01N 27/62* (2013.01); *G01N 33/50* (2013.01); *G01N 2560/00* (2013.01);
(Continued)

(58) Field of Classification Search
CPC .. H01J 49/0004; H01J 49/164; H01J 49/0418; H01J 49/40; H01J 49/04; H01J 49/0027; H01J 49/165; H01J 49/0463; H01J 49/142; H01J 49/16; H01J 49/0059; H01J 49/161; H01J 49/00; H01J 49/004
See application file for complete search history.

(56) References Cited

U.S. PATENT DOCUMENTS 5,756,994 A * 5/1998 Bajic ................... H01J 49/0445
                                                           250/288
7,335,897 B2    2/2008 Takats et al.
2012/0119079 A1 5/2012 Ouyang et al.

FOREIGN PATENT DOCUMENTS

WO    2009/102766 A1    8/2009
WO    2010/127059 A1    11/2010

OTHER PUBLICATIONS

Dettmer et al., "MAss Spectrometry-Based Metabolomics". Mass Spectrom. Rev., 2007, v. 26, No. 1, pp. 51-78.*
(Continued)

*Primary Examiner* — Yelena G Gakh
(74) *Attorney, Agent, or Firm* — Brown Rudnick LLP; Adam M. Schoen

(57) ABSTRACT

The invention generally relates to methods for analyzing a metabolite level in a sample. In certain embodiments, methods of the invention may involve obtaining a sample, analyzing the sample using a mass spectrometry technique to determine a level of at least one metabolite in the sample, and correlating the metabolite level with an originating source of the sample, thereby analyzing the sample.

16 Claims, 41 Drawing Sheets

Related U.S. Application Data

(60) Provisional application No. 61/487,363, filed on May 18, 2011, provisional application No. 61/791,100, filed on Mar. 15, 2013, provisional application No. 61/778,292, filed on Mar. 12, 2013.

(51) Int. Cl.
*G01N 33/50* (2006.01)
*H01J 49/00* (2006.01)
*H01J 49/14* (2006.01)

(52) U.S. Cl.
CPC .. *G01N 2800/7028* (2013.01); *H01J 49/0004* (2013.01); *H01J 49/142* (2013.01)

(56) References Cited

OTHER PUBLICATIONS

Zettersten et al., "Recessive x-linked ichthyosis: role of cholesterol-sulfate accumulation in the barrier abnorrmnality", J. Invest. Dermatol., Nov. 1998, v. 111, No. 5, pp. 784-790, Abstract.*
Wiseman et al. "Ambient molecular imaging by desorption electrospray ionization mass spectrometry", Nature Protocols, 2008, vol. 3, No. 3, pp. 517-524.*
Chaurand et al. "Assessing Protein Patterns in Disease Using Imaging Mass Spectrometry", J. Proteome Res., 2004, v. 3, pp. 245-252.*
Yoshimara et al., "Real-time analysis of living animals by electrospray ionization mass spectrometry", Anal. Biochem., Jun. 2011, v. 417, pp. 195-201.*
Dessi et al., "Cholesterol Content in Tumor Tissues is Inversely Associated with High-Density Lipoprotein Cholesterol in Serum in Patients with Gastrointestinal Cancer", Cancer, Jan. 15, 1994, vf. 73, No. 2, pp. 253-258.*
Parsons, D.W., et al. An integrated genomic analysis of human glioblastoma multiforme. Science 321, 1807-1812 (2008).
Pope, W.B., et al. Non-invasive detection of 2-hydroxyglutarate and other metabolites in IDH1 mutant glioma patients using magnetic resonance spectroscopy. J Neurooncol 107, 197-205 (2012).
Rohle, D., et al. An Inhibitor of Mutant IDH1 Delays Growth and Promotes Differentiation of Glioma Cells. Science (2013).
Takats, Z., Wiseman, J.M., Gologan, B. & Cooks, R.G. Mass spectrometry sampling under ambient conditions with desorption electrospray ionization. Science 306, 471-473 (2004).
Turcan, S., et al. IDH1 mutation is sufficient to establish the glioma hypermethylator phenotype. Nature 483, 479-483 (2012).
Van Berkel, G.J., Pasilis, S.P. & Ovchinnikova, O. Established and emerging atmospheric pressure surface sampling/ionization techniques for mass spectrometry. J Mass Spectrom 43, 1161-1180 (2008).
Wang, F., et al. Targeted Inhibition of Mutant IDH2 in Leukemia Cells Induces Cellular Differentiation. Science (2013).
Weller, M., Wick, W. & von Deimling, A. Isocitrate dehydrogenase mutations: a challenge to traditional views on the genesis and malignant progression of gliomas. Glia 59, 1200-1204 (2011).
Wiseman, J.M., et al. Desorption electrospray ionization mass spectrometry: Imaging drugs and metabolites in tissues. Proc Natl Acad Sci U S A 105, 18120-18125 (2008).
Wiseman, J.M., Ifa, D.R., Venter, A. & Cooks, R.G. Ambient molecular imaging by desorption electrospray ionization mass spectrometry. Nat Protoc 3, 517-524 (2008).
Xu, W., et al. Oncometabolite 2-hydroxyglutarate is a competitive inhibitor of alpha- ketoglutarate-dependent dioxygenases. Cancer Cell 19, 17-30 (2011).
Yan, H., et al. IDH1 and IDH2 mutations in gliomas. N Engl J Med 360, 765-773 (2009).
Otsuka, Y. et al., Scanning probe electrospray ionization for ambient mass spectrometry, Rapid Commun Mass Spectrom. Dec. 15, 2012;26(23):2725-32. doi: 10.1002/rcm.6399.
Agar, N.Y., et al. Development of stereotactic mass spectrometry for brain tumor surgery. Neurosurgery 68, 280-289; discussion 290 (2011).
Amary, M.F., et al. IDH1 and IDH2 mutations are frequent events in central chondrosarcoma and central and periosteal chondromas but not in other mesenchymal tumours. J Pathol 224, 334-343 (2011).
Andronesi, O.C., et al. Detection of 2-hydroxyglutarate in IDH-mutated glioma patients by in vivo spectral-editing and 2D correlation magnetic resonance spectroscopy. Sci Transl Med 4, 116ra114 (2012).
Borger, D.R., et al. Frequent mutation of isocitrate dehydrogenase (IDH)1 and IDH2 in cholangiocarcinoma identified through broad-based tumor genotyping. Oncologist 17, 72-79 (2012).
Capper, D., et al. Characterization of R132H mutation-specific IDH1 antibody binding in brain tumors. Brain Pathol 20, 245-254 (2010).
Chi, A.S., et al. Prospective, high-throughput molecular profiling of human gliomas. J Neurooncol 110, 89-98 (2012).
Choi, C., et al. 2-hydroxyglutarate detection by magnetic resonance spectroscopy in IDH-mutated patients with gliomas. Nat Med 18, 624-629 (2012).
Dang, L., et al. Cancer-associated IDH1 mutations produce 2-hydroxyglutarate. Nature 462, 739-744 (2009).
Dias-Santagata, D., et al. BRAF V600E mutations are common in pleomorphic xanthoastrocytoma: diagnostic and therapeutic implications. PLoS One 6, e17948 (2011).
Dias-Santagata, D., et al. Rapid targeted mutational analysis of human tumours: a clinical platform to guide personalized cancer medicine. EMBO Mol Med 2, 146-158 (2010).
Dill, A.L., et al. Lipid profiles of canine invasive transitional cell carcinoma of the urinary bladder and adjacent normal tissue by desorption electrospray ionization imaging mass spectrometry. Anal Chem 81, 8758-8764 (2009).
Eberlin, L.S., et al. Ambient mass spectrometry for the intraoperative molecular diagnosis of human brain tumors. Proc Natl Acad Sci U S A (2013).
Eberlin, L.S., et al. Classifying human brain tumors by lipid imaging with mass spectrometry. Cancer Res 72, 645-654 (2012).
Eberlin, L.S., et al., Discrimination of human astrocytoma subtypes by lipid analysis using desorption electrospray ionization imaging mass spectrometry. Angew Chem Int Ed Engl 49, 5953-5956 (2010).
Eberlin, L.S., et al. Nondestructive, histologically compatible tissue imaging by desorption electrospray ionization mass spectrometry. Chembiochem 12, 2129-2132 (2011).
Elhawary, H., et al. Intraoperative real-time querying of white matter tracts during frameless stereotactic neuronavigation. Neurosurgery 68, 506-516; discussion 516 (2011).
Elkhaled, A., et al. Magnetic resonance of 2-hydroxyglutarate in IDH1-mutated low-grade gliomas. Sci Transl Med 4, 116ra115 (2012).
Guo, J., et al. The relationship between Cho/NAA and glioma metabolism: implementation for margin delineation of cerebral gliomas. Acta Neurochir (Wien) 154, 1361-1370; discussion 1370 (2012).
Harris, G.A., Galhena, A.S. & Fernandez, F.M. Ambient sampling/ionization mass spectrometry: applications and current trends. Anal Chem 83, 4508-4538 (2011).
Hartmann, C., et al. Type and frequency of IDH1 and IDH2 mutations are related to astrocytic and oligodendroglial differentiation and age: a study of 1,010 diffuse gliomas. Acta Neuropathol 118, 469-474 (2009).
Ifa, D.R., Wu, C., Ouyang, Z. & Cooks, R.G. Desorption electrospray ionization and other ambient ionization methods: current progress and preview. Analyst 135, 669-681 (2010).
Jolesz, F.A. Intraoperative imaging in neurosurgery: where will the future take us? Acta Neurochir Suppl 109, 21-25 (2011).
Kalinina, J., et al. Detection of "oncometabolite" 2-hydroxyglutarate by magnetic resonance analysis as a biomarker of IDH1/2 mutations in glioma. J Mol Med (Berl) 90, 1161-1171 (2012).

(56) References Cited

OTHER PUBLICATIONS

Koivunen, P., et al. Transformation by the (R)-enantiomer of 2-hydroxyglutarate linked to EGLN activation. Nature 483, 484-488 (2012).

Lai, A., et al. Evidence for sequenced molecular evolution of IDH1 mutant glioblastoma from a distinct cell of origin. J Clin Oncol 29, 4482-4490 (2011).

Lazovic, J., et al. Detection of 2-hydroxyglutaric acid in vivo by proton magnetic resonance spectroscopy in U87 glioma cells overexpressing isocitrate dehydrogenase-1 mutation. Neuro Oncol 14, 1465-1472 (2012).

Linehan, W.M., Srinivasan, R. & Schmidt, L.S. The genetic basis of kidney cancer: a metabolic disease. Nat Rev Urol 7, 277-285 (2010).

Losman, J.A., et al. (R)-2-Hydroxyglutarate is Sufficient to Promote Leukemogenesis and Its Effects Are Reversible. Science (2013).

Lu, C., et al. IDH mutation impairs histone demethylation and results in a block to cell differentiation. Nature 483, 474-478 (2012).

Mardis, E.R., et al. Recurring mutations found by sequencing an acute myeloid leukemia genome. n. Engl J Med 361, 1058-1066 (2009).

Nemes, P. & Vertes, A. Ambient mass spectrometry for in vivo local analysis and in situ molecular tissue imaging. TrAC—Trends in Analytical Chemistry 34, 22-33 (2012).

Abe et al., Inkjet-Printed Microfluidic Multianalyte Chemical Sensing Paper, Anal. Chem. 2008, 80, 6928-6934, published in USA.

Bruzewicz et al., Low-Cost Printing of Poly(dimethylsiloxane) Barriers to Define Microchannels in Paper, (Anal. Chem. 2008, 80, 3387-3392), published in USA.

Carroll et al., 1975, Atmospheric Pressure Ionization Mass Spectrometry: Corona Discharge Ion Source for Use in Liquid Chromatograph-Mass Spectrometer-Computer Analytical System, Anal. Chem. 47:2369-2373, published in USA.

Cody et al., 2005, Versatile New Ion Source for the Analysis of Materials in Open Air under Ambient Condition, Anal. Chem. 77:2297-2302.

Cooks et al., (2011), New ionization methods and miniature mass spectrometers for biomedicine: DESI imaging for cancer diagnostics and paper spray ionization for therapeutic drug monitoring, Faraday Discussions 149:247-267, published in United Kingdom.

Dill, A.L., et al., Multivariate statistical differentiation of renal cell carcinomas based on lipidomic analysis by ambient ionization imaging mass spectrometry, Analytical and Bioanalytical Chemistry 398, 2969-2978 (2010), published in Germany.

Dill, A.L., et al., Multivariate Statistical Identification of Human Bladder Carcinomas Using Ambient Ionization Imaging Mass Spectrometry, A European Journal 17, 2897-2902 (2011), published in Germany.

Eberlin, L.S. et al., Cholesterol Sulfate Imaging in Human Prostate Cancer Tissue by Desorption Electrospray Ionization Mass Spectrometry, Analytical Chemistry 82, 3430-3434 (2010), published in USA.

Ellis et al., Imaging of Human Lens Lipids by Desorption Electrospray Ionization Mass Spectrometry, J. Am. Soc. Mass Spectrom. 21(12):2095-2104, published in USA.

Fenn et al., 1989, Electrospray Ionization for Mass Spectrometry of Large Biomolecules, Science 246:64-71, published in USA.

Ifa et al., Latent Fingerprint Chemical Imaging by Mass Spectrometry, Int. J. Mass Spectrom. 259(8):805, 2007, published in USA.

Kogelschatz, Dielectric-barrier Discharges: Their History, Discharge Physics, and Industrial Applications, Plasma Chemistry and Plasma Processing, 23:1-46, 2003, published in Germany.

Laiko et al., Atmospheric Pressure Matrix-Assisted Laser Desoprtion/Ionization Mass Spectrometry, Analytical Chemistry, 72:652-657, 2000, published in USA.

Li et al., Paper-Based Microfluidic Devices by Plasma Treatment, (Anal. Chem. 2008, 80, 9131-9134), published in USA.

Manicke NE, et al., 2009, Imaging of Lipids in Atheroma by Desorption Electrospray Ionization Mass Spectrometry, Analytical Chemistry 81(21):8702-8707, published in USA.

Martinez et al., Flash: A rapid method for prototyping paper-based microfluidic devices†‡, Lab Chip 2008, 8, 2146-2150, published in United Kingdom.

Martinez et al., Patterned Paper as a Platform for Inexpensive, Low-Volume, Portable Bioassays**, (Angew. Chem. Int. Ed. 2007, 46, 1318-1320), published in Germany.

Martinez et al., Three-dimensional microfluidic devices fabricated in layered paper and tape, (Proc. Natl Acad. Sci. USA 2008, 105, 19606-19611), published in USA.

Schwamborn K, et al., (2007), Identifying prostate carcinoma by MALDI-Imaging, International Journal of Molecular Medicine 20(2):155-159, published in Germany.

Shiea et al., Electrospray-assisted laser desorption/ionization mass spectrometry for direct ambient analysis of solids, J. Rapid Communications in Mass Spectrometry, 19:3701-3704, 2005, published in USA.

Tanaka et al., Protein and Plymer Analyses up to m/z 100 000 by Laser Ionization Time-of-Flight Mass Spectrometry, Rapid Commun. Mass Spectrom., 2:151-153,1988, published in United Kingdom.

Yamashita et al., Electrospray Ion Source. Another Variation on the Free-Jet Theme, J. Phys. Chem., 88:4451-4459, 1984, published in USA.

\* cited by examiner

PS 18:0 / 22:6

ST (24:1)

ST (24:0)

PI 18:0/20:4

FA (20:4)

H&E stained

FIG. 4G
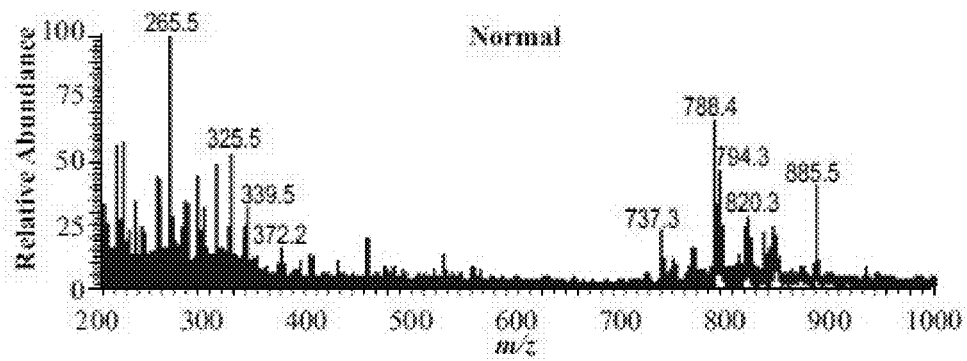
FIG. 4H
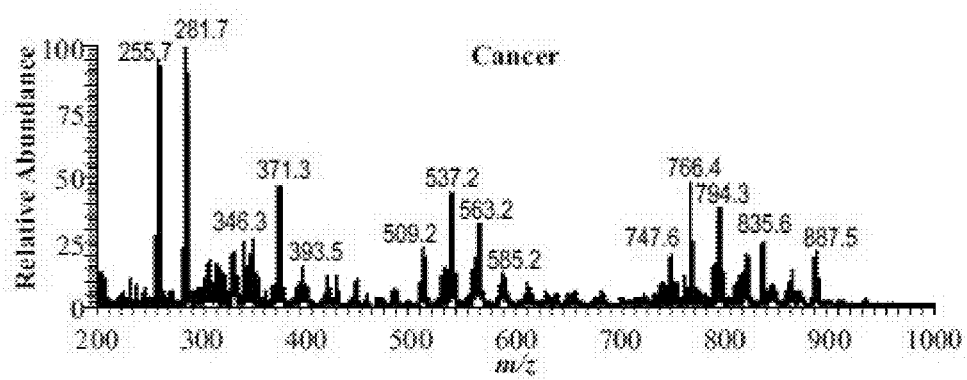
FIG. 4I     Overlaid
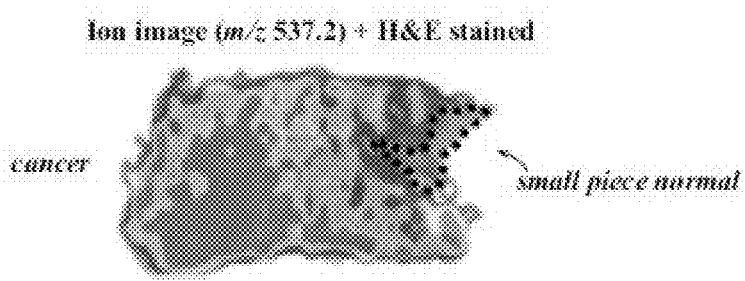

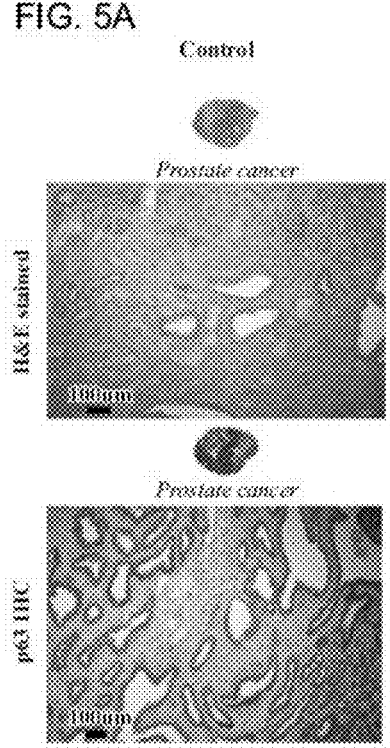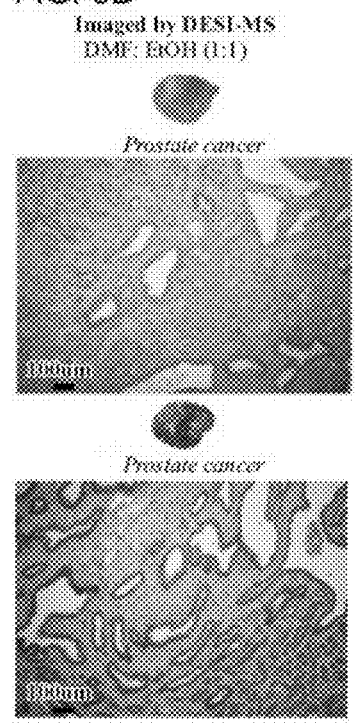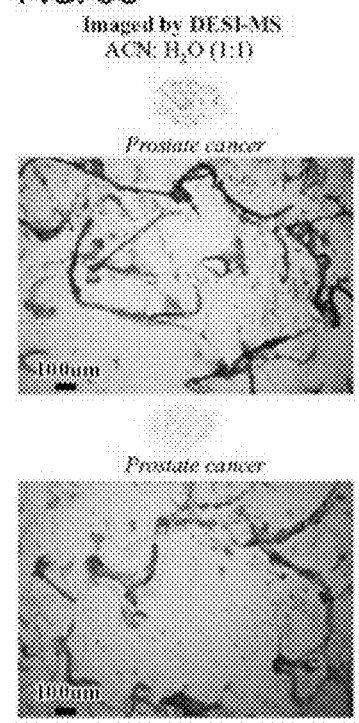
FIG. 5A Control
FIG. 5B Imaged by DESI-MS DMF: EtOH (1:1)
FIG. 5C Imaged by DESI-MS ACN: H₂O (1:1)

FIG. 22

ANALYZING A METABOLITE LEVEL IN A TISSUE SAMPLE USING DESI

RELATED APPLICATIONS

The present application is a continuation-in-part of U.S. nonprovisional application Ser. No. 13/475,305, filed May 18, 2012, which claims the benefit of and priority to U.S. provisional application Ser. No. 61/487,363, filed May 18, 2011. The present application also claims the benefit of and priority to U.S. provisional application Ser. No. 61/791,100, filed Mar. 15, 2013. The present application also claims the benefit of and priority to U.S. provisional application Ser. No. 61/778,292, filed Mar. 12, 2013. The content of each application is incorporated by reference herein in its entirety.

GOVERNMENT SUPPORT

This invention was made with government support under EB009459; awarded by the National Institutes of Health. The government has certain rights in the invention.

FIELD OF THE INVENTION

The invention generally relates to methods for analyzing a metabolite level in a sample.

BACKGROUND

Biological systems are increasingly viewed and analyzed as highly complex networks of interlinked macromolecules and metabolites. Metabolites are low molecular weight compounds (<1 kDa) involved in chemical reactions that occur inside cells of living organisms to uphold life, i.e. the process of metabolism. The chemical diversity of the metabolome, defined as the complement of all detectable metabolites, is large and includes a wide range of compound classes, e.g. carbohydrates, amino acids, organic acids, and sterols. The quantity and number of metabolites vary with changing conditions such as environment, diet and in response to disease. Significant time and money has been invested in order to investigate the relationship between metabolite alterations and biochemical mechanisms, including disease processes.

Methods for analysis of the metabolome include nuclear magnetic resonance (NMR) spectroscopy, gas chromatography (GC) and liquid chromatography (LC) coupled to mass spectrometry (MS). In addition, Fourier transform InfraRed spectroscopy (FTIR) has been used together with direct infusion mass spectrometry to analyze metabolites.

NMR and FTIR require minimal sample preparation, however, detection limits are higher compared to the MS-based techniques and elucidation of spectra composed of many metabolites can be problematic. A problem with MS-based methods is that they require complex sample preparation protocols that involve sample extraction, purification, and other work-up steps prior to sample analysis. Those preparation protocols in addition to the solvents used as part of the MS analysis destroy the native morphology of the sample, making it impossible to correlate diagnostic results with their originating source.

SUMMARY

The invention generally relates to methods for analyzing a metabolite level in a sample. Aspects of the invention are accomplished using mass spectrometry techniques that are non-destructive of native tissue morphology. In that manner, a sample is analyzed by mass spectrometry to obtain a metabolite level in the sample, and because the analyzed sample remains intact, the metabolite level can be correlated with its originating source. Methods of the invention are useful for rapidly identifying abnormal tissue, such as cancerous tissue, and distinguishing abnormal tissue from normal tissue, which is important for indicating tumor margins.

Methods of the invention allow for analysis of any type of sample that includes metabolites, for example, human or animal tissue or plant tissue. In certain embodiments, the sample is human tissue. In those embodiments, methods of the invention may be performed on the tissue to obtain a molecular diagnosis and then the same tissue section can be used not only for H&E staining, but also for immunohistochemistry. Those advancements allow methods of the invention to be included in the tissue analysis clinical workflow. They also allow more detailed diagnostic information to be obtained by combining two orthogonal techniques, MS and histological examination.

There are numerous approaches that can be employed to conduct a mass spectral analysis of a sample without destroying the native morphology of the sample. In one embodiment, a mass spectrometry analysis technique utilizes a liquid phase that does not destroy native tissue morphology during analysis. Exemplary liquid phases include DMF, ACN, or THF. In certain embodiments, the DMF, ACN, or THF may be combined with at least one other component, such as EtOH, $H_2O$, or a combination thereof. Exemplary combinations include ACN:EtOH, MeOH:$CHCl_3$ or ACN:$CHCl_3$.

In such embodiments, any mass spectrometry technique known in the art may be used with methods of the invention. Exemplary mass spectrometry techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom., 2:151-153, 1988). The content of each of these references in incorporated by reference herein its entirety.

Exemplary mass spectrometry techniques that utilize direct ambient ionization/sampling methods include desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desoption/ionization (ELDI; Shiea et al., J. Rapid Communications in Mass Spectrometry, 19:3701-3704, 2005). The content of each of these references is incorporated by reference herein its entirety.

In certain embodiments, the mass spectrometry technique is desorption electrospray ionization (DESI). DESI is an ambient ionization method that allows the direct ionization of species from thin tissue sections (Takats et al., Science, 306:471-473, 2004 and Takats, U.S. Pat. No. 7,335,897). DESI-MS imaging has been successfully used to diagnose multiple types of human cancers based on their lipid profiles detected directly from tissue (Eberlin L S, Ferreira C R, Dill A L, Ifa D R, & Cooks R G (2011) Desorption Electrospray Ionization Mass Spectrometry for Lipid Characterization and Biological Tissue Imaging. Biochimica Et Biophysica Acta-Molecular And Cell Biology Of Lipids accepted).

In certain embodiments, DESI is operated in the imaging mode. Operated in an imaging mode, it uses a standard microprobe imaging procedure, which in this case involves moving the probe spray continuously across the surface while recording mass spectra. See for example, Wiseman et al. Nat. Protoc., 3:517, 2008, the content of which is incorporated by reference herein its entirety. Each pixel yields a mass spectrum, which can then be compiled to create an image showing the spatial distribution of a particular compound or compounds. Such an image allows one to visualize the differences in the distribution of particular compounds over the sample (e.g., a tissue section). If independent information on biological properties of the sample are available, then the MS spatial distribution can provide chemical correlations with biological function or morphology. Moreover, the combination of the information from mass spectrometry and histochemical imaging can be used to improve the quality of diagnosis.

In particular embodiments, the DESI ion source is a source configured as described in Ifa et al. (Int. J. Mass Spectrom. 259(8), 2007). A software program allows the conversion of the XCalibur 2.0 mass spectra files (.raw) into a format compatible with the Biomap software (freeware, http://www.maldo-msi.org). Spatially accurate images are assembled using the Biomap software.

Another approach used by methods of the invention utilizes a mass spectrometry technique that involves contacting a probe to an in situ sample such that a portion of the sample is retained on the probe once the probe has been removed from the sample, and applying solvent and a high voltage to the probe, thereby generating ions of an analyte from the portion of the sample on the probe. Such a technique allows one to obtain diagnostic information without the removal of the sample. Since the sample remains in situ, it is possible to correlate the results to the originating source.

Another approach used by methods of the invention utilizes a mass spectrometry technique that involves contacting a porous probe to an in situ sample such that a portion of the sample is retained on the porous probe once the probe has been removed from the sample, and applying solvent and a high voltage to the probe, thereby generating ions of an analyte from the portion of the sample on the probe. Such a technique allows one to obtain diagnostic information without the removal of the sample. Since the sample remains in situ, it is possible to correlate the results to the originating source.

Another aspect of the invention provides methods for identifying abnormal tissue. Those methods involve analyzing tissue using a mass spectrometry technique to determine a level of at least one metabolite in the tissue, correlating the metabolite level with an originating source of the tissue, and identifying the abnormal tissue.

BRIEF DESCRIPTION OF THE DRAWINGS

FIG. 4G shows a representative mass spectra of normal tissue. FIG. 4H shows a representative mass spectra of cancerous tissue. FIG. 4I shows an overlay of the ion image m/z 537.2 and H&E stain of the same tissue section allowed a region of normal tissue to be detected within the cancerous tissue section.

FIGS. 5A-5C show that non-destructive DESI-MS imaging allows immunohistochemistry to be performed after imaging on the same tissue section when using morphologically friendly solvent systems. Optical images of the entire tissue and magnified brightfield optical images of H&E stained and p63 immunohisto-chemistry( ) (IHC) prostate tissue sections used are shown for control samples (FIG. 5A), samples imaged by DESI-MS using DMF:EtOH (1:1) as solvent system (FIG. 5B), and samples imaged by DESI-MS using standard ACN:$H_2O$ (1:1) as solvent system (FIG. 5C).

FIG. 22 shows a workflow for analyzing bacteria using Touch Spray.

FIG. 31 panel B shows that tandem mass spectrum of a low abundance ion detected at m/z 147 from sample G31 presents a fragmentation pattern that does not match that of standard 2-HG. FIG. 31 panel C shows negative ion mode DESI mass spectrum from m/z 100 to 1000 of sample G23, an oligodendroglioma with the IDH1 R132H mutant shows high abundance of an ion at m/z 147.2. FIG. 31 panel D shows that tandem mass spectrum of m/z 147.2 detected from sample G23 presents a fragmentation pattern that exactly matches that of standard 2-HG.

FIG. 32 panel B shows negative ion mode DESI mass spectra obtained in a LTQ Orbitrap mass spectrometer from m/z 100 to 1000 for sample G29, a glioblastoma with wild-type IDH1. Insets show zoom in region m/z 146.90-147.16. Tandem MS of the 2-HG standard at m/z 147.02982 using high resolution MS confirmed the main fragment at m/z 129.01953 which corresponds to neutral loss of water ($C_5H_5O_4$, 1.7 ppm mass error), and (spectrum not shown) MS3 fragments m/z 101.02455 ($C_4H_5O_3$, 1.32 ppm mass error) and m/z 85.02966 ($C_4H_5O_2$, 1.88 ppm mass error) that correspond to further neutral losses of CO and CO2 from m/z 129, respectively.

FIG. 35 panel A shows immunohistochemistry using an IDH1 R132H point mutation specific antibody on FFPE sections from glioma samples (G33 and G28), (scale bar, 100 µm). FIG. 35 panel B shows negative ion mode DESI mass spectra obtained using a linear ion trap mass spectrometer for samples G33 and G28 that are negative for IDH1 R132H mutant immunohistochemistry. FIG. 35 panel C shows targeted mutational profiling using SNaPshot analysis on nucleic acids extracted from GBM archival specimens (G33 and G28) run in parallel with a normal genomic DNA control, as indicated. The arrows point to the IDH2 R132G (c.394C>G) mutant allele identified in both tumor samples. The assayed loci were as follows: (1) KRAS 35; (2) EGFR 2236_50del R; (3) PTEN 517; (4) TP53 733; (5) IDH1 394; (6) PIK3CA 3139; (7) NOTCH1 4724 and (8) NOTCH1 4802.

FIG. 36 panel A shows negative ion mode two dimensional DESI MS images of human glioblastoma cell line (BT329) that has wild-type IDH1 and FIG. 36 panel B shows human glioblastoma cell line (BT116) that has an IDH1 R132H mutation that have been xenografted into the brains of immunocompromised mice. The left panel is an ion map demonstrating the relative signal intensity of peak m/z 146.9, which was confirmed to be 2-HG by tandem MS analysis (MS2 and MS3). Relative signal intensity (0-100%) is plotted for each specimen using a color scale. Low magnification and high magnification light microscopy images of HE stained sections are shown (scale bar, 100 µm).

FIG. 38 panel A shows that normalized 2-HG signal is represented with a warm color scale as indicated by the scale bar; set from the lowest (yellow) to highest (red) levels detected from this individual case. Mass spectrometry data was acquired using a DESI LTQ instrument. Stereotactic positions were digitally registered to the pre-operative MRI using neuronavigation (BrainLab system). The inset shows the segmented tumor in green as it relates to brain anatomy. FIG. 38 panel B shows histopathology scoring of tumor cell concentrations determined from reviewing of HE stained tissue sections corresponding to samples analyzed by mass spectrometry. The scale is divided into four discrete binned colors corresponding to normal brain, low (1-29%), medium (30-59%), and high (60-100%) tumor cell concentrations. FIG. 38 panel C shows high magnification microscopy images of HE stained sections of sample D3 representing high tumor cell concentration. The image from the first panel is from the MS-analyzed frozen section, the middle panel is from the corresponding formalin fixed tissue section, and the last panel is from immunohistochemistry for IDH1 R132H mutant (fixed tissue). FIG. 38 panel D shows high magnification microscopy images of HE stained sections of sample D10 representing infiltrating tumor cells. The image from the first panel is from the MS-analyzed frozen section, the middle panel is from the corresponding formalin fixed tissue section, and the last panel is from immunohistochemistry for IDH1 R132H mutant (fixed tissue) (scale bar, 100 µm).

FIG. 39 panel A shows that normalized 2-HG signal is represented with a warm color scale as indicated by the scale bar; set from the lowest to highest levels detected from this individual case. Mass spectrometry data was acquired on an DESI Amazon Speed instrument. Stereotactic positions were digitally registered to the pre-operative MRI using neuronavigation (BrainLab system). FIG. 39 panel B shows high magnification microscopy images of an HE stained section of formalin fixed paraffin embedded tissue from sample S56 showing high tumor cell concentration (upper panel), and of immunohistochemistry for IDH1 R132H mutant (lower panel). FIG. 39 panel C shows 2-HG over tumor volume reconstruction from the T2 weighted intraoperative MRI. Inset shows the residual lesion. FIG. 39 panel D shows high magnification microscopy images of HE stained sections of formalin fixed paraffin embedded tissue from sample S60 showing the presence of residual tumor cells (upper panel), and of immunohistochemistry for IDH1 R132H mutant (lower panel) (scale bar, 100 µm).

DETAILED DESCRIPTION

Figure 1A:
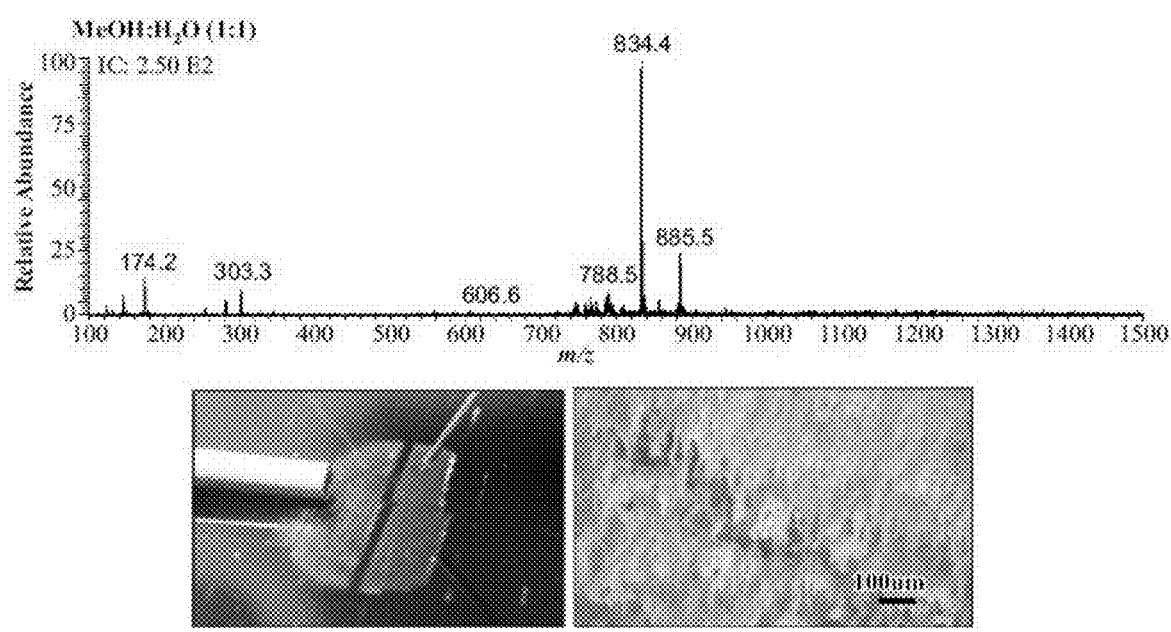
FIG. 1A shows the chemical information and physical effect of standard DESI-MS solvent system MeOH:$H_2O$ (1:1) on sequential 15 μm thick mouse brain tissue sections.

The invention generally relates to methods for analyzing a metabolite level in a sample. In certain embodiments, methods of the invention involve obtaining a sample, analyzing the sample using a mass spectrometry technique to determine a level of at least one metabolite in the sample, and correlating the metabolite level with an originating source of the sample, thereby analyzing the sample.

A metabolite generally refers to any compound that is an intermediate or product of metabolism or a compound that is necessary for or taking part in a particular metabolic process. A metabolite is not limited to any particular class of compounds, and includes, for example, classes of compounds such as lipids, carbohydrates, amino acids, organic acids and sterols. A metabolite may be a primary metabolite (i.e., a compound that is directly involved in normal growth, development, and reproduction) or a secondary metabolite (i.e., a compound that is not directly involved in those processes, but usually has an important ecological function). In an exemplary embodiment, a metabolite may be a low molecular weight compounds (<1 kDa) that is the product of a chemical reaction or reactions that occur inside cells of living organisms, such as within human or animal or plant tissue. Living organisms also encompasses microorganisms, such as bacteria and fungus. In certain embodiments, a metabolite is an intermediate or a product of an enzymatic reaction, such as an enzymatic reaction that occurs within the cells of normal tissue or abnormal tissue, such as diseased tissue, such as cancerous tissue. Considerations related to metabolites are described, for example, in Harris et al., (Biochemical Facts behind the Definition and Properties of Metabolites, found at the website for the FDA on the page related to metabolites), the content of which is incorporated by reference herein in its entirety.

Abnormal metabolite levels may be associated with a disease state, for example metabolic diseases, cardiovascular diseases, kidney diseases, liver diseases, gastrointestinal diseases, cancers, etc. In certain embodiments, the metabolites analyzed result from genetic aberrations that constitute particular disease states, including cancer, including endogenous compounds whose constitutive levels vary and de novo compounds (Dill, et al., A European Journal 17, 2897-2902 (2011); Dill et al., Analytical and bioanalytical chemistry 398, 2969-2978 (2010); Eberlin et al. Analytical chemistry 82, 3430-3434 (2010); and Eberlin et al. Proceedings of the National Academy of Sciences (2013)). Metabolites of interest are of diagnostic and/or prognostic value.

Metabolites may include those derived from the pathways associated with energy production, cellular signaling, and structure. Such metabolites include aerobic and anaerobic cellular respiration and synthesis of lipid constituents. The compounds from the alpha-hydroxy acid (AHA) class are implicated. The production of alpha-hydroxyglutaric acid (2-HG) in human brain tumors is particularly included. Mutations in isocitrate dehydrogenases (IDHs) deviates prototypical conversion of isocitrate to alpha-ketogluterate via oxidative decarboxylation. Additionally, beta and gamma hydroxy acids are implicated. Metabolites of interest in neural cancers include small amino acid neurotransmitters (e.g. aspartate, glutamate, GABA, glycine, etc), neuropeptides, opioids (e.g. endorphin), monoamines (e.g. dopamine and serotonin), and diamines (e.g. histamine). These metabolites and related anabolic and catabolic intermediates are included, such as in the case of N-acetylaspartylgluterate (NAAG) synthesized de novo from N-acetylaspartate and glutamic acid. Sulfonic acid metabolites are also implicated, e.g. taurine.

Also included are specific modifications facilitated by enzymatic linkage of sulfate groups and similar functionalities, i.e. cholesterol sulfate. Endogenous compounds representing metabolites that might vary in concentration include the major metabolites of the tricarboxylic acid cycle (e.g. citrate, isocitrate, alpha-ketogluterate, succinate, fumarate, malate, and oxaloacetate), glycolysis (e.g. glucose, glucose-6-phosphate, fructose-6-phosphate, glyceraldehyde-3-phosphate, etc), and similar energy production metabolites. Signaling metabolites including but not limited to prostaglandins, cytokines, and hormones would be similarly included. Finally, lipid constituents, known to vary in accordance with disease state, should be noted as important metabolites (Eberlin, et al., Angewandte Chemie 49, 5953-5956 (2010); and Eberlin, et al., Cancer research 72, 645-654 (2012)). In certain embodiments, the metabolites analyzed are aspartic acid, ascorbic acid, glutamic acid, and taurine (inverse dependence).

A sample may be any material that includes one or more metabolites. In certain embodiments, the sample is an ex vivo sample. Such ex vivo samples are obtained in an clinically acceptable manner. In other embodiments, the sample is an in situ sample. In certain embodiments, the sample may be human, animal, or plant tissue or body fluid. In certain embodiments, the sample includes a microorganism to be analyzed. In particular embodiments, the sample is human tissue or body fluid. A tissue is a mass of connected cells and/or extracellular matrix material, e.g. skin tissue, endometrial tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, brain tissue, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed.

The sample is then analyzed using a mass spectrometry technique that is non-destructive of native tissue morphology. In that manner, a sample is analyzed by mass spectrometry to obtain a metabolite level in the sample, and because the analyzed sample remains intact, the metabolite level can be correlated with its originating source. There are numerous approaches that can be employed to conduct a mass spectral analysis of a sample without destroying the native morphology of the sample. Some of those approaches are discussed below.

Non-Destructive Solvents

In certain embodiments, the present invention provides new methodologies by which mass spectral analysis (such as ambient tissue imaging by desorption electrospray ionization mass spectrometry) of a sample, such as a tissue sample can be performed while morphology of the tissue section is kept intact or unmodified. Such an approach allows the metabolite level to be correlated with its originating source, while also allowing subsequent analysis of the tissue by histochemistry or many other techniques to be performed. This is a new methodology for non-destructive, morphologically friendly tissue analysis by mass spectrometry techniques, such as desorption electrospray ionization mass spectrometry. Thus in certain aspects, the invention provides methods for analyzing tissue that involve analyzing a tissue sample using a mass spectrometry technique, in which the technique utilizes a liquid phase that does not destroy native tissue morphology during analysis. In certain embodiments, analyzing involves imaging a tissue section.

In certain embodiments, methods of the invention allow extraction of metabolites from tissue during DESI-MS analysis while morphology of the tissue remains undisturbed, therefore the metabolite level to be correlated with its originating source, while also allowing subsequent analysis to be performed on the same tissue section. Particularly, methods of the invention allow high-quality 2D DESI-MS ion images to be directly compared and even overlaid with the H&E stained tissue section, allowing a better correlation between the spatial distribution of the metabolite species detected and the substructures of the tissue sample, such as a subject's brain. Pathological evaluation of the tissue sections confirmed that no morphological damage was caused to the tissue as a result of DESI-MS imaging when using appropriate solvents.

In certain aspects, the invention provides methods for imaging a metabolite containing sample (e.g., a tissue sample) that involve imaging a metabolite containing sample using a direct ambient ionization/sampling technique, in which the technique is performed in a manner that allows the sample to be subjected to identification and further analysis after imaging.

Another aspect of the invention provides analysis methods that involve obtaining a metabolite containing sample, imaging the sample using a mass spectrometry technique, in which the technique utilizes a liquid phase that does not destroy native tissue morphology during analysis, and performing a histochemistry analysis technique on the sample.

Another aspect of the invention provides methods for diagnosing cancer that involve obtaining a metabolite containing sample, imaging the sample using a mass spectrometry technique, in which the technique utilizes a liquid phase that does not destroy native tissue morphology during analysis, performing a histochemistry analysis technique on the sample, and diagnosing a cancer based results of the imaging and the performing steps.

Any mass spectrometry technique known in the art may be used with methods of the invention. Exemplary mass spectrometry techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom., 2:151-153, 1988). The content of each of these references in incorporated by reference herein its entirety.

Exemplary mass spectrometry techniques that utilize direct ambient ionization/sampling methods include desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desoption/ionization (ELDI; Shiea et al., J. Rapid Communications in Mass Spectrometry, 19:3701-3704, 2005). The content of each of these references in incorporated by reference herein its entirety.

In certain embodiments, the mass spectrometry technique is desorption electrospray ionization (DESI). DESI is an ambient ionization method that allows the direct ionization of species from thin tissue sections (Takats et al., Science, 306:471-473, 2004 and Takats, U.S. Pat. No. 7,335,897). DESI-MS imaging has been successfully used to diagnose multiple types of human cancers (Eberlin L S, Ferreira C R, Dill A L, Ifa D R, & Cooks R G (2011) Desorption Electrospray Ionization Mass Spectrometry for Lipid Characterization and Biological Tissue Imaging. Biochimica Et Biophysica Acta-Molecular And Cell Biology Of Lipids accepted); (Cooks R G, et al. (2011), Faraday Discussions 149:247-267).

Multivariate statistical analysis of the DESI-MS imaging data by means of principal component analysis and partial least squares discriminant analysis allowed a successful correlation between DESI-MS data and pathological evaluation in 88% of the cases analyzed (Dill A L, et al. (2011), Chemistry—a European Journal 17(10):2897-2902). DESI-MS imaging was also applied for the diagnosis of human cancers including; two types of kidney cancer (Dill A L, et al. (2010), Analytical and Bioanalytical Chemistry 398(7-8):2969-2978); human prostate cancer (Eberlin L S, et al. (2010), Analytical Chemistry 82(9):3430-3434); and the grading of brain gliomas (WHO grade II, grade III and grade IV (glioblastoma; Eberlin L S, et al. (2010), Angewandte Chemie-International Edition 49(34):5953-5956).

In addition to cancer diagnostics, DESI-MS imaging has been used to characterize tissues of other disease states, such as chemically profiling and imaging of human arterial plaques with atherosclerosis (Manicke N E, et al. (2009), Analytical Chemistry 81(21):8702-8707). In addition to the possibility of supplementing the DESI-MS solvent with ionization facilitator compounds (Jackson A U, Shum T, Sokol E, Dill A, & Cooks R G (2011), Analytical and Bioanalytical Chemistry 399(1):367-376), a unique capability of DESI-MS is the possibility to use reactants in the solvent to facilitate the ionization (reactive DESI) and detect important metabolic intermediates that can be difficult to ionize, such as cholesterol (Wu C P, Ifa D R, Manicke N E, & Cooks R G (2009), Analytical Chemistry 81(18):7618-7624).

Operated in an imaging mode, it uses a standard microprobe imaging procedure, which in this case involves moving the probe spray continuously across the surface while recording mass spectra. See for example, Wiseman et al. Nat. Protoc., 3:517, 2008, the content of which is incorporated by reference herein its entirety. Each pixel yields a mass spectrum, which can then be compiled to create an image showing the spatial distribution of a particular compound or compounds. Such an image allows one to visualize the differences in the distribution of particular compounds over the lipid containing sample (e.g., a tissue section). If independent information on biological properties of the sample are available, then the MS spatial distribution can provide chemical correlations with biological function or morphology. Moreover, the combination of the information from mass spectrometry and histochemical imaging can be used to improve the quality of diagnosis.

In particular embodiments, the DESI ion source is a source configured as described in Ifa et al. (Int. J. Mass Spec/rom. 259(8), 2007). A software program allows the conversion of the XCalibur 2.0 mass spectra files (.raw) into a format compatible with the Biomap software (freeware, http://www.maldo-msi.org). Spatially accurate images are assembled using the Biomap software.

Methods of the invention involve using a liquid phase that does not destroy native tissue morphology. Any liquid phase that does not destroy native tissue morphology and is compatible with mass spectrometry may be used with methods of the invention. Exemplary liquid phases include DMF, ACN, and THF. In certain embodiments, the liquid phase is DMF. In certain embodiments, the DMF is used in combination with another component, such as EtOH, $H_2O$, ACN, and a combination thereof. Other exemplary liquid phases that do not destroy native tissue morphology include ACN: EtOH, MeOH:$CHCl_3$, and ACN:$CHCl_3$.

In certain embodiments, methods of the invention involve performing a histochemical analysis on the tissue sample after it has been subjected to mass spectrometric analysis. Any histochemical analytical technique known in the art may be performed on the tissue, and the performed technique will depend on the goal of the analysis. Exemplary histochemical analytical techniques include H&E staining or immunohistochemistry.

Touch Spray

Aspects of the invention are accomplished using systems that include a probe having a tip composed of non-porous material. The tip is configured to contact a sample and retain a portion of the sample once the probe has been removed from the sample. Such a technique allows one to obtain diagnostic information without the removal of the sample. Since the sample remains in situ, it is possible to correlate the results to the originating source.

An electrode is coupled to the probe, and the probe is operably coupled to a mass analyzer. In certain embodiments, the probe includes a hollow inner bore in communication with the tip. Such a configuration allows solvent to be infused through the bore to interact with the sample to facilitate generation of ions of an analyte from the portion of the sample on the probe. Exemplary probes include scalpels, needles, burrs, paper clips, etc. In certain embodiments, the system further includes a source of nebulizing gas. The source of nebulizing gas may be configured to provide pulses of gas. Alternatively, the source of nebulizing gas may be configured to provide a continuous flow of gas.

Other aspects of the invention provide methods for analyzing a sample. The methods involve contacting a tip of a probe to a sample such that a portion of the sample is retained on the probe once the probe has been removed from the sample. The methods additionally involve applying solvent and a high voltage to the probe, thereby generating ions of an analyte from the portion of the sample on the probe, and analyzing the ions. In certain embodiments, the probe is composed of a non-porous material. An exemplary analysis technique is mass spectrometry.

Systems and methods of the invention may be used to analyze any metabolite containing sample, and are particularly useful for analyzing tissue samples, specifically in situ tissue samples.

Other aspects of the invention provide methods for analyzing tissue for a cancer. Those methods involve contacting a probe to an in situ tissue sample such that a portion of the sample is retained on the probe once the probe has been removed from the sample. The methods additionally involve applying solvent and a high voltage to the probe, thereby generating ions of an analyte from the portion of the sample on the probe, and analyzing the ions for an indication of cancer. The steps of the method may be performed iteratively around the in situ tissue sample to determine margins of a tumor.

Using this technique, mass spectral profiles are acquired rapidly (typically less than approximately one (1) second) with the spatial resolution determined directly by the probe's touch. Mass spectral profiles may also be averaged over time, such as approximately twenty (20) seconds. By sampling a point or a number of points the method of analyzing the tissue surface is fast with no sample preparation. The method of analysis can also be undertaken intra-operatively which may be important in establishing disease margins on a time scale that is useful during surgery.

In certain embodiments, Touch Spray can be used to identify positive margins in a manner that will allow surgical intervention during the operative procedure. In certain embodiments, Touch Spray identifies metabolite markers, such as lipid markers, that detect positive margins in the operating room to enable additional resection if needed and detect markers of cancer aggressiveness. Given that cancer patients may have positive margins, the impact of additional resection for residual disease will be determined in a relatively short time frame.

Touch Spray provides a method for intra-surgical diagnostics by MS on a point-to-point basis. An advantage of Touch Spray over other mass spectrometry techniques is its ability to sample tissues in vivo and immediately analyze ex vivo, leaving the in situ sample intact so that metabolite levels can be rapidly correlated back to the origin of the sample. Touch Spray allows diagnostic information to be obtained without the removal of tissue sample.

Spot analysis by Touch Spray allows for detailed and automated comparisons of metabolite profiles with those associated with pathological conditions. This ambient ionization spray-based technique provides information on a wide range of compounds. Furthermore this technique works in both positive and negative ion modes. Both modes are complementary and similarly informative. Hence, the wide range of metabolite molecular information can be utilized in defining disease in current and retrospective examinations.

Systems and methods of the invention find particular use in disease diagnostics, particularly cancer diagnostics and in the operating room to determine tumor margins. Currently, tissue is first removed and then examined by a pathologist. The pathologist evaluates whether or not the removed tissue has margins of healthy tissue. The pathologist relays the evaluation to the surgeon which gives the surgeon information regarding whether or not to remove more tissue. Using Touch Spray, the surgeon can make the decision to resect more tissue or not to resect based on mass spectral data suggesting that the investigated sample, in this case tissue, is diseased or not. It is envisioned that under ideal conditions analysis by touch spray may result in resection of almost only cancerous tissue, leaving almost all healthy tissue behind.

Touch spray is performed by two basic steps: (1) touching a sample with a probe in order to transfer analyte from the sample to the probe and (2) spraying analyte on the probe into a mass spectrometer. The first step includes touching the surface of a sample, such as tissue, with a probe including an end such as a metallic point and/or a roughened surface. The step of touching a sample can be performed in a variety of ways including dry, wet, and dip. A probe may be moistened by the addition of 1-2 µL of extractive solvent. A wet touch may facilitate the transfer of analytes from the sample to the probe surface. A wetted probe including solvated analyte may be allowed to dry. Drying under these conditions typically takes less than 30 seconds but can vary based on the solvent composition and volume of solvent applied to the probe. After the previously wetted probe has essentially dried, the probe with analyte is placed in front of a mass spectrometer and analyzed in a procedural manner similar to electrospray ionization or dry touch. Because the in situ sample remains intact, it is possible to correlate the diagnostic results, e.g., metabolite levels, to their originating source.

Another aspect of touching is the amount or degree of contact between the probe and the sample. A probe may touch a sample in a variety of ways including point, line, and area. A point touch may include a single point touch such as when the probe includes a tip or a multiple point touch such as when the probe includes an area at an end. A point touch of a surface of a sample may include a small circular motion of the probe and may affect a small amount of sample material, typically not more than 1 mm in diameter. A line touch occurs when the probe is touched to a surface at a starting point and traversed to another point. The movement may be by straight line or by a scratch.

The step of spraying includes the application of solvent and voltage to the probe placed in close proximity to the inlet of a mass spectrometer. The mass spectrometer is capable of analyzing the analyte in a procedural manner similar to electrospray ionization. The step of spraying analyte from the probe into a mass spectrometer can be performed in a variety of ways including variations in solvent, solvent application, application in high voltage, and probe placement.

The application of spray solvent to the probe can be performed in a variety of ways including two methods: (1) discontinuous and (2) continuous. Discontinuous application includes applying approximately 1-2 μL of solvent to the probe. Typically solvent is applied using a micropipettor to aid in obtaining reproducible results. The location of solvent application (i.e, where solvent lands on the probe), often no more than a few millimeters, is important for electrospray formation, spray stability, and thus the quality of mass spectra obtained. The location of solvent application varies based on probe geometry, surface, and spray solvent composition. Continuous application of solvent includes spray solvent delivered via a solvent transfer line, connected to a solvent source such as a syringe, and possibly driven by a syringe pump. The location of spray solvent application is important to proper functioning, analogous to the discontinuous method. Continuous application of the spray solvent allows for on/off switching by either removing the application of high voltage to the probe or ceasing solvent flow via the syringe pump.

The application of high voltage (for example, within the range of approximately 3-approximately 5 kilovolts) to the probe can be made directly via metal connector or inductively. The location of high voltage application is less important to spray formation in the case of a metallic probe, but is more important in less conductive materials. High voltage application may be applied after probe placement in an optional holding device and prior or essentially simultaneous to solvent application.

Touch Spray can be used to analyze tissue, as described in the Examples below. For in situ sampling, Touch Spray can be performed using a probe fitted with a small flattened needle connected to a small reservoir of solvent that will be touched onto tissue to allow a small amount of material to adhere. The probe will be held in front of a miniature mass spectrometer, a voltage will be applied to the probe and the solvent will cause a spray of droplets into the MS.

Reactive Touch Spray possesses the ability to perform chemical derivatization concurrently with mass spectral analysis, allowing for specific analytes to be distinguished and/or enhanced. Reactions are not confined to only covalent bond formation but include reactive intermediates and gas-phase adduction products as well. The reagents used in Reactive Touch Spray can be added to the spray solvent, continuous or discontinuous, or applied to the probe prior to touching. Touch Spray can be used in the detection of metabolites from samples. In an exemplary embodiment, the metabolite is a lipid metabolite, and the lipids patterns are useful in differentiating disease states.

Ionization Using Wetted Porous Material

In other embodiments, mass spectrometry probes made of porous material are used with methods of the invention. This embodiment involves contacting a porous probe to an in situ sample such that a portion of the sample is retained on the porous probe once the probe has been removed from the sample, and applying solvent and a high voltage to the probe, thereby generating ions of an analyte from the portion of the sample on the probe. Such a technique allows one to obtain diagnostic information without the removal of the sample. Since the sample remains in situ, it is possible to correlate the results to the originating source.

Figure 40:
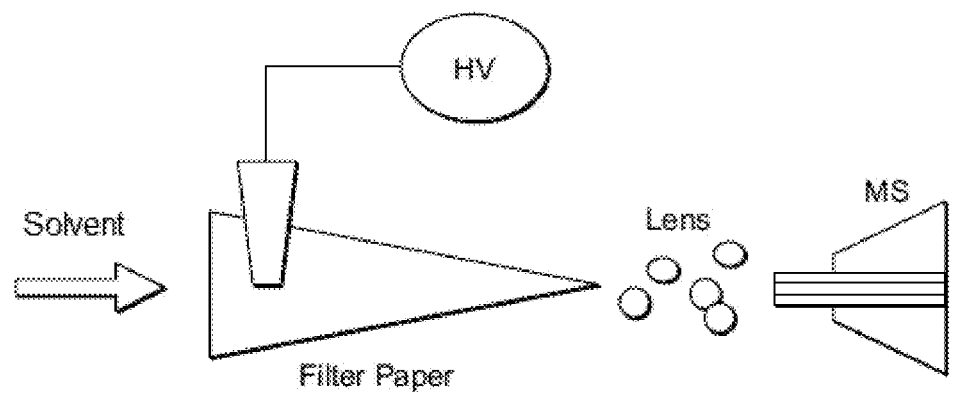
FIG. 40 is a schematic of a probe of porous material that has already been contacted to an in situ sample. A portion of the sample is retained on the porous material. The porous material is connected to a high voltage source and a solvent is applied to the porous material. Ions are produced and ejected from the porous material and into a mass spectrometer.

Probes comprised of porous material that is wetted to produce ions are described in Ouyang et al. (U.S. patent application Ser. No. 13/265,110 and PCT application number PCT/US10/32881), the content of each of which is incorporated by reference herein in its entirety. An exemplary probe is shown in FIG. 40. Porous materials, such as paper (e.g. filter paper or chromatographic paper) or other similar materials are used to hold and transfer liquids and solids, and ions are generated directly from the edges of the material when a high electric voltage is applied to the material. The porous material is kept discrete (i.e., separate or disconnected) from a flow of solvent, such as a continuous flow of solvent. Instead, sample is either spotted onto the porous material or swabbed onto it from a surface including the sample. The spotted or swabbed sample is then connected to a high voltage source to produce ions of the sample which are subsequently mass analyzed. The sample is transported through the porous material without the need of a separate solvent flow. Pneumatic assistance is not required to transport the analyte; rather, a voltage is simply applied to the porous material that is held in front of a mass spectrometer.

In certain embodiments, the porous material is any cellulose-based material. In other embodiments, the porous material is a non-metallic porous material, such as cotton, linen wool, synthetic textiles, or plant tissue. In still other embodiments, the porous material is paper. Advantages of paper include: cost (paper is inexpensive); it is fully commercialized and its physical and chemical properties can be adjusted; it can filter particulates (cells and dusts) from liquid samples; it is easily shaped (e.g., easy to cut, tear, or fold); liquids flow in it under capillary action (e.g., without external pumping and/or a power supply); and it is disposable.

In certain embodiments, the porous material is integrated with a solid tip having a macroscopic angle that is optimized for spray. In these embodiments, the porous material is used for filtration, pre-concentration, and wicking of the solvent containing the analytes for spray at the solid type.

In particular embodiments, the porous material is filter paper. Exemplary filter papers include cellulose filter paper, ashless filter paper, nitrocellulose paper, glass microfiber filter paper, and polyethylene paper. Filter paper having any pore size may be used. Exemplary pore sizes include Grade 1 (11 μm), Grade 2 (8 μm), Grade 595 (4-7 μm), and Grade 6 (3 μm). Pore size will not only influence the transport of liquid inside the spray materials, but could also affect the formation of the Taylor cone at the tip. The optimum pore size will generate a stable Taylor cone and reduce liquid evaporation. The pore size of the filter paper is also an important parameter in filtration, i.e., the paper acts as an online pretreatment device. Commercially available ultra-filtration membranes of regenerated cellulose, with pore sizes in the low nm range, are designed to retain particles as small as 1000 Da. Ultra filtration membranes can be commercially obtained with molecular weight cutoffs ranging from 1000 Da to 100,000 Da.

Probes of the invention work well for the generation of micron scale droplets simply based on using the high electric field generated at an edge of the porous material. In particular embodiments, the porous material is shaped to have a macroscopically sharp point, such as a point of a triangle, for ion generation. Probes of the invention may have different tip widths. In certain embodiments, the probe tip width is at least about 5 μm or wider, at least about 10 μm or wider, at least about 50 μm or wider, at least about 150 μm or wider, at least about 250 μm or wider, at least about 350 μm or wider, at least about 400μ, or wider, at least about 450 μm or wider, etc. In particular embodiments, the tip width is at least 350 μm or wider. In other embodiments, the probe tip width is about 400 µm. In other embodiments, probes of the invention have a three dimensional shape, such as a conical shape.

As mentioned above, no pneumatic assistance is required to transport the droplets. Ambient ionization of analytes is realized on the basis of these charged droplets, offering a simple and convenient approach for mass analysis of solution-phase samples. Sample solution is directly applied on the porous material held in front of an inlet of a mass spectrometer without any pretreatment. Then the ambient ionization is performed by applying a high potential on the wetted porous material. In certain embodiments, the porous material is paper, which is a type of porous material that contains numerical pores and microchannels for liquid transport. The pores and microchannels also allow the paper to act as a filter device, which is beneficial for analyzing physically dirty or contaminated samples. In other embodiments, the porous material is treated to produce microchannels in the porous material or to enhance the properties of the material for use as a probe of the invention. For example, paper may undergo a patterned silanization process to produce microchannels or structures on the paper. Such processes involve, for example, exposing the surface of the paper to tridecafluoro-1,1,2,2-tetrahydrooctyl-1-trichlorosilane to result in silanization of the paper.

In other embodiments, a soft lithography process is used to produce microchannels in the porous material or to enhance the properties of the material for use as a probe of the invention. In other embodiments, hydrophobic trapping regions are created in the paper to pre-concentrate less hydrophilic compounds. Hydrophobic regions may be patterned onto paper by using photolithography, printing methods or plasma treatment to define hydrophilic channels with lateral features of 200–1000 µm. See Martinez et al. (Angew. Chem. Int. Ed. 2007, 46, 1318-1320); Martinez et al. (Proc. Natl. Acad. Sci. USA 2008, 105, 19606-19611); Abe et al. (Anal. Chem. 2008, 80, 6928-6934); Bruzewicz et al. (Anal. Chem. 2008, 80, 3387-3392); Martinez et al. (Lab Chip 2008, 8, 2146-2150); and Li et al. (Anal. Chem. 2008, 80, 9131-9134), the content of each of which is incorporated by reference herein in its entirety. Liquid samples loaded onto such a paper-based device can travel along the hydrophilic channels driven by capillary action.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Mass Spectrometry Techniques Using Non-Destructive Solvents

This example shows mass spectrometry analysis of a lipid metabolite performed in a non-destructive matter, so that the metabolite level can be correlated to its originating source, and so that other analyses of the same sample can be performed after the mass spectrometry analysis is performed. This technique, which uses a variety of solvent systems for imaging, allows mass spectrometry analysis (e.g., DESI-MS imaging) of chemical compounds to be performed on lipid metabolite containing samples (e.g., tissue sections), while the morphology of the tissue remains unmodified. After DESI-MS imaging, the tissue can be correlated back to its originating source, while also being used for H&E staining, immunohistochemistry, and any other tissue analysis technique to obtain more information on the distribution of its chemical constituents.

A frozen brain from a male mouse was purchased from Rockland Immunochemicals, Inc. (Gilbertsville, Pa., USA) and stored at −80° C. until it was sliced into coronary sections of varying thickness (2 µm, 3 µm, 5 µm and 15 µm) using a Shandon SME Cryotome cryostat (GMI, Inc., Ramsey, Minn., USA) and thaw mounted onto glass slides. The glass slides were stored in a closed container at −80° C. until analysis, when they were allowed to come to room temperature and dried in a dessicator for approximately 15 minutes. All human tissue samples were handled in accordance with approved institutional review board (IRB) protocols at Indiana University School of Medicine. Six human bladder cancer and paired normal samples, four human prostate cancer and paired normal samples and one human kidney cancer and paired normal sample were obtained from the Indiana University Medical School Tissue Bank. All tissue samples were flash frozen in liquid nitrogen at the time of collection and subsequently stored at −80° C. until sliced into 5 or 10 µm thick sections. The 5 and 15 µm thick sections were used for DESI-MS imaging experiments followed by either p63 immunohistochemistry or H&E stain, respectively. Tissue sections not analyzed by DESI-MS were used in control experiments. The thin tissue sections were thaw mounted to glass slides; each slide containing one section of tumor tissue and one section of adjacent normal tissue from the same patient. The glass slides were stored in closed containers at −80° C. Prior to analysis, they were allowed to come to room temperature and then dried in a dessicator for approximately 15 minutes.

The DESI ion source was a lab-built prototype, similar to a commercial source from Prosolia Inc. (Indianapolis, Ind. USA), configured as described elsewhere (Watrous J D, Alexandrov T, & Dorrestein P C (2011), Journal of Mass Spectrometry 46(2):209-222). It consists of an inner capillary (fused silica, 50 µm i.d., 150 µm o.d.) (Polymicro Technologies, AZ, USA) for delivering the spray solvent and an outer capillary (250 µm i.d., 350 µm o.d.) for delivering nitrogen nebulizing gas. The DESI spray was positioned 2.5 mm from the tissue sample at an incident angle of 54°. A low collection angle of 10° was chosen to ensure the most efficient collection of the material being desorbed. The distance between the spray and the inlet was 6.0 mm. Multiple spray solvent systems were tested in this example, including ACN, $H_2O$, MeOH, ethanol (EtOH), tetrahydrofuran (THF), N,N-dimethylformamide (DMF), chloroform (CHCl$_3$), acetone and many of their binary mixtures in a ratio of (1:1). The only tertiary mixture investigated was of ACN:H$_2$O:DMF at different v/v proportions, such as (8:3:1 and 1:1:1). DESI-MS experiments were carried out in the negative ion mode, using a 5 kV spray voltage and a flow rate of 0.5-1.5 µL/min depending on the solvent system of choice. The nebulizing gas (N2) pressure was set for all experiments at 175-180 psi. The mass spectrometer used was a LTQ linear ion trap mass spectrometer controlled by XCalibur 2.0 software (Thermo Fisher Scientific, San Jose, Calif., USA).

Analyses were performed using an imaging approach. The tissues were scanned using a 2D moving stage in horizontal rows separated by a 150 µm vertical step for the mouse brain imaging assay (FIG. 3), and 250 µm vertical step for the human tissue imaging assays. For the DESI-MS assay shown in FIG. 2, the same mouse brain section was imaged 10 times with DMF:EtOH (1:1) and each analysis was performed in 10 lines of 250 µm. After one analysis was concluded, the moving stage was set to coordinate 0,0 (x,y) for the new analysis to be performed. The surface moving stage included an XYZ integrated linear stage (Newport, Richmond, Calif., USA) and a rotary stage (Parker Automation, Irwin, Pa., USA). A software program allowed the conversion of the XCalibur 2.0 mass spectra files (.raw) into a format compatible with the Biomap software (freeware, http://www.maldi-msi.org). Spatially accurate images were assembled using the BioMap software. The color scale is normalized to the most intense (100% relative intensity) peak in the mass spectra.

Tissue sections were subjected to H&E staining after DESI-MS imaging analysis or after being dried in a dessicator (control sections). All chemicals used for the H&E staining were purchased from Sigma-Alrich (St. Louis, Mo., USA). The H&E staining was performed at room temperature: dip in MeOH for 2 minutes, rinse in water (10 dips), stain in Harris modified hematoxylin solution for 1.5 minutes, rinse in water (10 dips), 1 quick dip in 0.1% ammonia (blueing agent), rinse in water (10 dips), counterstain in Eosin Y (8 seconds), rinse in 100% EtOH (10 dips), rinse again in 100% EtOH (10 dips), rinse in Xylene (6 dips) and rinse again in Xylene (6 dips). Sections were allowed to dry and covered with a glass cover slide. Immunohistochemistry assays were performed in the Veterinary Department at Purdue University, in accordance to their standard protocol. The primary antibody p63 (4A4):sc-8431 was purchased from Santa Cruz Biotechnology, INC (Santa Cruz, Calif., USA).

Pathological evaluation of the human tissue sections that were either H&E stained or subjected to p63 immunohistochemistry was performed at IU School of Medicine in a blind fashion. Optical images of tissue sections were obtained using a SM-LUX Binocular Brightfield Microscope (Leitz, Wetzlar, Germany) under 16, 25 and 40× magnification.

The solvent system used in DESI tissue imaging is taught to be an important technical parameter for optimization (Badu-Tawiah A, Bland C, Campbell D I, & Cooks R G (2010), Journal of the American Society for Mass Spectrometry 21(4):572-579; and Green F M, Salter T L, Gilmore I S, Stokes P, & O'Connor G (2010), Analyst 135(4):731-737). Many studies have shown that the chemical and physical properties of the solvent system used affect the molecular information obtained during DESI-MS tissue imaging (Ellis S R, et al. (2010), J. Am. Soc. Mass Spectrom. 21(12):2095-2104). Optimization of the spray composition allows targeted classes of compounds to be enhanced depending on the overall goal. Besides the chemical information, the effect of the solvent system on the morphology of the tissue being analyzed is a factor in DESI-MS imaging. Commonly used DESI-MS imaging solvent systems, such as mixtures of water with methanol or acetonitrile (Wiseman J M, Ifa D R, Venter A, & Cooks R G (2008), Nature Protocols 3(3):517-524), with or without an acidic modifier, yield extensive chemical information but are known to cause depletion and destruction of the tissue sections, precluding correlation of metabolite levels by to their originating source or precluding any consecutive analysis to be performed. To overcome these problems, different solvents such as ACN, H$_2$O, MeOH, ethanol (EtOH), tetrahydrofuran (THF), N,N-dimethylformamide (DMF), chloroform (CHCl$_3$), acetone and mixtures of these were investigated in the analysis of 15 µm thick serial coronary mouse brain tissue sections.

A binary mixture of MeOH:H$_2$O (1:1, v/v) or ACN:H$_2$O (1:1, v/v) has been commonly used in DESI imaging of brain tissue, yielding high signal intensity for polar lipids and free fatty acids (Eberlin L S, Ifa D R, Wu C, & Cooks R G (2010), Angewandte Chemie-International Edition 49(5): 873-876; and Wiseman J M, Ifa D R, Song Q Y, & Cooks R G (2006), Angewandte Chemie-International Edition 45(43):7188-7192). The majority of the ions observed in the mass spectra obtained from the solvent systems tested here correspond to commonly observed lipid species in brain tissue when using standard MeOH:H$_2$O (1:1), such as deprotonated free fatty acids, phosphatidylserines (PS), phosphatidylinositols (PI) and sulfatides (ST) (Eberlin L S, Ifa D R, Wu C, & Cooks R G (2010), Angewandte Chemie-International Edition 49(5):873-876). Variations in the relative abundance of the lipid species and in the total ion signal obtained were observed depending on the solvent composition. For instance, spectra obtained when using pure methanol as the solvent system showed higher relative abundance of fatty acid dimers in the m/z 500-700 region of the mass spectrum. In particular, it was observed that pure DMF yielded spectra with high total abundance and with chemical information that is very similar to that which is obtained using MeOH:H$_2$O.

Interestingly, the DMF spray was observed to not cause tissue destruction. The effect of DMF in the tissue was further explored by combining this solvent with other solvents in binary (1:1 v/v) and tertiary mixtures. The combination of DMF with either ACN, EtOH, THF or CHCl$_3$ yielded very high ion signal and chemical information similar to what is seen using MeOH:H$_2$O. Combinations of DMF with either H$_2$O or MeOH greatly enhanced the signal of low molecular weight compounds, such as small metabolites, FAs and FA dimers (Eberlin L S, Ferreira C R, Dill A L, Ifa D R, & Cooks R G (2011) Desorption Electrospray Ionization Mass Spectrometry for Lipid Characterization and Biological Tissue Imaging. Biochimica Et Biophysica Acta-Molecular And Cell Biology Of Lipids accepted). In terms of spray stability and total ion abundance, the combinations of DMF with either EtOH or ACN are great solvent systems for tissue imaging experiments. The change in chemical information obtained by DESI-MS using different solvent combinations can be compared to the use of different matrices in MALDI imaging, but in DESI-MS imaging experiments, the "matrix" is delivered in real-time, spot-by-spot, without the need for sample preparation or without causing spatial delocalization of molecules.

Figure 1B:
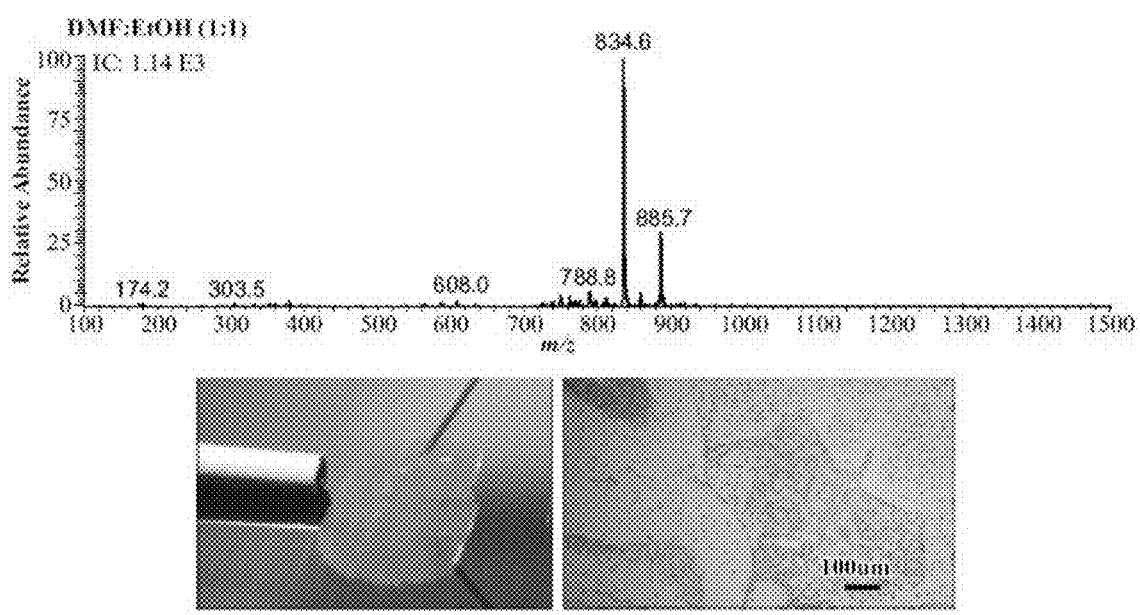
FIG. 1B shows the chemical information and physical effect of a new solvent system DMF:EtOH (1:1) on sequential 15 μm thick mouse brain tissue sections.
Figure 1C:
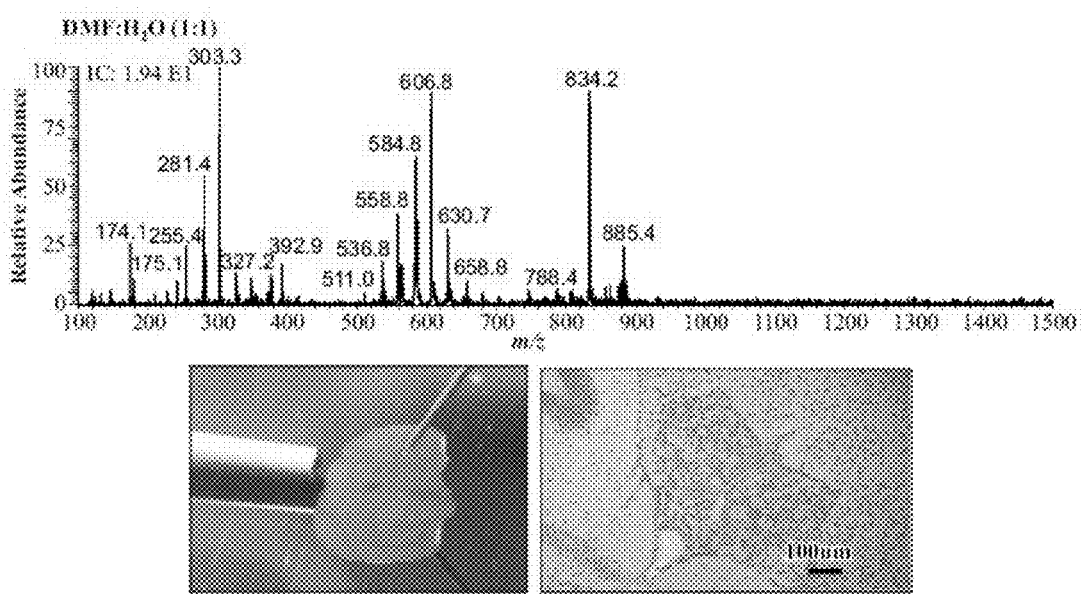
FIG. 1C shows the chemical information and physical effect of a new solvent system DMF:$H_2O$ (1:1) on sequential 15 μm thick mouse brain tissue sections. DESI-MS mass spectra of similar regions of the gray brain matter obtained with (A) MeOH:$H_2O$ (1:1) and (B) DMF:EtOH (1:1) solvent systems show similar molecular information, while (C) DMF:$H_2O$ (1:1) favored the ionization of smaller m/z molecules such as fatty acids and metabolites. Insets (LHS) show an optical image of the DESI-MS imaging experiment on mouse brain tissue. The physical damage to the tissue is strikingly different between the standard solvent systems and the new morphologically friendly solvent systems. Insets (RHS) show magnified bright-field optical images of the same region of the different mouse brain tissue sections which were first imaged by DESI-MS with the different solvent systems and subsequently H&E stained.

Importantly, none of these solvent combinations were observed to cause visual damage to the 15 µm thick tissue sections that were analyzed. FIG. 1 shows the physical and chemical effect of two of the new solvent systems developed, DMF:EtOH (1:1) and DMF:H$_2$O (1:1) in comparison to the standard MeOH:H$_2$O solvent system. DESI-MS conditions were kept identical in all analyses performed. It is striking to observe that while extensive chemical information was obtained from the tissue sections when using DMF:H$_2$O and DMF:EtOH, tissue integrity was preserved.

As observed in the optical images shown of the DESI-MS experiment, damage to the tissue was insignificant when using DMF solvent systems. To confirm preservation of tissue integrity, H&E staining was performed on the tissue sections previously analyzed by DESI-MS. H&E staining is a commonly used histochemical protocol to evaluate cellular structure and tissue morphology by light microscopy. Careful microscopic examination of the H&E tissue sections revealed no damage or change in the cellular morphology of the sample after DESI analysis using DMF:EtOH and DMF:H$_2$O solvent systems, while the tissue analyzed using MeOH:H$_2$O was found to be altered and damaged, as was macroscopically observed. DESI-MS analysis of sequential mouse brain tissue sections of 2, 3 and 5 µm thicknesses was also performed, and sequential H&E staining of the tissue sections also revealed that no morphological damage occurred following DESI-MS analysis using DMF:EtOH or DMF:ACN as the solvent system.

Figure 2A:
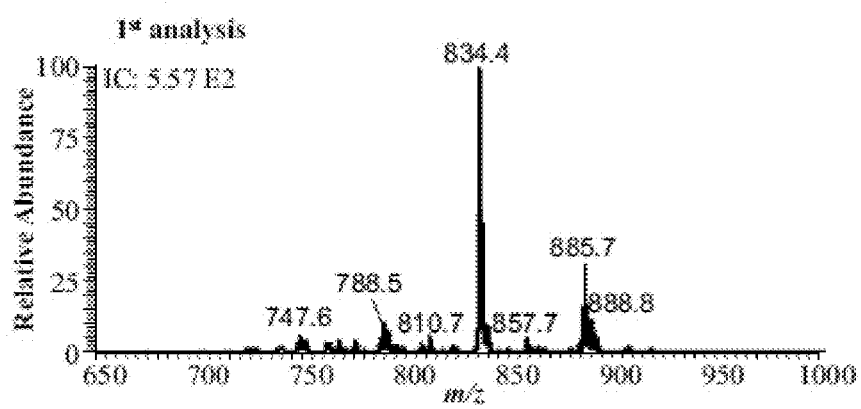
FIGS. 2A-2B show repeated DESI-MS imaging analysis of a mouse brain tissue section using DMF:EtOH as the solvent system. Mass spectra of gray matter region of a 15 μm thick mouse brain tissue section is shown for the 1st (FIG. 2A) and 10th (FIG. 2B) DESI-MS analysis of the same tissue section.
Figure 2B:
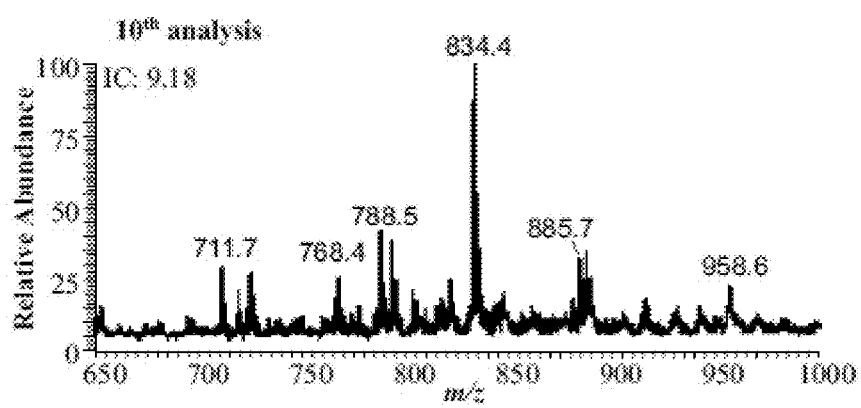
Figure 2C:
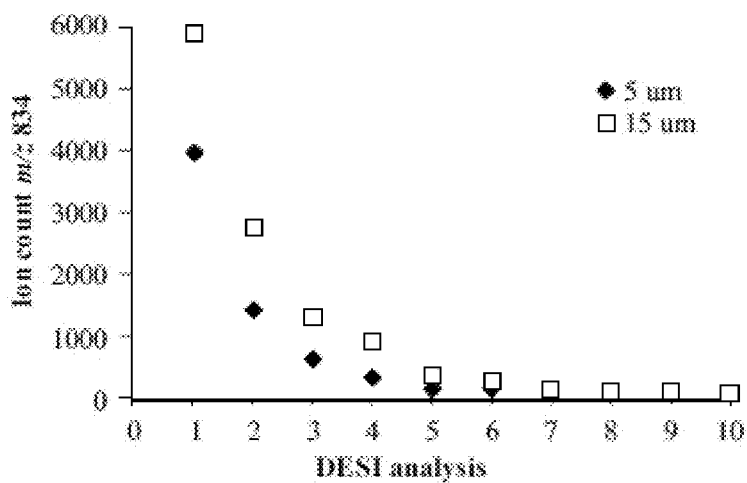
FIG. 2C shows a plot of the total intensity of the major ion m/z 834.4 (PS 18:0/22:6) was obtained for the 15 μm thick mouse brain tissue and for a 5 μm thick mouse brain tissue section which was subjected to the same repeated imaging experiment. The decay profile of the ion signal with DESI analysis repetition is consistent with the accepted extraction mechanism.
Figure 3A:
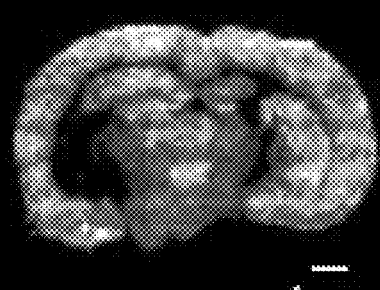
FIGS. 3A-3E show DESI-MS ion images obtained from a 15 μm thick mouse brain coronal section using DMF:EtOH (1:1) as the solvent system showing the distribution of the ions at m/z 834.3, PS (18:0/22:6) (FIG. 3A); m/z 888.6, ST (24:1) (FIG. 3B); m/z 890.7, ST (24:0) (FIG. 3C); m/z 885.6, PI (18:0/20:4) (FIG. 3D); and m/z 303.3, FA (20:4) (FIG. 3E).
Figure 3B:
Figure 3C:
Figure 3D:
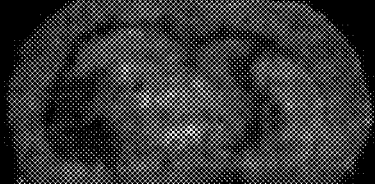
Figure 3E:
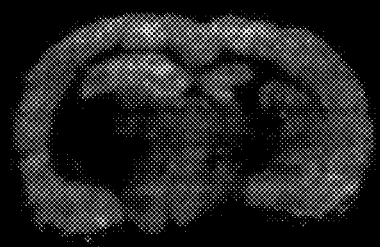
Figure 3F:
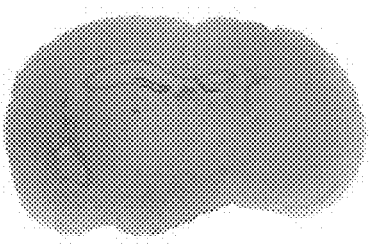
FIG. 3F shows an optical image of the same tissue section first imaged by DESI-MS and then H&E stained. High quality two-dimensional ion images were obtained under standard optimized DESI-MS imaging conditions at a lateral resolution of approximately 180 μm.

The physical and chemical effect of the DMF:EtOH solvent system was further investigated by performing several DESI-MS analyses of the same mouse brain tissue section. The same tissue region of a 5 µm and a 15 µm thick tissue section were analyzed 10 times using the DESI-MS moving stage system. Mass spectra were recorded for 10 rows (250 µm step size) of each mouse brain section and after 10 analyses had been performed, each tissue section was H&E stained and observed under brightfield microscopy under 16-40× magnification. FIGS. 2A and B show the mass spectra obtained from the gray matter region of the 5 µm thick mouse brain tissue section from the 5$^{th}$ row scanned using DMF:EtOH in the 1$^{st}$ and 10$^{th}$ DESI-MS analysis, respectively. The ion count is approximately 60 times greater in the 1$^{st}$ analysis of the mouse brain compared to the ion count obtained in the 10$^{th}$ analysis of the same region. The ion count of the main ion observed in the gray matter region of the 5$^{th}$ row scanned, m/z 834.4 (PS 18:0/22:6), was plotted as a function of the DESI-MS analysis number for both the 5 µm and a 15 µm thick tissue sections, shown in FIG. 2C.

Interestingly, the signal of the typical ion of m/z 834.4 obtained in the 3$^{rd}$ or even 4$^{th}$ DESI-MS analysis was still observed at high intensities. Furthermore, the decay profile of the ion count is consistent with the extraction mechanism proposed for DESI-MS (Costa A B & Cooks R G (2008), Chem. Phys. Lett. 464(1-3):1-8). While a MeOH:H$_2$O spray extracts the chemical compounds from the tissue cells resulting in tissue damage, the DMF based solvent system is able to extract the chemical compounds from the tissue section without disturbing the tissue morphology. H&E staining of both a 5 µm and a 15 µm thick tissue section after ten DESI-MS imaging analyses revealed no damage to the tissue, indicating that the repetitive removal of the phospholipids by the DESI solvent spray does not affect the morphology of the cells. In fact, the extraction process that occurs in DESI-MS is comparable to the fixative procedures commonly used in histology for lipid removal (DiDonato D & Brasaemle D L (2003), Journal of Histochemistry & Cytochemistry 51(6):773-780), such as the alcohol wash used in the initial step of the H&E staining data. This alcohol wash step extracts the majority of cellular phospholipids while the cellular cytoskeletal elements are kept intact. Since hematoxylin stains nucleoproteins and eosin stains intracellular and extracellular proteins, the removal of the lipid content with conservation of the tissue integrity by DESI-MS does not interfere with this standard histochemistry protocol. Importantly, the use of DMF based solvent systems or even other solvent systems with similar morphologically-friendly properties allows pathological evaluation to be performed on the same tissue section previously analyzed by DESI-MS but with acquisition of complementary results.

All combinations of DMF with other solvents used in the DESI-MS assays on mouse brain tissue sections were found to not destroy the native morphology of the tissue. Other pure solvents, such as ACN, DMF, THF, ethanol and others did not cause damage to the tissue integrity as observed in the H&E stains. A few other combinations that did not contain DMF, such as ACN:EtOH (1:1), MeOH:CHCl$_3$ (1:1) and ACN:CHCl$_3$ (1:1), did not destroy the native morphology of the tissue. The morphological effect that the DESI spray has on tissue appear to be related to the physical and chemical properties of the solvent systems itself.

While solubility of the proteic cellular and extracellular components of the tissue section in the DESI spray solvent system plays a role in the conservation of the tissue morphology integrity, the physical properties of the solvent system such as surface tension and its effects on the dynamics of the DESI spray primary droplets also impact the damage caused to the tissue. When solubilization of cellular and extracellular components that keep cellular morphological integrity intact occurs, the tissue becomes more susceptible to the mechanical action of the DESI spray droplets. Therefore, tissue damage should be related to both solubilization of tissue components and mechanical action of the DESI spray system. The fact that the morphologically-friendly solvent systems described here do not disturb tissue integrity appear to be related to the physical properties of the DESI spray primary droplets, but also on the solubility of tissue components on the solvent system.

Chemical information and image quality are important factors in DESI-MS imaging applications. The geometric parameters of the DESI spray as well as the choice of solvent system, gas pressure and solvent flow are important when optimizing imaging conditions. When the solvent system is modified, it is important to observe that the spray spot is stable and that the ion signal intensity is maximized for obtaining good quality 2D chemical images.

FIG. 3 shows ion images of a mouse brain tissue section obtained using DMF:EtOH as the solvent system. The spray geometry and gas pressure conditions used in this imaging experiment are standard for DESI-MS imaging applications (Eberlin L S, Ifa D R, Wu C, & Cooks R G (2010), Angewandte Chemie-International Edition 49(5):873-876; and Ifa D R, Wiseman J M, Song Q Y, & Cooks R G (2007), International Journal of Mass Spectrometry 259(1-3):8-15). In terms of solvent flow, it was observed that at a regular DESI-MS imaging flow rate of 1.5 µL/min a larger spot size is obtained with DMF solvent combinations as compared to standard mixtures of water with MeOH or ACN at the same flow. The high stability and larger diameter of the spray spot can be associated with the higher boiling point of DMF (153° C.), when compared to the boiling point of solvents as MeOH and ACN. Smaller diameter spray spots can be achieved by using either a lower solvent flow rate or by mixing DMF with a higher ratio of a solvent with higher volatility, such as a mixture of DMF:EtOH (1:2). A solvent flow of 0.5 µL/min was used for the mouse brain imaging experiments using binary mixtures of DMF so that a spot size of approximately 180 µm was obtained. Lower solvent consumption as a result of using a lower flow rate is advantageous in DESI-MS imaging applications.

In the images shown in FIG. 3, two distinctive MS peak patterns associated with the lipid compositions representative of the gray and white matter of the brain were observed in the negative-ion mode for the brain section analyzed (Eberlin L S, Ifa D R, Wu C, & Cooks R G (2010), Angewandte Chemie-International Edition 49(5):873-876). The ion images of m/z 834.3, PS 18:0/22:6 (FIG. 3A), m/z 885.6, PI 18:0/20:4 (FIG. 3D) and m/z 303.3, FA 20:4 (FIG. 3E) show a homogeneous distribution in the brain gray matter, which are complementary and distinct from the ion images of m/z 888.8 (ST 24:1, FIG. 3B) and m/z 890.7 (ST 24:0, FIG. 3C), which are homogeneously distributed in the mouse brain white matter. FIG. 3F shows the optical image of the same tissue section which was H&E stained after DESI-MS imaging was performed. This order of analysis in which ambient MS imaging is performed followed by histochemical analysis of the same tissue section is comparable to the "post-acquisition staining" methodology used in MALDI-MS imaging (Schwamborn K, et al. (2007), International Journal of Molecular Medicine 20(2):155-159). The high-quality 2D DESI-MS ion images can be directly compared and even overlaid with the H&E stained tissue section, allowing a better correlation between the spatial distribution of the lipid species detected and the substructures of the mouse brain.

The capability to perform DESI-MS imaging and histochemical analysis of the same tissue section is important in the investigation of diseased tissue. The comparison of histological features from stained sections with corresponding molecular images obtained by ambient imaging MS is important for accurate correlations between molecular signatures and tissue disease state. This is especially true in the analysis of cancerous tissue sections which are very often highly heterogeneous, with regions of containing various tumor cell concentrations (Agar N Y R, et al. (2011), Neurosurgery 68(2):280-290), infiltrative normal tissue (Dill A L, et al. (2011), Chemistry—a European Journal 17(10): 2897-2902), precancerous lesions (Eberlin L S, et al. (2010), Analytical Chemistry 82(9):3430-3434), etc. Integration of DESI-MS imaging into a traditional histopathology workflow required that the mass spectrometric analysis not interfere with the morphology of the tissue section. Provided this is the case, the combination of the two different types of data (as represented by the case of superimposed images) greatly increases discrimination between different tissue types including that between diseased and healthy tissue.

To investigate this capability, human bladder, kidney and prostate cancer tissues along with adjacent normal samples were analyzed by DESI-MS imaging in the negative ion mode using one of our histology compatible solvent system and sequentially H&E stained. The lipid species present in the tissue sections were identified based on collision-induced dissociation (CID) tandem MS experiments and comparison of the generated product ion spectra with literature data (Hsu F F & Turk J (2000), Journal of the American Society for Mass Spectrometry 11(11):986-999). FIG. 4 shows a series of negative ion mode DESI-MS ion images of species commonly observed in human bladder transitional cell carcinoma and adjacent normal tissue from sample UH0210-13. FIGS. 4A-4E show the ion images obtained for the ions at m/z 788.4 (PS (18:0/18:1)), m/z 885.6 (PI (18:0/20:4)), m/z 835.6 (PI (16:0/18:1)), m/z 281.6 (FA 18:1) and m/z 537.2 (FA dimer).

Figure 4A:
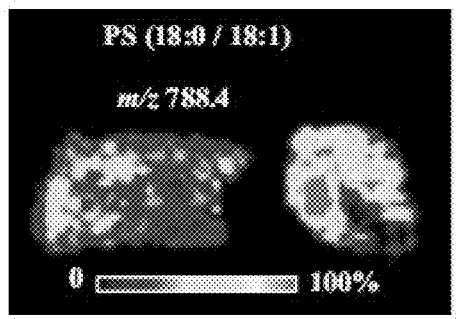
FIGS. 4A-4E show DESI-MS imaging of human bladder cancerous and adjacent normal tissue sections using morphology friendly DMF:EtOH (1:1) as the solvent system. Ion images show the distribution of m/z 788.4, PS (18:0/18:1) (FIG. 4A); m/z 885.6, PI (18:0/20:4) (FIG. 4B); m/z 835.6, PI (16:0/18:1) (FIG. 4C); m/z 281.6, FA (18:1) (FIG. 4D); and m/z 537.2 (FA dimer) (FIG. 4E).
Figure 4B:
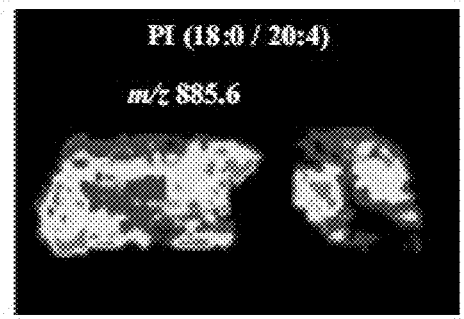
Figure 4C:
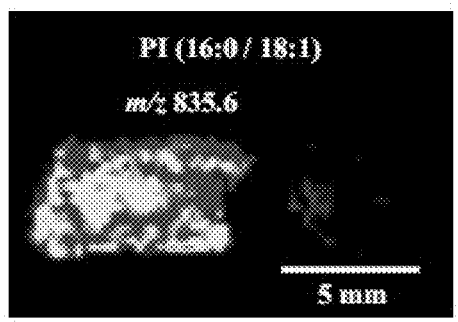
Figure 4D:
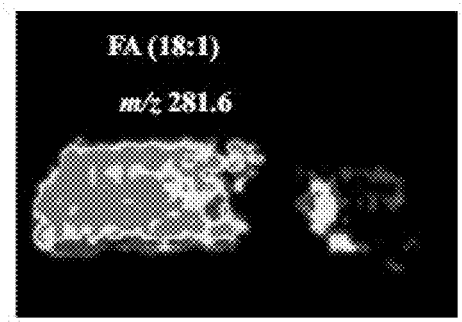
Figure 4E:
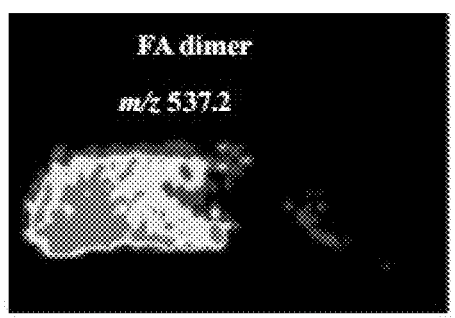

As previously reported for DESI-MS imaging of human bladder cancer in combination with statistical analysis using a standard ACN:$H_2O$ (1:1) solvent system, the ions that most significantly contribute to the discrimination between cancerous and normal bladder tissue are the free fatty acid and the fatty acid dimers, which consistently appear at increased intensities in the ion images of cancerous tissue when compared to normal tissue using the morphology friendly solvent system, DMF:EtOH (1:1) (FIGS. 4C and D; Dill A L, et al. (2011), Chemistry—a European Journal 17(10): 2897-2902; and Dill A L, et al. (2009), Analytical Chemistry 81(21):8758-8764). Representative mass spectra obtained for the cancerous and normal tissue sections are shown in FIG. 4G-H. Many other individual ions observed in the mass spectra were found at different intensities in the normal and cancerous tissues as observed in extracted DESI-MS ion images.

Figure 4F:
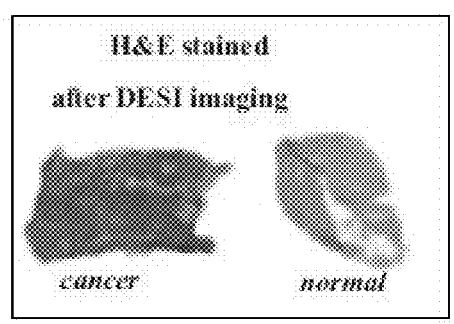
FIG. 4F shows that after the DESI-MS imaging experiment, the same tissue sections were subjected to H&E staining, evaluated by expert pathologist, and diagnosed as cancerous and normal.

The optical image of the same tissue sections stained with H&E after DESI-MS imaging analysis is shown in FIG. 4F and were used to obtain a histopathological diagnosis. Detailed pathological examination of the H&E stained sections confirmed that there was no morphological damage to the tissue sections as a result of DESI-MS imaging analysis, allowing a straightforward diagnosis of the sections as cancerous and normal. No difference in cell morphology or tissue integrity was observed at the microscopic scale when the H&E stained tissue section of the DESI-MS imaged tissue was compared to a control tissue section.

The non-destructive nature of the DMF based solvent system enables ion images to be overlaid with the H&E stain of the same tissue section for unambiguous diagnosis and correlation. For example, a small region of tissue within the cancerous section detected by DESI-MS as negative for bladder cancer based on the distribution of the FA dimer m/z 537.2 was confirmed as normal tissue by pathological evaluation of the overlaid DESI-MS ion image and H&E stain of the same tissue section. This unambiguous correlation is made possible through the use of the morphologically friendly solvent systems so that the histological data can be considered in combination with the DESI-MS imaging data. H&E stained serial sections of the same sample imaged using standard ACN:$H_2O$ (1:1) revealed that the tissue integrity was completely destroyed and were inadequate for pathological evaluation. The same histological observation that DESI imaging is histology compatible was obtained in the analysis of the H&E stained sections of five other human bladder cancer and paired normal samples, four human prostate cancer and paired normal samples and one kidney cancer and paired normal sample initially imaged by DESI-MS with a morphologically friendly solvent system.

Previously reported molecular information that allowed a diagnosis to be obtained for these types of cancer was consistent using the new solvent system. The capability of DESI-MS imaging to be histology compatible was further investigated by performing immunohistochemical (IHC) analysis with p63 antibody on bladder and prostate cancer tissue sections, which was performed after DESI-MS imaging. The gene p63 is one of the most commonly used basal cell-specific markers in the diagnosis of prostate cancer, whose expression is known to be down-regulated in adenocarcinoma of the prostate when compared to normal prostate tissue (Signoretti S, et al. (2000), American Journal of Pathology 157(6):1769-1775). Negative IHC staining of tumor protein p63 is commonly used as a clinical tool for identifying prostate cancerous tissue. The role of p63 in bladder carcinogenesis is not as clear as in prostate cancer (Comperat E, et al. (2006), Virchows Archiv 448(3):319-324), and positive staining of p63 is typically associated with both benign and malignant bladder epithelial cells.

Two bladder cancer samples and two prostate cancer samples were subjected to p63 IHC after DESI-MS imaging on the same tissue section. Detailed pathological evaluation of the tissue sections that were subjected to IHC after DESI-MS imaging confirmed that the DESI-MS analysis of the tissue lipid content did not interfere with the p63 IHC protocol, as the tissue remained intact after the imaging experiment. p63 IHC of the bladder sample was found to be positive for both cancerous and normal tissue sections. For the prostate cancer sample, UH0002-20, it was subjected to p63 IHC after DESI-MS imaging and again no damage to the morphology of the tissue was observed (FIG. 5), allowing a diagnosis of cancerous and adjacent normal tissue to be achieved, which correlated with the cholesterol sulfate signal previously reported as a possible prostate cancer biomarker using DESI-MS imaging (Eberlin L S, et al. (2010), Analytical Chemistry 82(9):3430-3434.). Also, these findings confirmed that protein position in the tissue samples remained unchanged, which is probably due to the insolubility of these proteins in the solvent combinations used.

The results reported here introduce a novel capability of histologically compatible ambient molecular imaging by DESI-MS. The feasibility of DESI-MS imaging to be performed while tissue integrity and cell morphology is conserved allows ambient mass spectrometric analysis of tissue to be combined with traditional histopathology with the goal of providing better disease diagnostics. As DESI-MS imaging using histologically friendly solvent systems does not interfere with pathological analysis, the technique could be included as the initial step in the clinical tissue analysis workflow.

Methods reported herein will allow DESI-MS to be more broadly applied in the biomedical field, such as in intraoperative applications. In additional to biomedical applications, the morphologically compatible solvent system allows DESI-MS imaging to be combined to other analytical techniques for chemical analysis of the same tissue section.

Example 2

Touch Spray for Tissue Analysis

Figure 6:
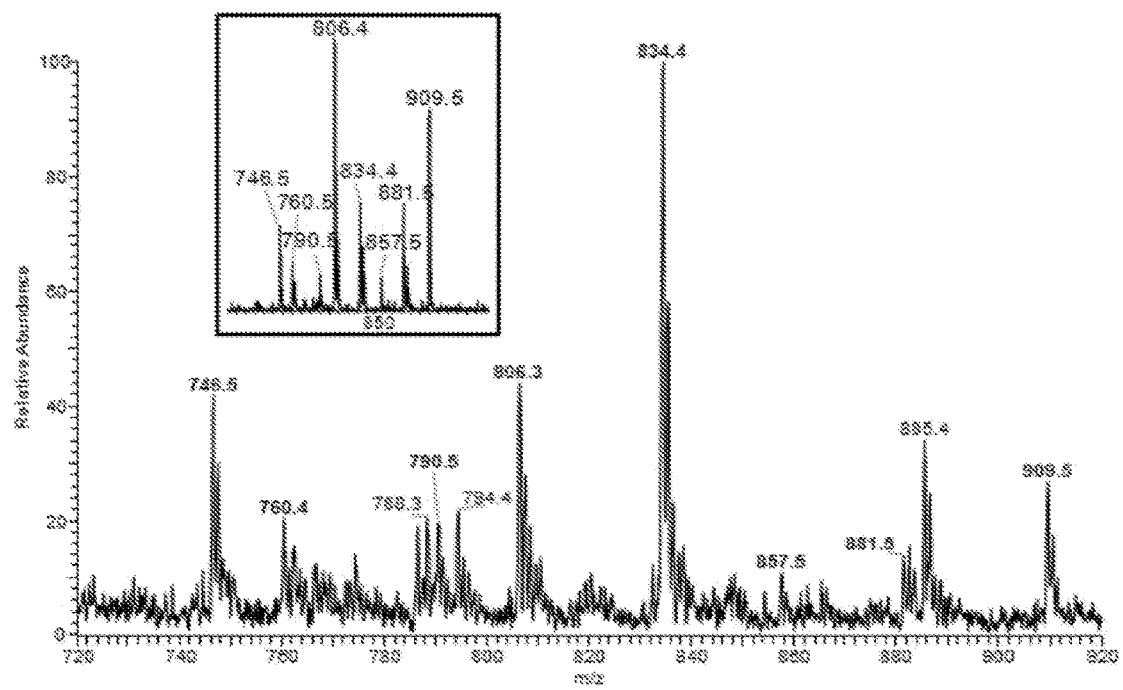
FIGS. 6-8 show brain spectra of a mouse obtained using Touch Spray.
Figure 7:
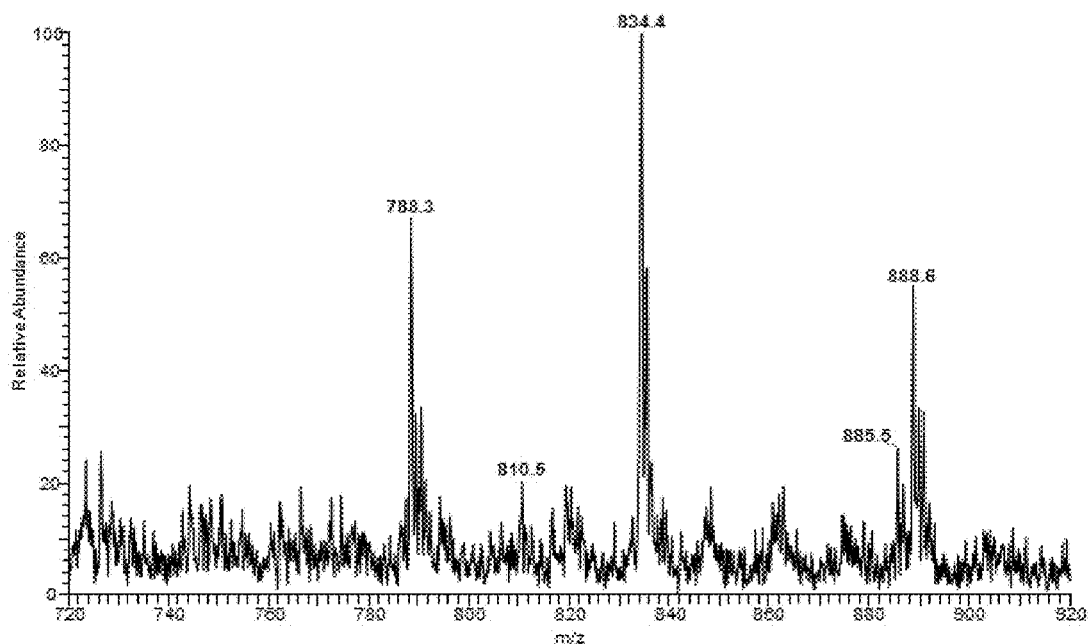
Figure 8:
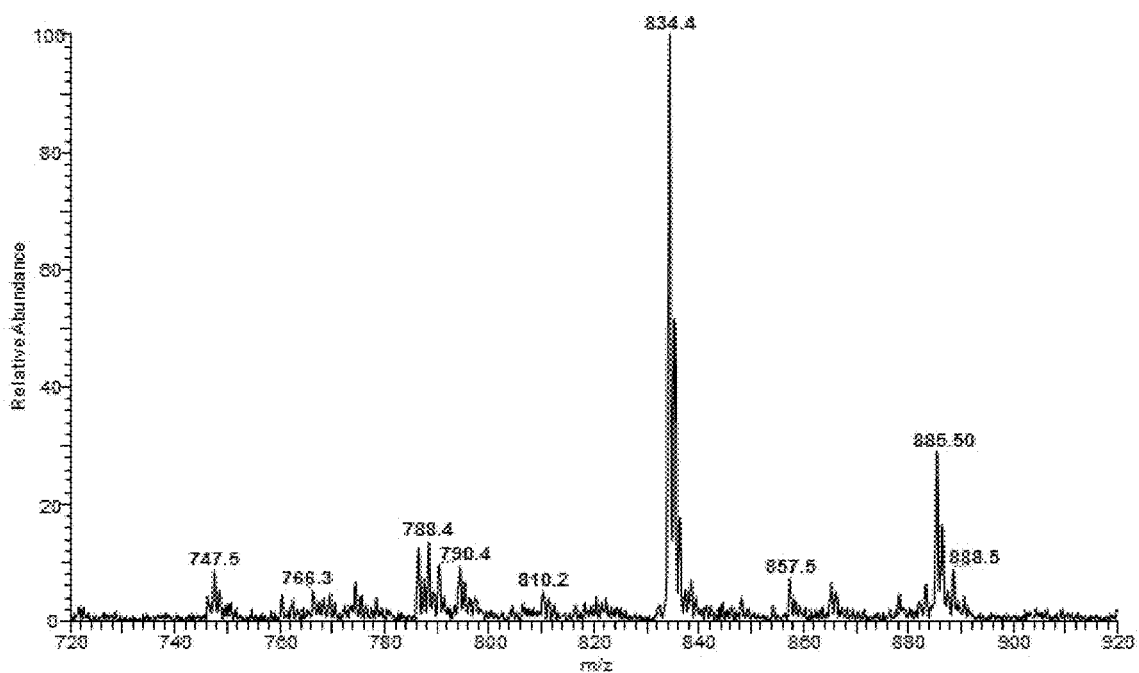

Mouse brain tissue was analyzed using Touch spray. Brain spectra of the mouse are shown in FIGS. 6-8. The spectrum in FIG. 7 represents a typical spectrum obtained when probing the G1 region of a mouse brain. The insert on FIG. 6 is the spectrum shown in the 3D mouse brain using DESI. Although the relative intensities of the peaks differ between the two methods, the pattern between the DESI spectrum and the Touch Spray spectrum is very similar. FIG. 8 shows a typical spectrum seen when probing white matter, same section as G1 touch experiment.

Figure 9:
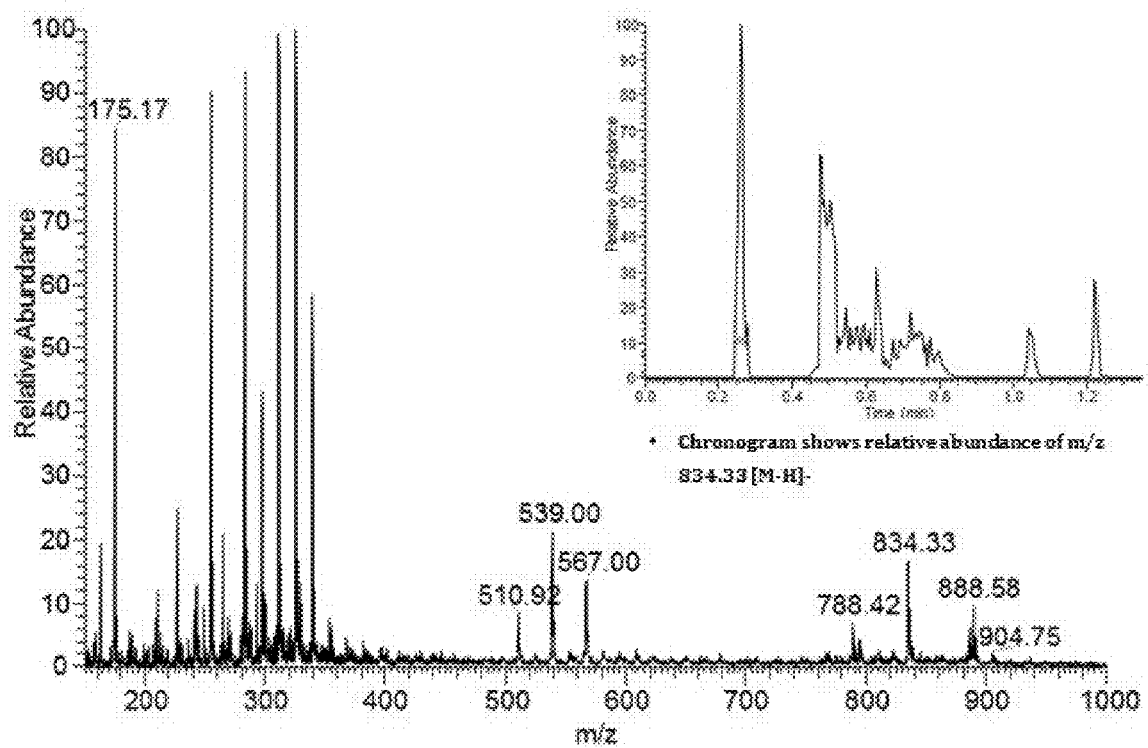
FIGS. 9-10 shows additional spectra of mouse brain.
Figure 10:
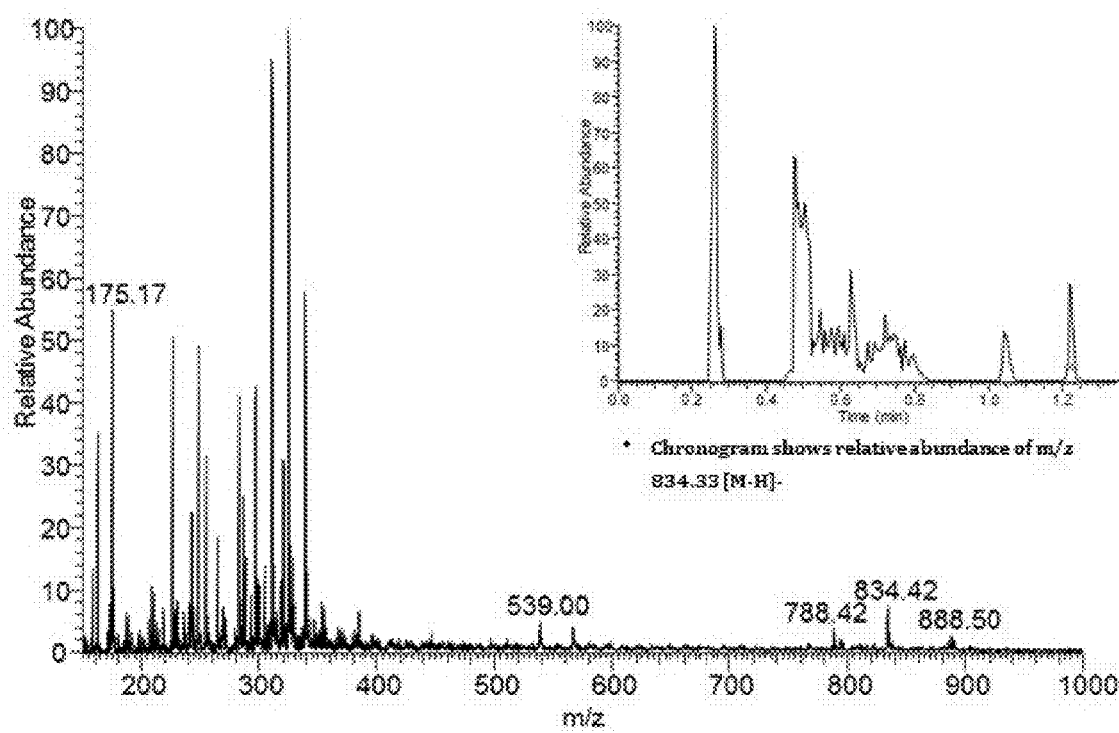

FIGS. 9-10 shows additional spectra of mouse brain obtained using Touch Spray.

Example 3

Touch Spray for Metabolite Detection

Figure 11:
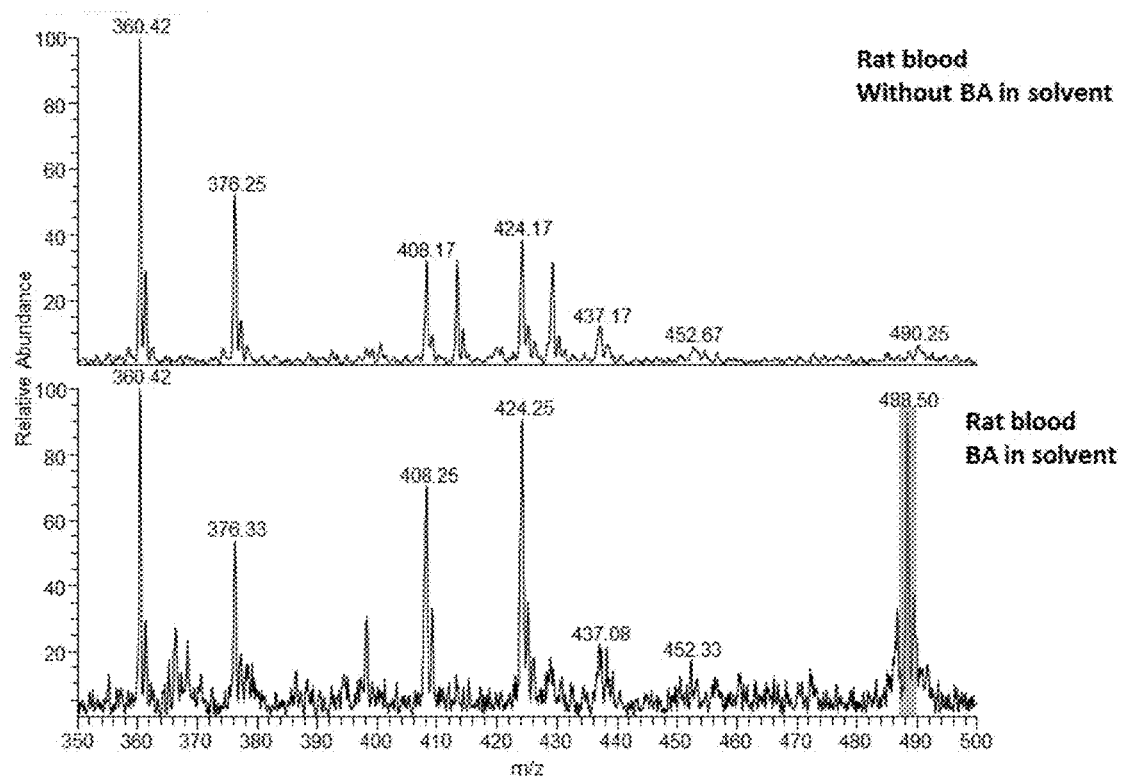
FIG. 11 shows spectra obtained using Touch Spray from dip experiments on rat blood. The top spectrum was obtained using ACN as the spray solvent and the bottom was obtained using an ACN solution with 10 ppm betaine aldehyde. The BA-cholesterol product, m/z 488.5, is clearly seen in the bottom spectrum.

FIG. 11 shows spectra obtained using Touch Spray from dip experiments on rat blood. The top spectrum was obtained using ACN as the spray solvent and the bottom was obtained using an ACN solution with 10 ppm betaine aldehyde. The BA-cholesterol product, m/z 488.5, is clearly seen in the bottom spectrum.

Figure 12:
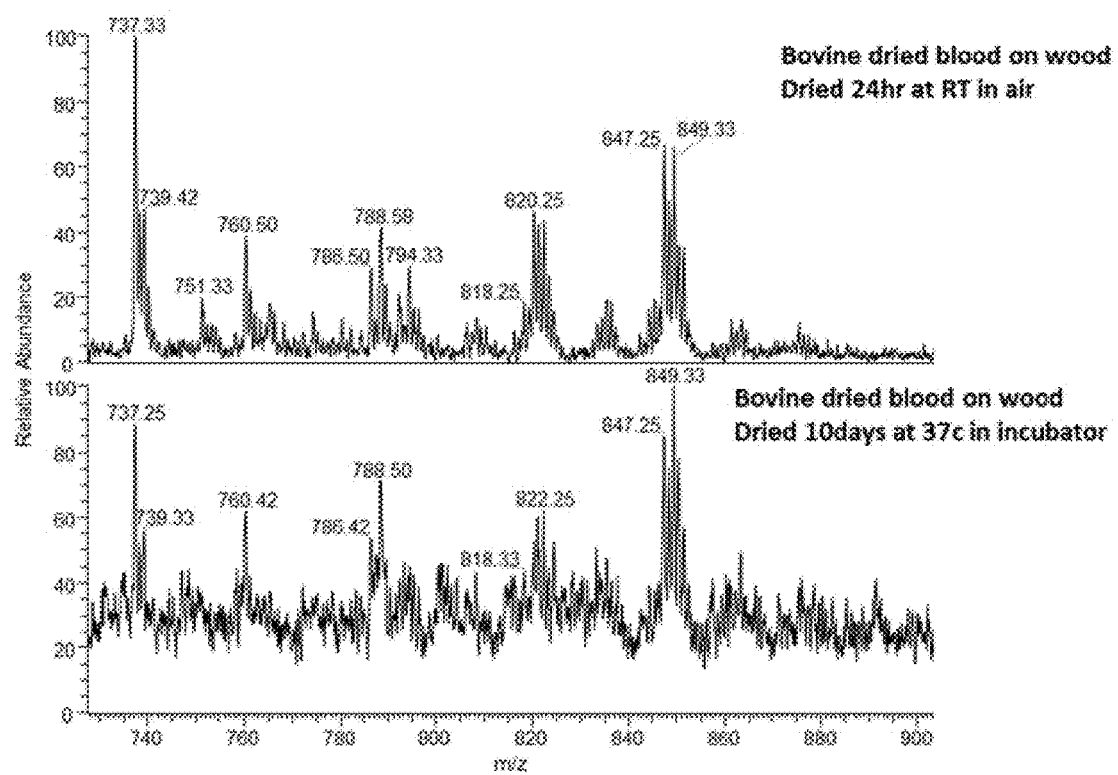
FIG. 12 shows spectra obtained using Touch Spray from dried bovine blood spots (5 uL) on wood using a methanol wetted teasing probe. The top spectrum was taken after drying the bovine blood on wood for 24 hr at room temperature in open air. The bottom spectrum was taken after drying the bovine blood on wood for 10 days at 37 c in an incubator.

FIG. 12 shows spectra obtained using Touch Spray from dried bovine blood spots (5 uL) on wood using a methanol wetted teasing probe. The top spectrum was taken after drying the bovine blood on wood for 24 hr at room temperature in open air. The bottom spectrum was taken after drying the bovine blood on wood for 10 days at 37° C. in an incubator. The phospholipid pattern seen from the blood spot dried for 10 days at 37° C. still matches up quite well to that of the blood spot dried for 24 hr.

Figure 13:
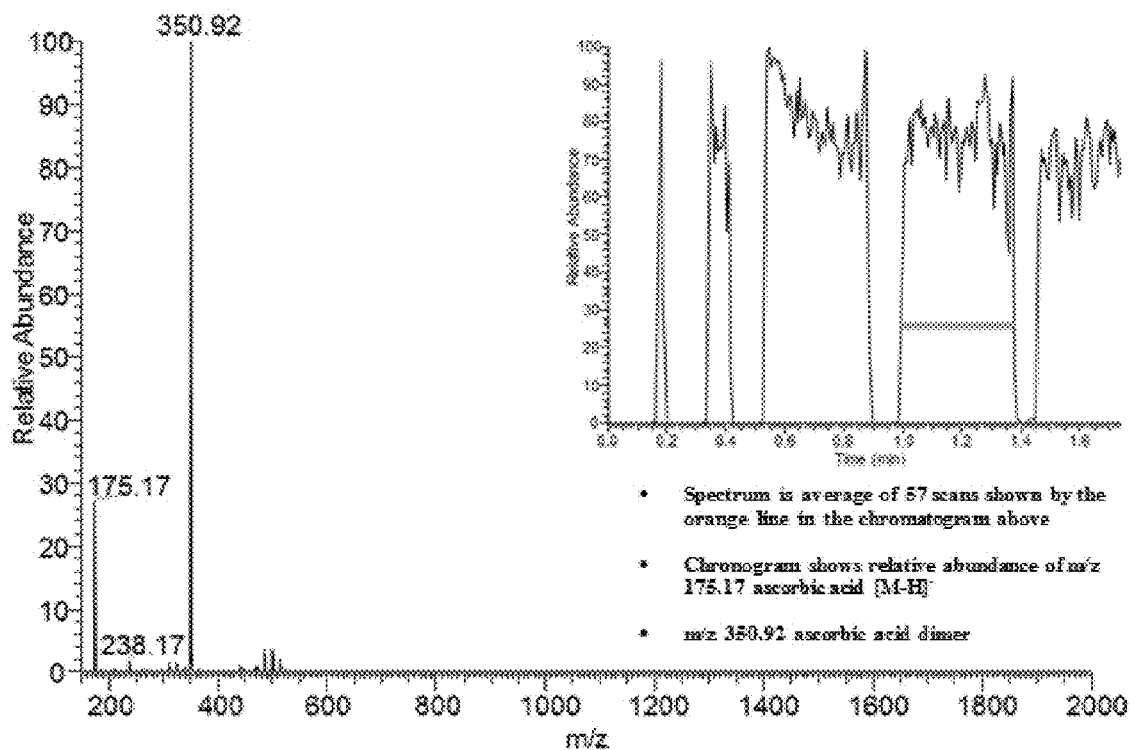
FIG. 13 shows a spectrum of ascorbic acid detected using Touch Spray.

FIG. 13 shows a spectrum of ascorbic acid detected using touch spray.

Example 4

Touch Spray Using a Dry Probe

All touch spray experiments on tissue in this example were performed using a dry probe and then spraying methanol. The spectra are from mouse brain, prostate specimen, and reactive touch spray. Reaction experiments were done by dipping the touch spray probe into a solution mixture of cholesterol, cholesteryl linoleate, and adrenosterone and then spraying with a specific reagent.

Figure 14:
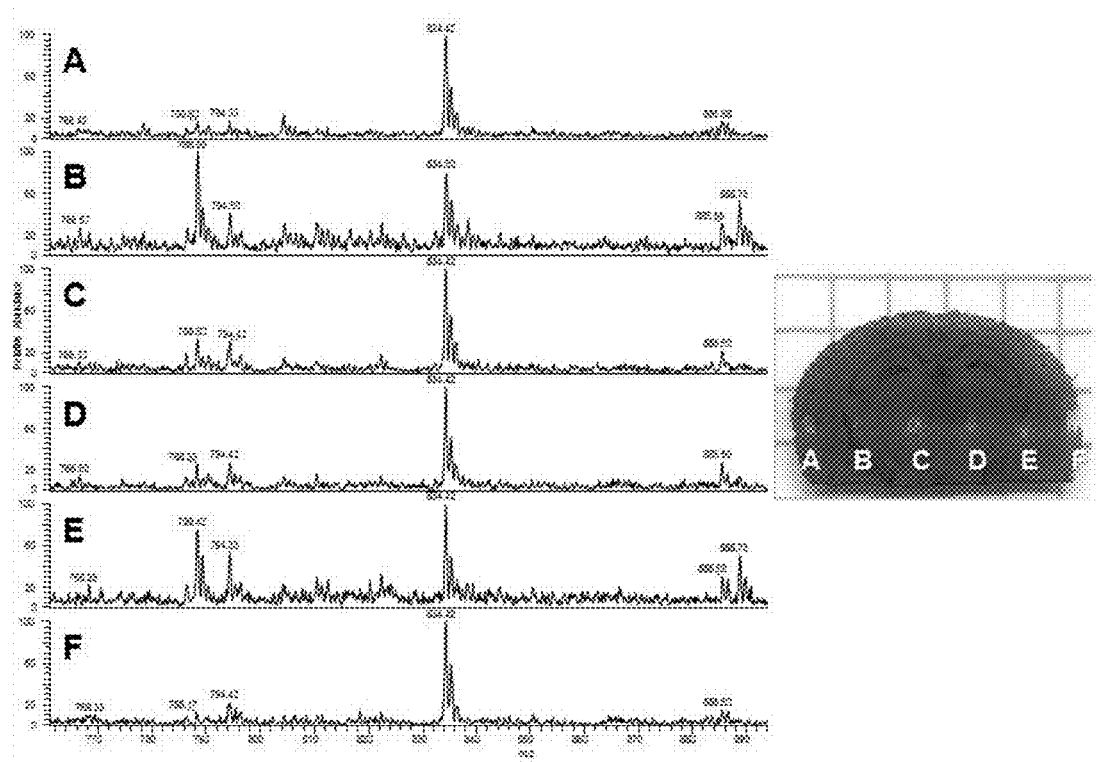
FIG. 14 shows spectra from a mouse brain line scan.

FIG. 14 shows spectra from a mouse brain line scan.

Figure 15:
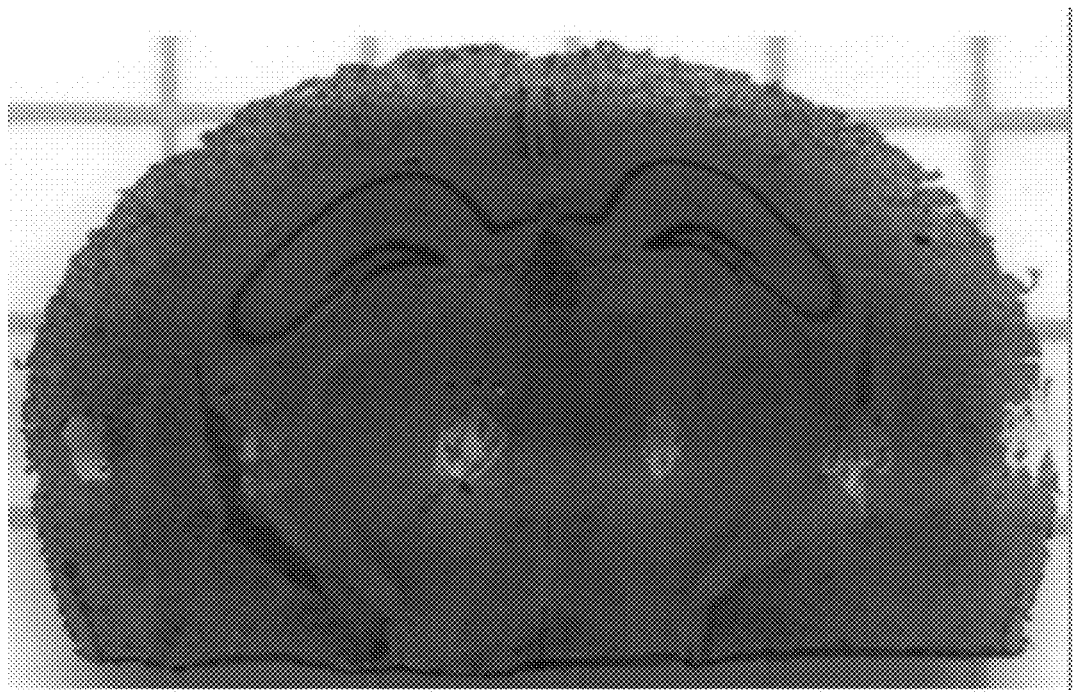
FIG. 15 is a zoom of the mouse brain H&E to increase visibility of the touched regions. Boxes are about 2 mm×2 mm.

FIG. 15 is a zoom of the mouse brain H&E to increase visibility of the touched regions.

Boxes are about 2 mm×2 mm.

Figure 16:
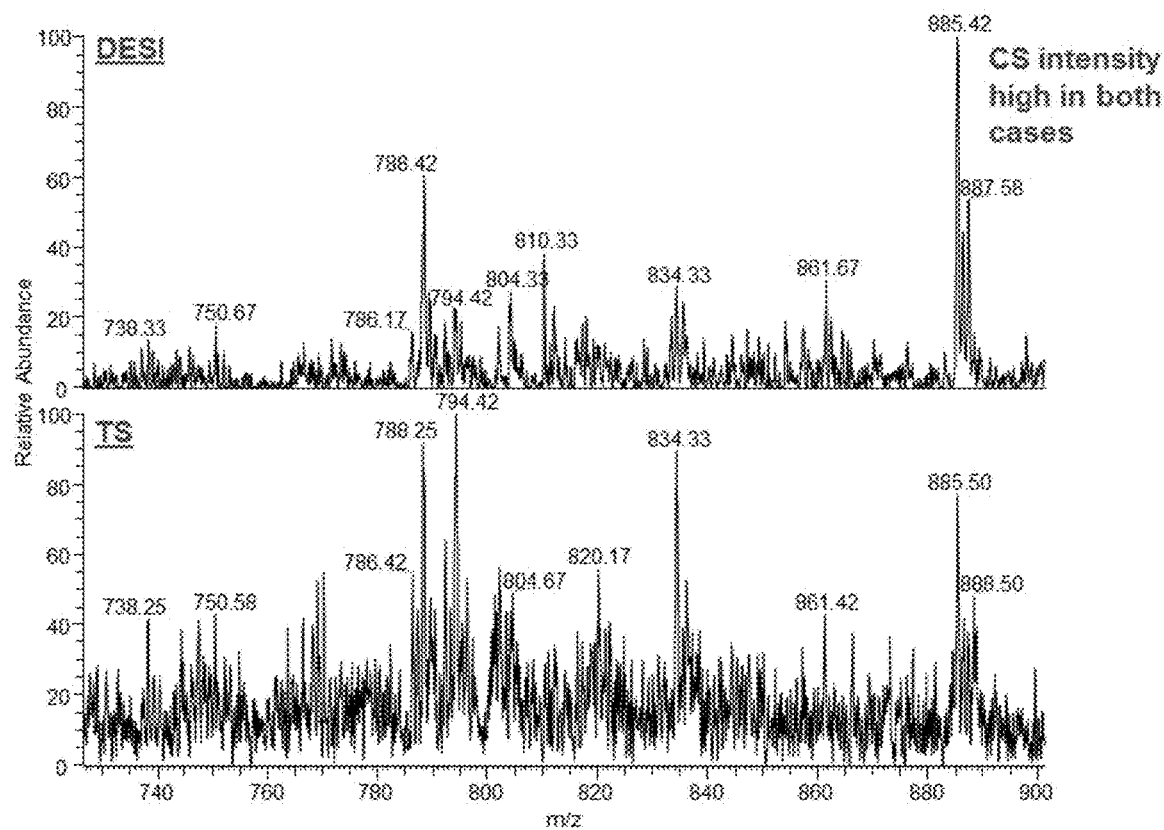
FIG. 16 spectra show the phospholipid m/z region of tumor tissue from radical prostatectomy case S13-2011 biopsy number 6 produced by DESI and TS respectively. Two adjacent sections confirm tumor region of the tissue.

FIG. 16 spectra show the phospholipid m/z region of tumor tissue from radical prostatectomy case S13-2011 biopsy number 6 produced by DESI and TS respectively. Two adjacent sections confirm tumor region of the tissue.

Figure 17:
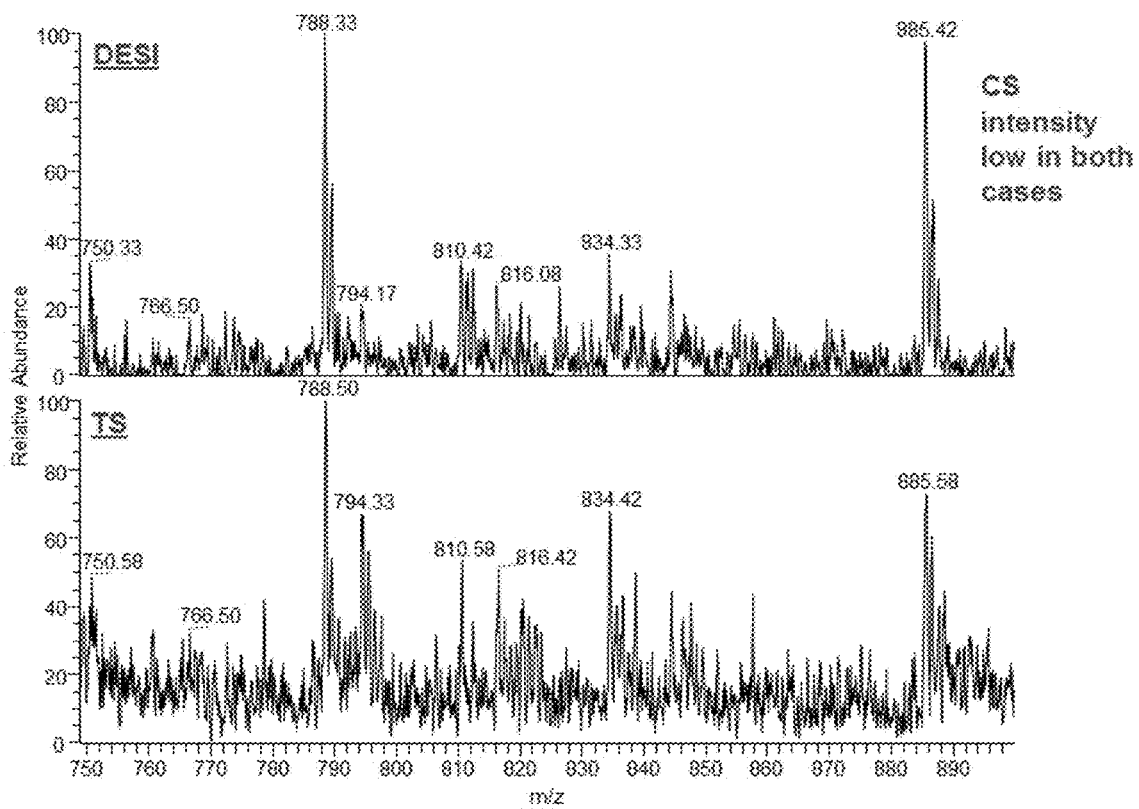
FIG. 17 show data acquired from the adjacent normal tissue region of biopsy number 6.

FIG. 17 show data acquired from the adjacent normal tissue region of biopsy number 6.

Figure 18:
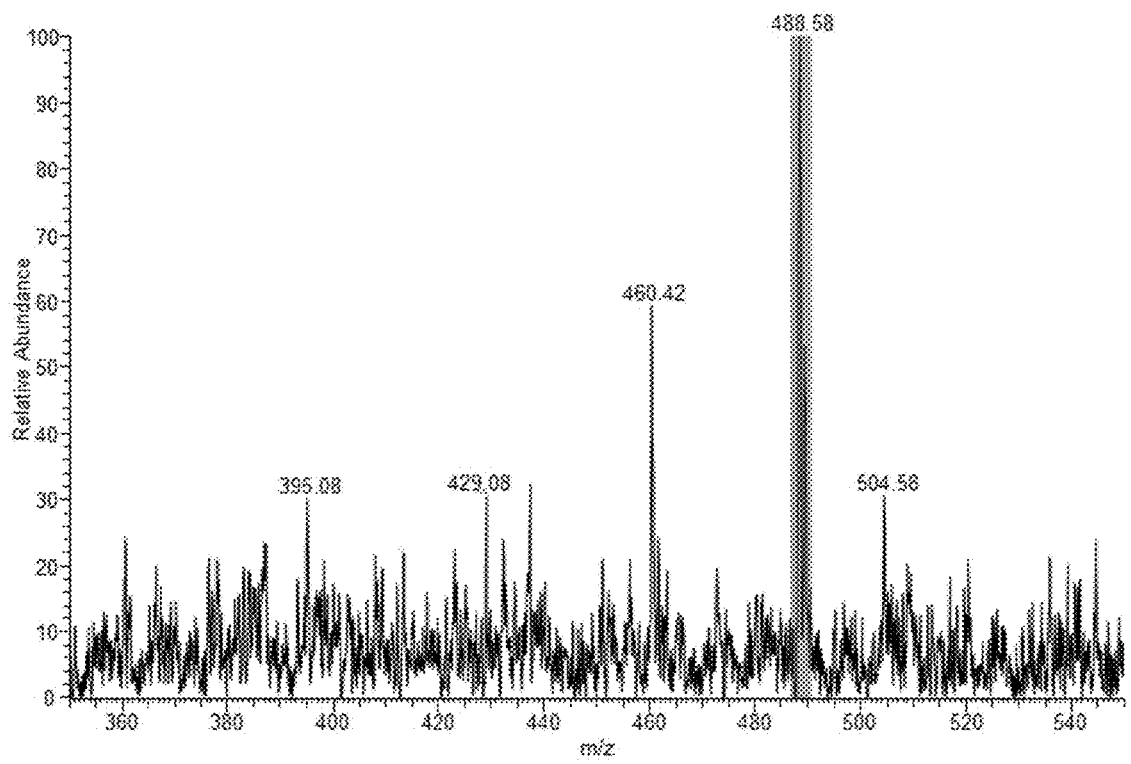
FIG. 18 shows Betaine aldehyde (10 ppm) reaction with cholesterol (100 ppm)—product m/z 488.5 positive mode.

FIG. 18 shows Betaine aldehyde (10 ppm) reaction with cholesterol (100 ppm)—product m/z 488.5 positive mode.

Figure 19:
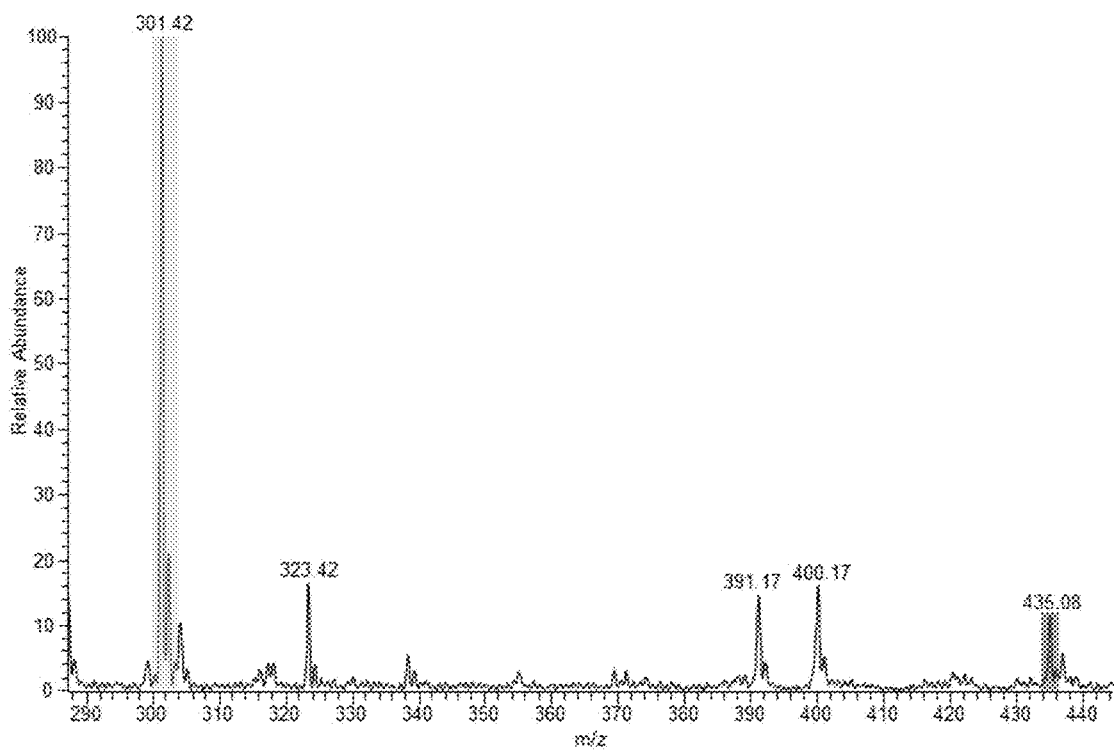
FIG. 19 shows Girard's reagent P (few ppm) reaction with adrenosterone (10 ppm)—product m/z 435.08 positive mode. m/z 301 is adrenosterone (precursor), FIG. 20 Silver (4 ppm) adduct on cholesteryl linoleate (10 ppm)—m/z 755.4 and 757.4. Also not reported. At 10 ppm cholesteryl linoleate did not show up in the full scan in positive or negative mode.
Figure 20:
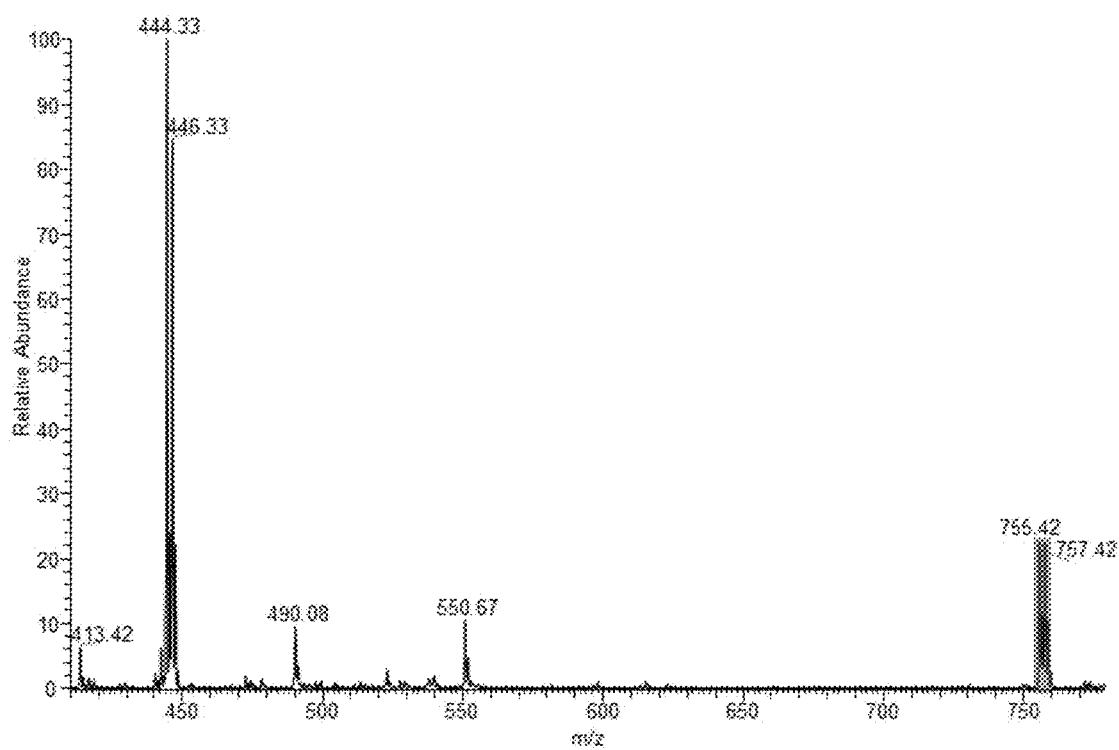

FIG. 19 shows Girard's reagent P (few ppm) reaction with adrenosterone (10 ppm)—product m/z 435.08 positive mode. m/z 301 is adrenosterone (precursor), FIG. 20 Silver (4 ppm) adduct on cholesteryl linoleate (10 ppm)—m/z 755.4 and 757.4. Also not reported. At 10 ppm cholesteryl linoleate did not show up in the full scan in positive or negative mode.

Figure 21:
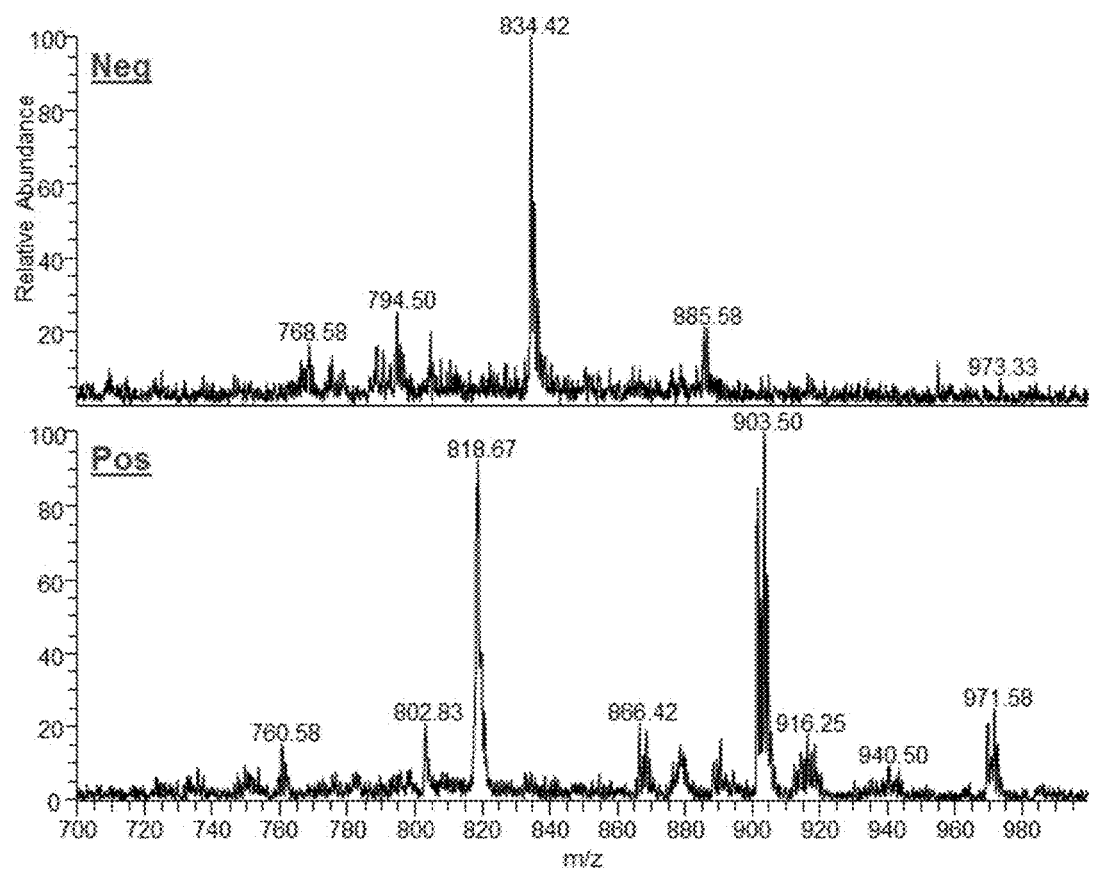
FIG. 21 Mouse Brain positive mode (typical spectrum seen for grey matter) and mouse brain positive mode using silver nitrate solution (4 ppm) in ACN as spray solvent (m/z 901 and 903 are Ubiquinone q9 and m/z 969 and 971 are Ubiquinone q10, there may be some TAGs as well)

FIG. 21 Mouse Brain positive mode (typical spectrum seen for grey matter) and mouse brain positive mode using silver nitrate solution (4 ppm) in ACN as spray solvent (m/z 901 and 903 are Ubiquinone q9 and m/z 969 and 971 are Ubiquinone q10, there may be some TAGs as well).

Example 5

Touch Spray for Bacteria

Figure 22:
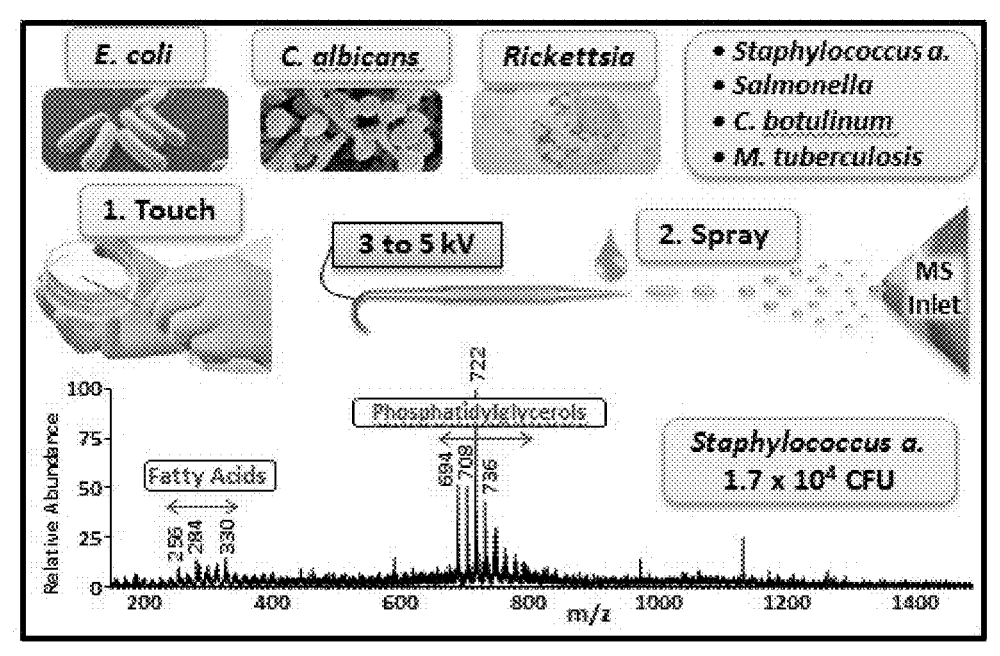

FIG. 22 shows a workflow for analyzing bacteria using Touch Spray. The workflow shows that a probe tip is touched to an agar plate having cultured bacteria. The probe may be swabbed or moved in any manner over the plate. The probe is then removed from the plate and solvent and voltage are applied to the probe so that ions are generated that go into a mass spectrometer for analysis.

Example 6

Touch Spray for Analyzing Biofluids

Figure 23:
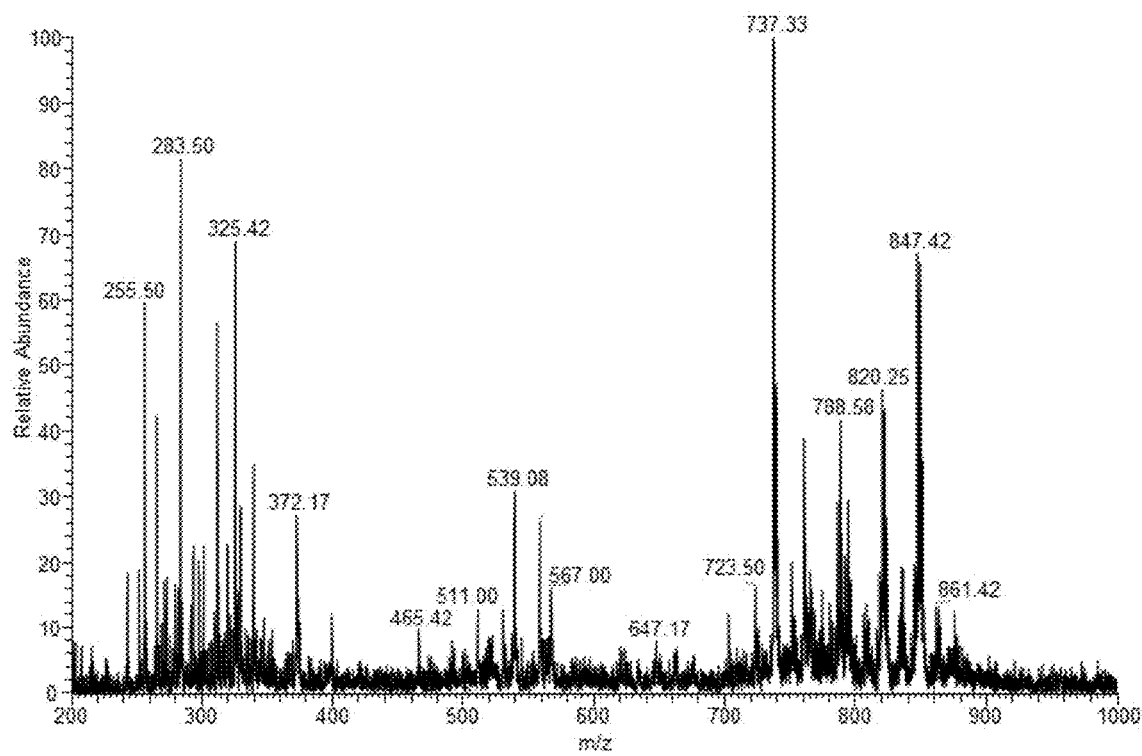
FIG. 23 shows a negative-mode spectrum obtained from a dried 5 uL bovine blood spot off of wood.

FIG. 23 shows a negative-mode spectrum obtained from a dried 5 uL bovine blood spot off of wood. This dried blood spot was dried for 24 hours in the fume hood. Methanol was used to wet the teasing probe to touch the dried blood spot.

The probe was allowed to dry and then used pure methanol to spray. m/z 810 peak is a very complex set of phospholipids.

Figure 24:
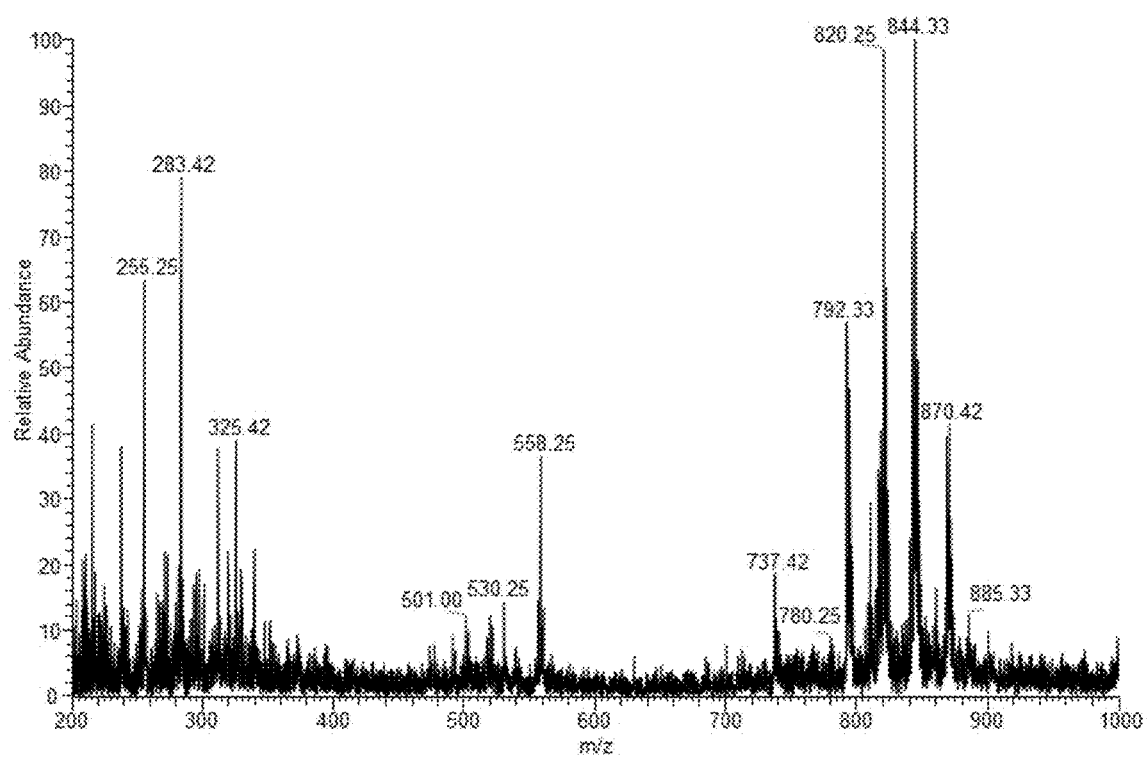
FIG. 24 shows a negative-mode spectrum obtained from a dried 5 uL canine blood spot off of glass.

FIG. 24 shows a negative-mode spectrum obtained from a dried 5 uL canine blood spot off of glass. Dry time was about ~20-30 minutes. Again a methanol wetted teasing probe was used to touch the dried blood spot, probe was dried, and then pure methanol was used to spray. Again m/z 810 was not seen to dominate the PL region, but it is interesting to note that the bovine and canine blood spectra are significantly different than each other.

Figure 25:
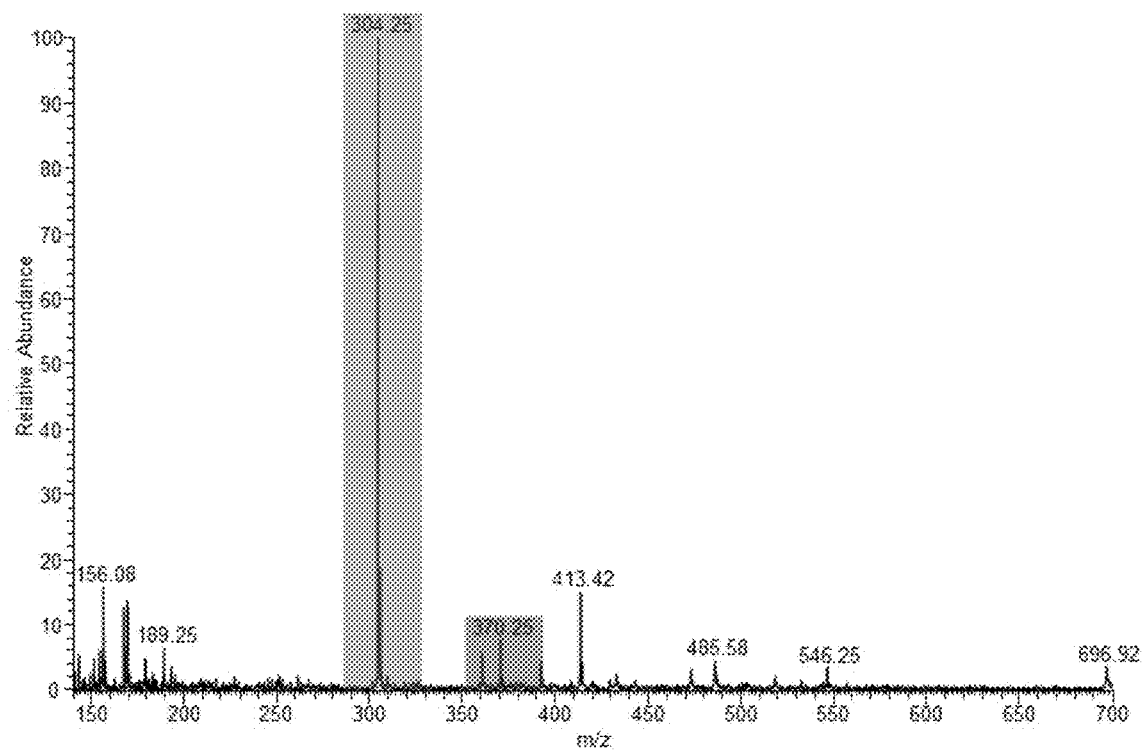
FIG. 25 shows a positive-mode spectrum obtained from doing a dip experiment with the teasing probe into some spiked blood.

FIG. 25 shows a positive-mode spectrum obtained from doing a dip experiment with the teasing probe into some spiked blood. The spiked bovine blood had final concentrations of 10 ppm for both cocaine and heroin. The dry teasing probe was dipped into a 10 uL sample of the fresh wet blood, allowed to dry after dipping, and pure methanol was used as the spray solvent.

Figure 26:
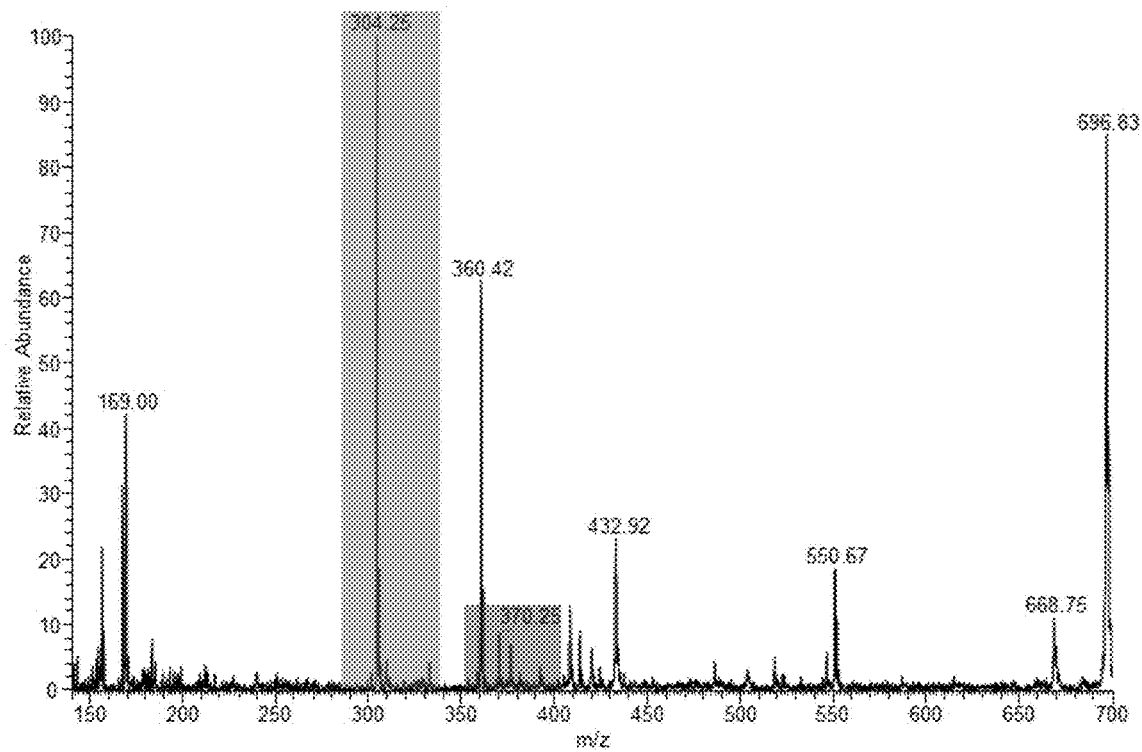
FIG. 26 shows a positive-mode spectrum obtained from a dry spiked bovine blood spot on glass.

FIG. 26 shows a positive-mode spectrum obtained from a dry spiked bovine blood spot on glass. 5 uL of the 10 ppm cocaine and heroin blood sample was dried on a glass slide, which should be 50 ng of each drug. A methanol wetted teasing probe was used to extract the sample off the glass and pure methanol was used to spray.

Example 7

Touch Spray for Margin Detection in Tissue

Figure 27:
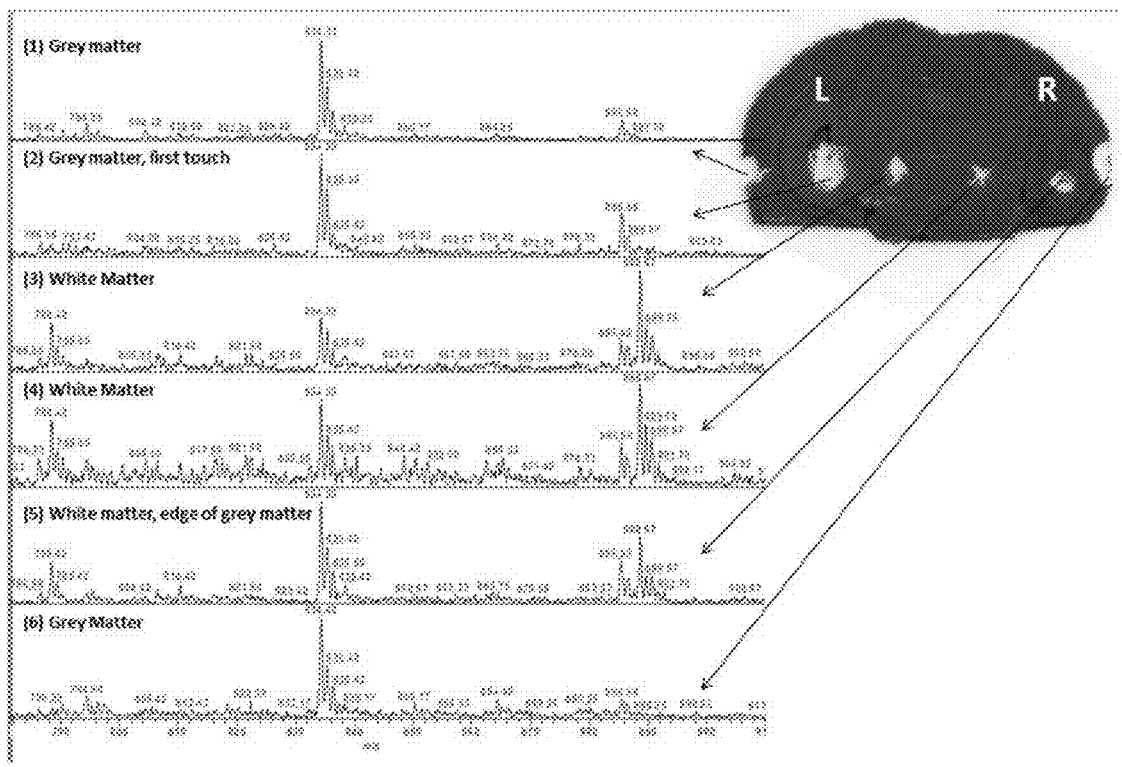
FIG. 27 shows spectrum of white and grey tissue matter in a mouse brain.

FIG. 27 shows spectrum of white and grey tissue matter in a mouse brain. The data show that touch spray can differentiate different areas of the brain, grey matter vs white matter, by doing a "line scan" across the mouse brain. A teasing probe was used to investigate the brain tissue every ~1.5 mm, except for the second spot which was repeated. It is clear which spectrum corresponds to white matter and which spectrum corresponds to grey matter based on the change in m/z 885 vs m/z 888 relative abundances. The only spectrum that may not be so clear cut is number 5 where m/z 885 and 888 peaks are much closer to a 1:1 ratio than the other white matter spectra shown. It is interesting to note that spectrum number 5 was taken from the right side of the brain which should pretty much be a mirror image of the left side, but in this mouse brain section it is clearly not. This leads us to believe that spectrum number five represents data obtained from the margin of some grey and white matter, which seems plausible based on the H&E stain also attached. Note that each of the touched areas are about 750 microns in diameter, except for the 2nd one of course.

Example 8

Touch Spray for Uterine and Prostate Tissue

Figure 28:
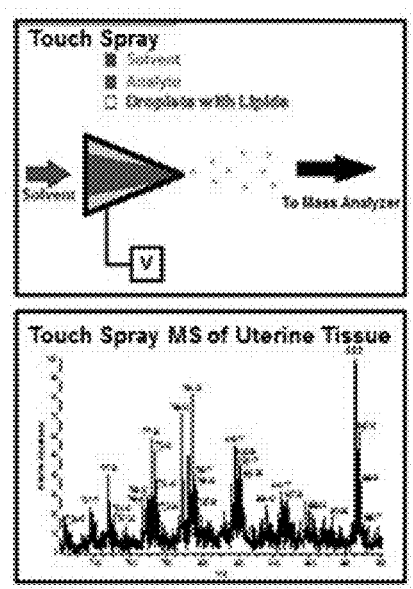
FIG. 28 illustrates the result of a spray MS taken using a hypodermic needle to probe the surface of human uterine tissue.
Figure 29:
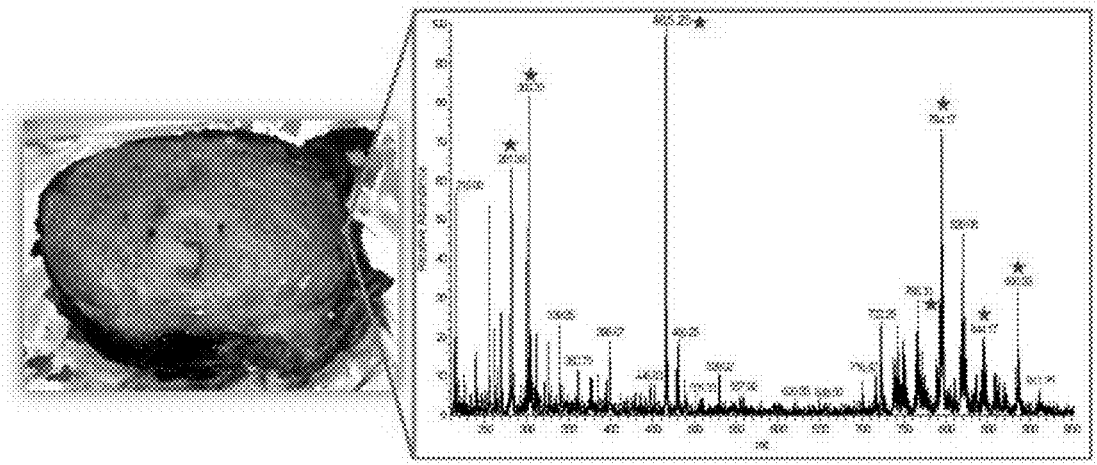
FIG. 29 demonstrate Touch Spray on prostate tissue.

Touch Spray has been demonstrated in uterine tissue. FIG. 28 illustrates the result of a spray MS taken using a hypodermic needle to probe the surface of human uterine tissue. Likewise, data shown in FIG. 29 demonstrate Touch Spray on prostate tissue. The data show MS lipid profiles consistent with those obtained in previous studies with DESI-MS.

Example 9

Metabolite Level Correlation to its Originating Source

For many intraoperative decisions, surgeons depend on frozen section pathology, a technique developed over 150 years ago. Technical innovations that permit rapid molecular characterization of tissue samples at the time of surgery are needed. Here, using desorption electrospray ionization mass spectrometry (DESI MS), the tumor metabolite 2-hydroxyglutarate (2-HG) was rapidly detected from tissue sections of surgically-resected gliomas, under ambient conditions and without complex or time-consuming preparation. With DESI MS, IDH1-mutant tumors were identified with both high sensitivity and specificity within minutes, immediately providing critical diagnostic, prognostic and predictive information. Imaging tissue sections with DESI-MS shows that the 2-HG signal fully overlaps with areas of tumor and that 2-HG levels correlate with tumor content, thereby indicating tumor margins. Mapping the 2-HG signal onto three-dimensional MRI reconstructions of tumors allows the integration of molecular and radiologic information for enhanced decision making. Data herein show that metabolite-imaging mass spectrometry can transform many aspects of surgical care.

Introduction

The review of tissue sections by light microscopy remains a cornerstone of tumor diagnostics. In recent decades, monitoring expression of individual proteins using immunohistochemistry and characterizing chromosomal aberrations, point mutations and gene expression with genetic tools has further enhanced diagnostic capabilities. These ancillary tests, however, often require days to weeks to perform and the results become available long after surgery is completed. For this reason, the microscopic review of tissue biopsies frequently remains the sole source of intraoperative diagnostic information, with many important surgical decisions based on this information. This approach is time consuming, requiring nearly 30 minutes between the moment a tissue is biopsied and the time the pathologist's interpretation is communicated back to the surgeon. Tools that provide immediate feedback to the surgeon could transform the way surgery is performed.

Mass spectrometry offers the possibility for the in-depth analysis of the proteins and lipids that comprise tissues. The ionization profile of lipids within tumors can be used for classifying tumors and for providing valuable prognostic information such as tumor subtype and grade. Because DESI-MS is performed in ambient conditions with minimal pretreatment of the samples (Wiseman et al., Nat Protoc 3, 517-524 (2008); and Takats et al., Science 306, 471-473 (2004)), diagnostic information could be provided rapidly within the operating room (Agar et al., Neurosurgery 68, 280-289; discussion 290 (2011); and Eberlin et al., Proc Natl Acad Sci USA (2013)). The ability to quickly acquire such valuable diagnostic information from lipids made us wonder whether we could use DESI MS to detect additional molecules of diagnostic value within tumors such as their metabolites.

Recently, recurrent mutations have been described in the genes encoding isocitrate dehydrogenases 1 and 2 (IDH1 and IDH2) in a number of tumor types including gliomas (Parsons et al., Science 321, 1807-1812 (2008)), intrahepatic cholangiocarcinomas (Borger et al., Oncologist 17, 72-79 (2012)), acute myelogenous leukemias (AML) (Mardis et al., N Engl J Med 361, 1058-1066 (2009)) and chondrosarcomas (Amary et al., J Pathol 224, 334-343 (2011)). These mutant enzymes have the novel property of converting α-ketoglutarate to 2-hydroxyglutarate (2-HG) (Dang et al., Nature 462, 739-744 (2009)). This oncometabolite has pleiotropic effects on DNA methylation patterns (Lu et al., Nature 483, 474-478 (2012); Turcan et al., Nature 483, 479-483 (2012); and Xu et al., Cancer Cell 19, 17-30

(2011)), on the activity of prolyl hydroxylase (Koivunen et al. Nature 483, 484-488 (2012)) and on cellular differentiation and growth (Wang et al., Science (2013); Rohle, et al., Science (2013); and Losman et al., Science (2013)). While 2-HG is present in vanishingly small amounts in normal tissues, concentrations of several micromoles per gram of tumor have been reported in tumors with mutations in IDH1 and IDH2 (Dang et al., Nature 462, 739-744 (2009)). It has been reported that 2-HG can be detected by magnetic resonance spectroscopy and imaging hence providing a non-invasive imaging approach for evaluating patients (Lazovic et al., Neuro Oncol 14, 1465-1472 (2012); Andronesi, Sci Transl Med 4, 116ra114 (2012); Choi, Nat Med 18, 624-629 (2012); Elkhaled, et al., Sci Transl Med 4, 116ra115 (2012); Guo, et al., Acta Neurochir (Wien) 154, 1361-1370; discussion 1370 (2012); Kalinina et al., J Mol Med (Berl) 90, 1161-1171 (2012); and Pope et al., J Neurooncol 107, 197-205 (2012)). While such imaging approaches can provide information to plan surgery and to follow the response to chemotherapeutics, applying them to guide decision-making during an operation is currently impractical.

The data herein show that 2-HG can be rapidly detected from glioma samples using DESI MS under ambient conditions and without complex tissue preparation. Standard pathology techniques were used to cross-validate the data. Measuring specific metabolites in tumor tissues with precise spatial distribution and under ambient conditions provides a new paradigm for intraoperative surgical decision-making.

Materials and Methods

Tissue Samples:

The tissue samples used in this example were obtained from the BWH Neurooncology Program Biorepository collection as previously described (Eberlin et al., Cancer Res 72, 645-654 (2012)). They were obtained and analyzed under Institutional Review Board protocols approved at BWH. Informed written consent was obtained by neurosurgeons at BWH. The samples were sectioned for DESI MS analysis as previously described (Eberlin et al., Cancer Res 72, 645-654 (2012)). The tumors were classified in accordance with the WHO classification system. Resections of brain tumor lesions were performed using neuronavigation, with stereotactic mapping and spatial registering of biopsies performed as previously described (Agar et al., Neurosurgery 68, 280-289; discussion 290 (2011)). 3D-reconstruction of the tumor from MRI imaging data was achieved with 3-dimensional Slicer software package (Elhawary et al., Neurosurgery 68, 506-516; discussion 516 (2011)).

Histopathology and Immunohistochemistry:

In addition to banked snap frozen samples, all cases had tissue samples that were formalin-fixed and paraffin embedded. Sections of FFPE tissue were stained with an anti-isocitrate dehydrogenase 1 (IDH1)-R132H antibody (clone HMab-1 from EMD Millipore) as previously described (Capper et al., Brain Pathol 20, 245-254 (2010)). Tissues were sectioned and immunostained as previously described (Eberlin et al., Cancer Res 72, 645-654 (2012)). Hematoxylin and eosin (H&E) stained serial tissue sections were scanned using Mirax Micro 4SL telepathology system from Zeiss to generate digital optical images. Tumor content was evaluated by board-certified neuropathologists (S.S. and K.L.L.) through examination of H&E stained tissue sections and IDH1 R132H stained sections.

Identification of 2-Hydroxyglutarate by DESI MS:

The IDH1 status of each specimen was initially evaluated by IHC of a piece of FFPE tissue. For stereotactic cases, all biopsies were less than 0.4 cm and these specimens were divided in two (one portion was frozen for DESI MS studies and the other was processed for FFPE; the latter was used for IDH1 IHC).

To determine if 2-HG could be detected directly from glioma tissue sections by DESI MS, we analyzed human glioma samples by DESI MS in the negative ion mode using either an LTQ Ion Trap (Thermo Fisher Scientific, San Jose, Calif., USA) or an amaZon speed ion trap (Bruker Daltonics, Billerica, Mass.). The solvent used in these experiments consisted of either MeOH:H$_2$O (1:1) or ACN:DMF (1:1) with a mass from m/z 100-1100. All experiments involving the amaZon speed ion trap were carried out using a 5 kV spray voltage, 130 psi nebulizing gas (N2) and a flow rate of 0.7 μL/min.

A description of the samples used in this study (analyzed with the LTQ Ion Trap) is shown in Table 1.

TABLE 1

Detailed description of samples used in IDH1 study. IHC and DESI results are shown.

| Sample ID | Diagnosis | % tumor | IHC IDH1 R132H | Normalized m/z 147 | 2-HG |
|---|---|---|---|---|---|
| Low tumor cell concentration ||||||
| G10 | O-II | 30 | positive | 12 | positive |
| G22 | O-II | 10 | positive | 9 | positive |
| G25 | O-II | 20 | positive | 72 | positive |
| G40 | O-II | 5 | positive | 45 | positive |
| G13 | OA-II | 5 | positive | 11 | positive |
| G14 | OA-II | 40 | positive | 47 | positive |
| G9 | O-II/III | 50 | positive | 44 | positive |
| G11 | O-II/III | 20 | positive | 79 | positive |
| G20 | OA-III | 30 | positive | 16 | positive |
| G26 | A-IV | 20 | positive | 52 | positive |
| G47 | A-IV-O | 5 | positive | 30 | positive |
| High tumor cell concentration ||||||
| G2 | A-II | 60 | positive | 74 | positive |
| G49 | O-II | 100 | positive | 87 | positive |
| G42 | O-II | 90 | positive | 148 | positive |
| G43 | O-II | 80 | positive | 241 | positive |
| G41 | O-III | 95 | positive | 178 | positive |
| G23 | O-III | 95 | positive | 215 | positive |
| G21 | OA-III | 95 | positive | 247 | positive |
| G45 | OA-III | 100 | positive | 79 | positive |
| G30 | A-IV-O | 80 | positive | 48 | positive |
| G46 | A-IV | 90 | ND | 62 | positive |
| IDH wild type by IHC ||||||
| G3 | A-III | 60 | negative | 10 | negative |
| G4 | A-III | 30 | negative | 6 | negative |
| G5 | A-IV-O | 80 | negative | 29 | negative |
| G6 | A-IV | 80 | negative | 12 | negative |
| G8 | A-IV | 90 | negative | 10 | negative |
| G27 | A-IV | 95 | negative | 16 | negative |
| G28 | A-IV | 80 | negative | 126 | positive |
| G29 | A-IV-O | 80 | negative | 25 | negative |
| G31 | A-IV | 90 | negative | 17 | negative |
| G32 | A-IV | 90 | negative | 15 | negative |
| G33 | A-IV | 80 | negative | 41 | positive |
| G34 | A-IV | 30 | negative | 8 | negative |

Figure 30:
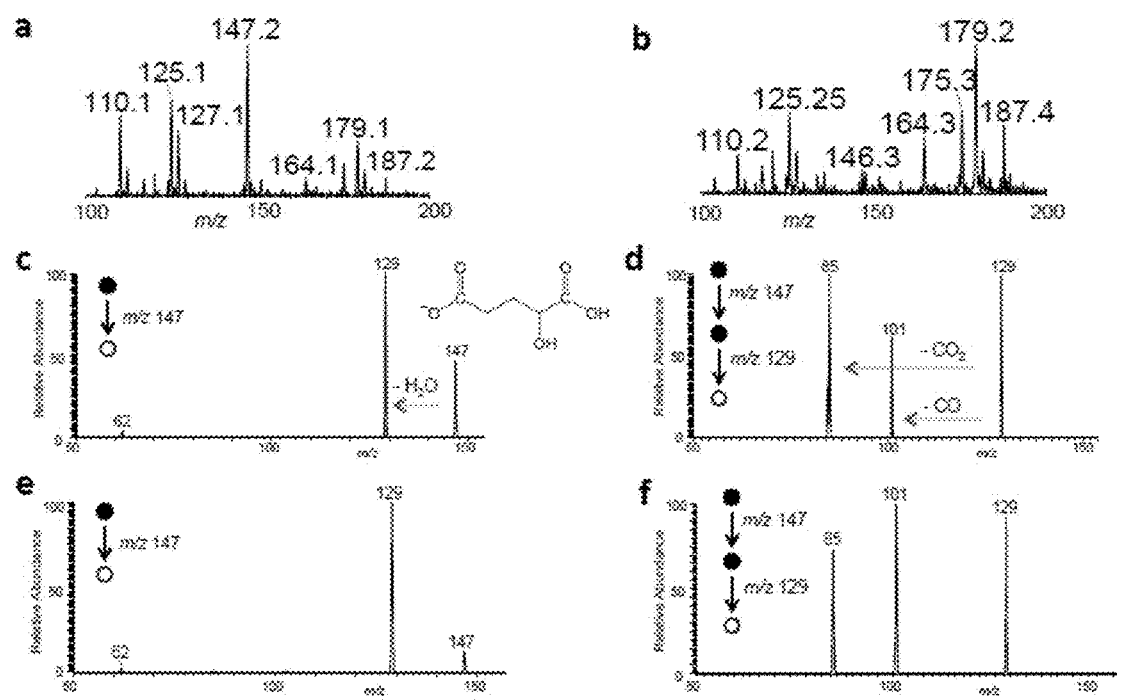
FIG. 30 panels A-F are mass spectra showing detection of 2-HG in gliomas using DESI MS. Negative ion mode DESI mass spectra obtained using a linear ion trap mass spectrometer from m/z 100 to 200 for samples G23, an oligodendroglioma with the IDH1 R132H mutant (FIG. 30 panel A), and G31, a glioblastoma with wild-type IDH1 (FIG. 30 panel B). Tandem mass spectra of m/z 147 detected from sample G42, an oligodendroglioma with the IDH1 R132H mutant ($MS^2$, (FIG. 30 panel C); $MS^3$, (FIG. 30 panel D)) and from a 2-HG standard ($MS^2$, (FIG. 30 panel E); $MS^3$, (FIG. 30 panel F)).

Negative ion mode DESI MS mass spectra of samples G23, and G31 are shown in FIG. 30 panels A-F, using MeOH:H$_2$O (1:1) as the solvent system. Tandem MS analysis was used for identification of the molecules species at m/z 147.2. Further characterization was performed by MS$^3$. The standard compound, L-α-Hydroxyglutaric acid disodium salt was purchased from Sigma-Aldrich Inc., Milwaukee, Wis. and was subjected to tandem MS experiments under the same conditions. Confirmation experiments were performed using a high-resolution LTQ Orbitrap mass spectrometer (Thermo Fisher Scientific, San Jose, Calif., USA). Further analysis was then conducted with the amaZon speed ion trap. For this instrument, the 2-HG signal was located at m/z 146.9 and was assigned using a mouse brain that contained a large tumor with the 2-HG mutation. Tandem MS and MS³ experiments were conducted on this peak to confirm its identity and found to be identical to the fragmentation pattern obtained with the LTQ instrument. Imaging of another mouse brain that had another tumor without the 2-HG mutation did not show this peak.

In total, thirty five human gliomas samples were analyzed including oligodendrogliomas, astrocytomas, and oligoastrocytomas of different grades and varying tumor cell concentrations using both ion trap mass spectrometers. Note that tissue analysis by DESI MS was performed without sample preparation but directly on tissue section. One means by which relative levels of a certain molecule can be calculated is by normalizing its signal to a reference signal or set of signals obtained from the sample. In this example, the total abundance of 2-HG signal at m/z 147 was normalized to the sum of total abundance of the forty most abundant lipid species detected from the glioma samples by DESI MS. As a small contribution of background signal at the same m/z 147 was present in DESI mass spectra, MS² was performed for all samples in order to confirm the presence of 2-HG. This was especially important in some IDH1 mutant samples with low tumor cell concentrations and therefore much lower abundances of 2-HG in DESI mass spectrum. If the MS² fragmentation pattern matched that of authentic 2-HG, the sample was determined to be IDH1 mutated. Discrepancies in the fragmentation pattern or absence of detectable levels of m/z 147 were interpreted as IDH wild-type by MS analysis. Results for DESI MS analysis were obtained using two solvent systems. Note that while the solvent system DMF:ACN (1:1) favored relative abundances of low m/z ions when compared to MeOH:$H_2O$, similar trends in 2-HG were observed for both solvents. Interestingly, the ratio of m/z 147 to the sum of lipid species correlated with the tumor cell concentration determined for the sample by histopathological evaluation of serial tissue section, providing a direct measure of the 2-HG levels in tissue. Most samples that were negative for IDH1 mutation as determined by IHC did not present 2-HG in the DESI MS mass spectra, even if the sample presented high tumor cell concentration, as confirmed by tandem MS analysis (with the exception of two samples as noted in the text).

The analysis was able to determine IDH1 status by DESI MS detection of 2-HG in samples with low tumor cell concentration from full mass spectral data. For these samples, low detectable values of m/z 147 could be initially assumed as an indication of IDH negative mutation. Nevertheless, MS² and MS³ of m/z 147 enabled IDH+ status confirmation for these samples, despite the low tumor cell concentration. DESI MS imaging was performed for a few of the samples analyzed to evaluate the distribution of 2-HG and other diagnostic lipid species compared to tumor cell distribution in tissue.

Genetic Analysis:

Archival surgical specimens were reviewed by a pathologist to select the most appropriate tumor-enriched area for analysis. Total nucleic acid was extracted from FFPE tumor tissue obtained by manual macro-dissection, followed by extraction using a modified FormaPure System (Agencourt Bioscience Corporation, Beverly, Mass.). SNaPshot mutational analysis of a panel of cancer genes that included IDH1 and IDH2, was performed as previously described (Dias-Santagata et al., EMBO Mol Med 2, 146-158 (2010)).

The primers listed below were used for targeted mutation analysis at codon R132 in IDH1 (nucleotide positions c.394 and c.395) and at codons R140 and R172 in IDH2 (nucleotide positions c.418, c.419, c.514 and c.515). PCR primers: IDH1 exon 4,5'-ACGTTGGATGGGCTTGTGAGTG-GATGGGTA-3' (forward; SEQ ID NO: 1) and 5'-ACGT-TGGATGGCAAAATCACATTATTGCCAAC-3' (reverse; SEQ ID NO: 2); IDH2 exon 4a (to probe codon R140), 5'-ACGTTGGATGGCTGCAGTGGGACCACTATT-3' (forward; SEQ ID NO: 3), and 5'-ACGTTGGAT-GTGGGATGTTTTTGCAGATGA-3' (reverse; SEQ ID NO: 4); and IDH2 exon 4b (to probe codon R172), 5'-ACGT-TGGATGAACATCCCACGCCTAGTCC-3' (forward; SEQ ID NO: 5), and 5'-ACGTTGGATGCAGTGGATC-CCCTCTCCAC-3' (reverse; SEQ ID NO: 6).

Extension primers: IDH1.394 extR 5'-GACTGACTG-GACTGACTGACTGACTGACTGGACTGACTGACT-GAGATCCCCATAAGC ATGAC-3' (SEQ ID NO: 7), IDH1.395 extR 5'-TGATCCCCATAAGCATGA-3' (SEQ ID NO: 8), IDH2.418 extR 5'-GACTGACTGACTGACT-GACTGACTGACTGACTGACTGGACTGACTGACT-GACTGCCC CCAGGATGTTCC-3' (SEQ ID NO: 9), IDH2.419 extF 5'-GACTGACTGGACTGACTGACT-GACTGAGTCCCAATGGAACTATCC-3' (SEQ ID NO: 10), IDH2.514 extF 5'-GACTGACTGACTGACTGACT-GACTGACTGGACTGACTGACTGACTGACTGGACT-GAC TGACCCATCACCATTGGC-3' (SEQ ID NO: 11) and IDH2.515 extR 5'-GACTGACTGACTGACTGACTGACT-GACTGACTGACTGGACTGACTGACTGACTGACT GGACTGACTGAGCCATGGGCGTGC-3' (SEQ ID NO: 12).

Identification of 2-Hydroxyglutarate with DESI MS

To determine if 2-hydroxyglutarate (2-HG) could be detected from glioma frozen tissue sections by DESI MS, the negative ion mode mass spectra from two glioma samples was first captured: an oligodendroglioma with mutated IDH1 (encoding the amino acid change R132H) and a glioblastoma with wild-type IDH1. 2-HG is a small organic acid containing two carboxylic acid functional groups in its structure. In the negative ion mode, the deprotonated form of 2-HG was detected at an m/z of 147.03 ($C_5H_7O_5^-$). Together with the rich diagnostic lipid information commonly observed from gliomas by DESI MS in the mass range m/z 100-1000, a significant peak at m/z 147 in an IDH1 mutated sample (FIG. 30A) was detected, but not in an IDH1 wild-type sample (FIG. 30B).

Figure 31:
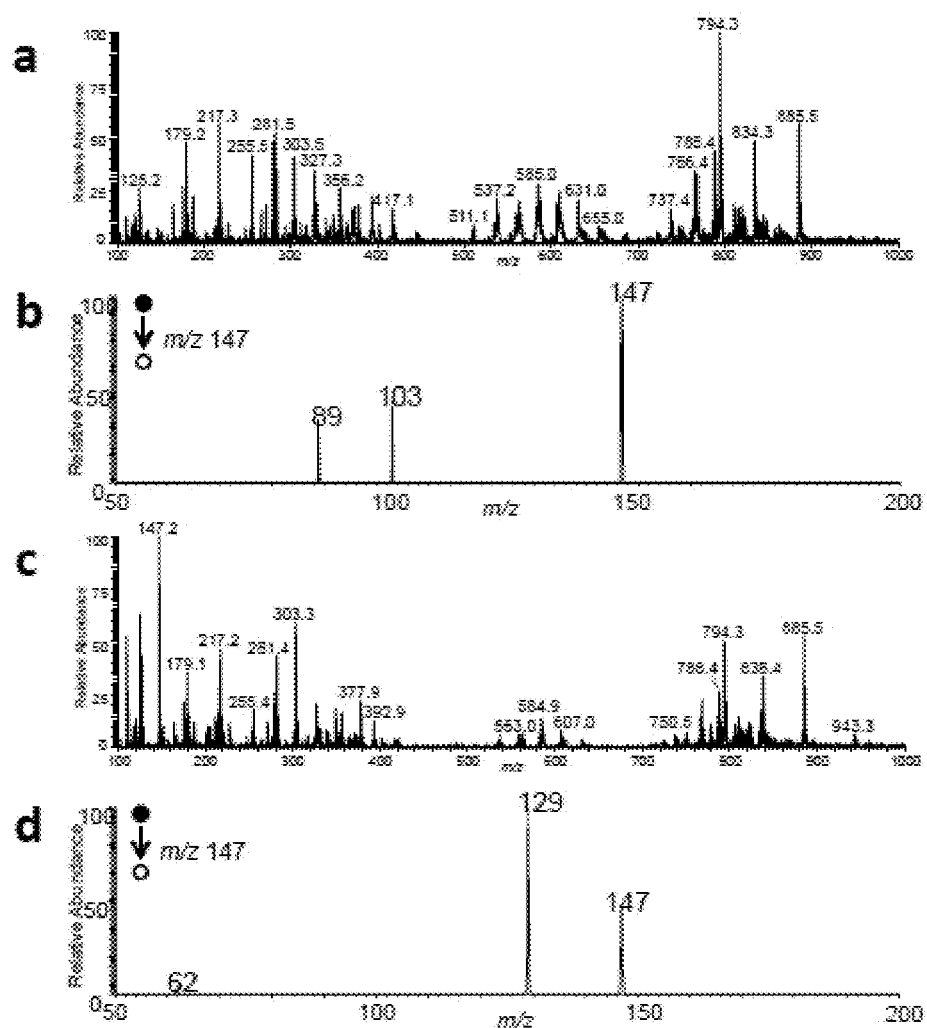
FIG. 31 panel A shows negative ion mode DESI mass spectrum from m/z 100 to 1000 of sample G31, a glioblastoma with wild-type IDH1.
Figure 32:
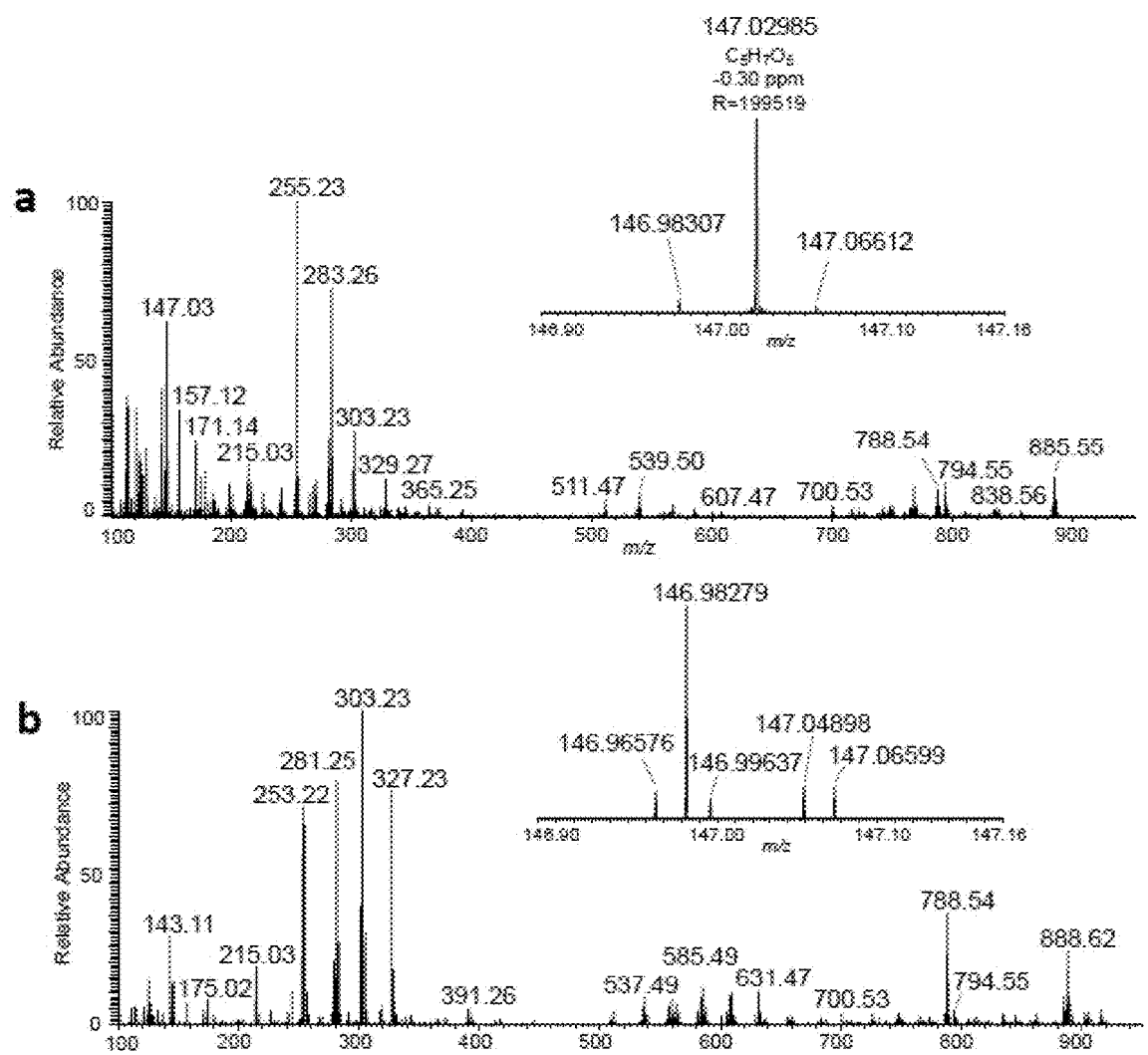
FIG. 32 panel A shows negative ion mode DESI mass spectra obtained in a LTQ Orbitrap mass spectrometer from m/z 100 to 1000 for sample G42, an oligodendroglioma with the IDH1 R132H mutant.

Tandem MS analysis (MS²) with a linear ion trap mass spectrometer was used to characterize the signal at m/z 147 (FIG. 31 panels A-D, FIG. 30 panels C-F). In an oligodendroglioma with the IDH1 R132H mutation, the main fragment ion generated from m/z 147 was m/z 129, which corresponds to a neutral loss of a water molecule from 2-HG (FIG. 30 panel C). Further characterization of m/z 129 with an additional round of tandem MS analysis (MS³) yielded two additional fragment ions at m/z 101 and m/z 85, corresponding to neutral losses of CO and $CO_2$, respectively (FIG. 30 panels D). Identical MS² and MS³ fragmentation patterns were obtained when purified L-α-hydroxyglutaric acid was subjected to tandem MS experiments (FIG. 30 panels E-F). The peaks were further characterized using a high-resolution and high-mass accuracy LTQ Orbitrap mass spectrometer (FIG. 32 panels A-B). DESI mass spectra from an IDH1 R132H mutant sample showed a prominent peak at m/z 147.0298 in the negative ion mode, which matched the molecular formula of the deprotonated form of 2-HG with ($C_5H_7O_5^-$) with a mass accuracy of 0.3 ppm. In all, these results confirm the ability to reliably and rapidly detect 2-HG from human glioma tissue sections with DESI MS.

2-HG Levels Correlate with Mutational Status and Tumor Cell Content

Figure 33:
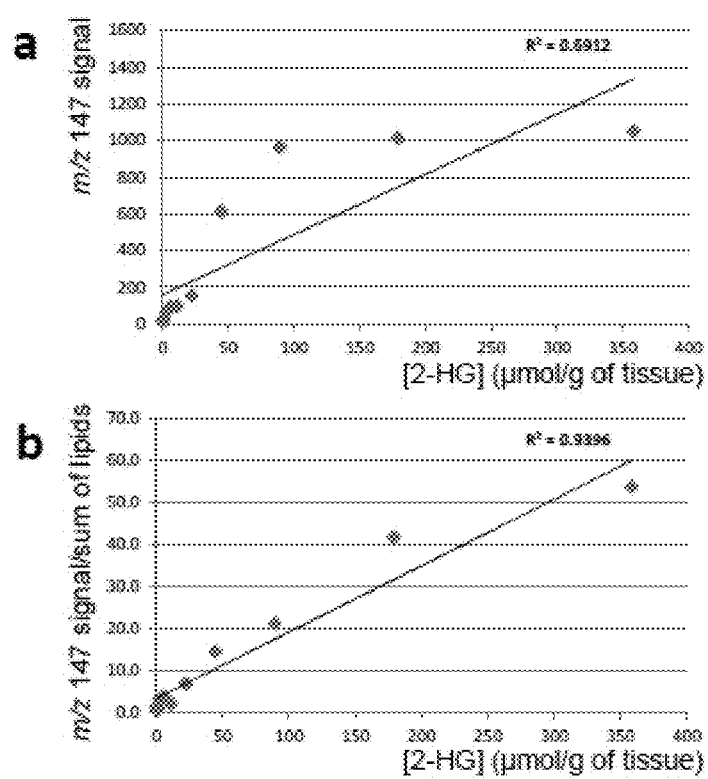
FIG. 33 panels A-B are graphs that show normalization of 2-HG signal and estimation of limit of detection. In DESI-MS analysis, a tissue section of ~12 µm in thickness is examined on a pixel by pixel basis, with sampling area of 200×200 µm2 for each mass spectra acquired. An estimation of the total amount of 2-HG/pixel can be made by first estimating the mass of a 10 mm×6 mm human brain tissue section of 12 µm thickness to be ~0.5 mg. The limit of detection of 2-HG was estimated by depositing different concentrations of standard 2-HG solutions onto mouse brain tissue, followed by DESI MS analysis under the same experimental conditions as for the human glioma samples analysis. Panel A shows a correlation factor of ($R^2$=0.69) was determined when directly plotting the m/z 147 signal versus the known 2-HG concentration, but Panel B shows that a somewhat linear relationship was observed between the m/z 147 normalized to the sum of the forty most abundant lipid species and the known 2-HG concentration ($R^2$=0.94) from the mouse brain tissue by DESI MSI. Note that the correlation in both plots is significantly improved if the concentration range is limited to 100 µmol/g. The limit of detection was estimated to be 3 µmol 2-HG/gram of tissue.

The levels of 2-HG were next monitored using DESI MS in a panel of 35 human glioma specimens (Table 1, above) including primary and recurrent oligodendrogliomas, oligoastrocytomas and astrocytomas of different grades. The samples were first characterized using a clinically validated antibody that selectively recognized the R132H mutant epitope and not the wild-type epitope from IDH127 (Table 1). 21 of the 35 samples had the R132H mutation. 2-HG levels were then measured in these samples using a linear ion trap LTQ DESI directly from frozen tissue sections. A peak at m/z 147 was detected and it was assigned to 2-HG by tandem MS ($MS^2$) analysis, thereby providing strong independent evidence that these samples were mutated for one of the IDH genes. To account for the variability in desorption and ionization efficiency throughout the tissue and between samples, the 2-HG signal was normalized to the combined signal of the forty most abundant lipid species that were detected during each data acquisition (Table 1). In all of the 21 samples with the IDH1 R132H mutation, 2-HG was clearly detected with a limit of detection estimated to be on the order of 3 µmol 2-HG/g of tissue (FIG. 33, panels A-B).

Figure 34:
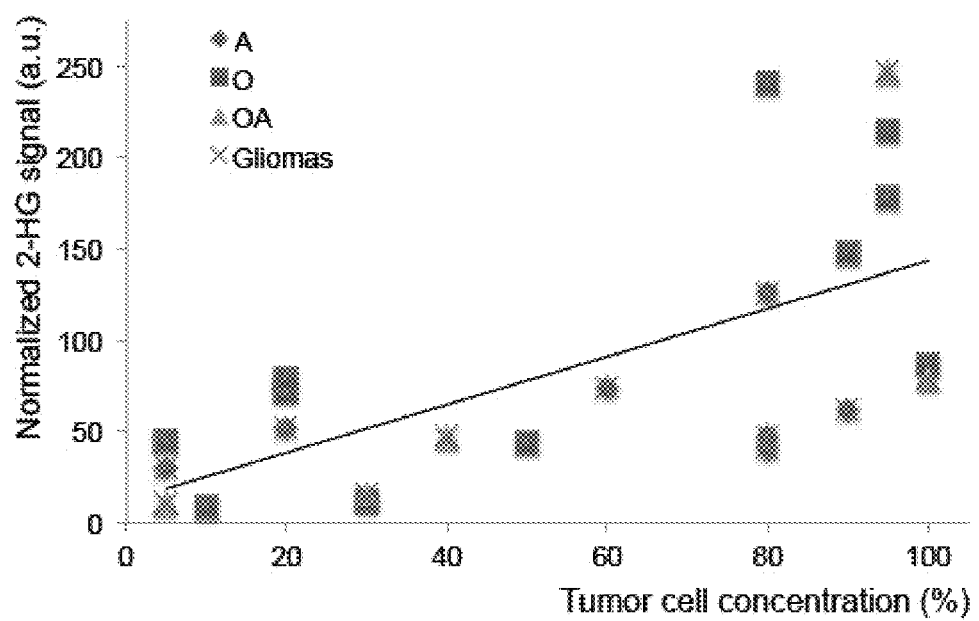
FIG. 34 is a graph of normalized 2-HG signal versus tumor cell concentration in a glioma series with IDH1 mutation (see Table 1 for sample details). All gliomas are represented by an X, oligodendrogliomas are represented by a red square (O), oligoastrocytomas by a green triangle (OA), and astrocytomas by a blue diamond (A). The astrocytoma series is comprised of all glioblastoma except for one astrocytoma grade II (G2) with 60% tumor cell concentration. The correlation factor for the trendline ($R^2$) is 0.42.

Notably, a correlation ($R^2=0.42$) was observed between the concentration of tumor cells and the intensity of the 2-HG signal—samples with low concentrations of tumor cells (<50%) had lower 2-HG levels while samples with high concentrations of tumor cells (>50%) had higher 2-HG levels (FIG. 34). Although the sample set of high concentration tumors is relatively small, it was noted that GBMs with mutant IDH1 generally had lower levels of 2-HG than oligodendrogliomas (FIG. 34).

Figure 35:
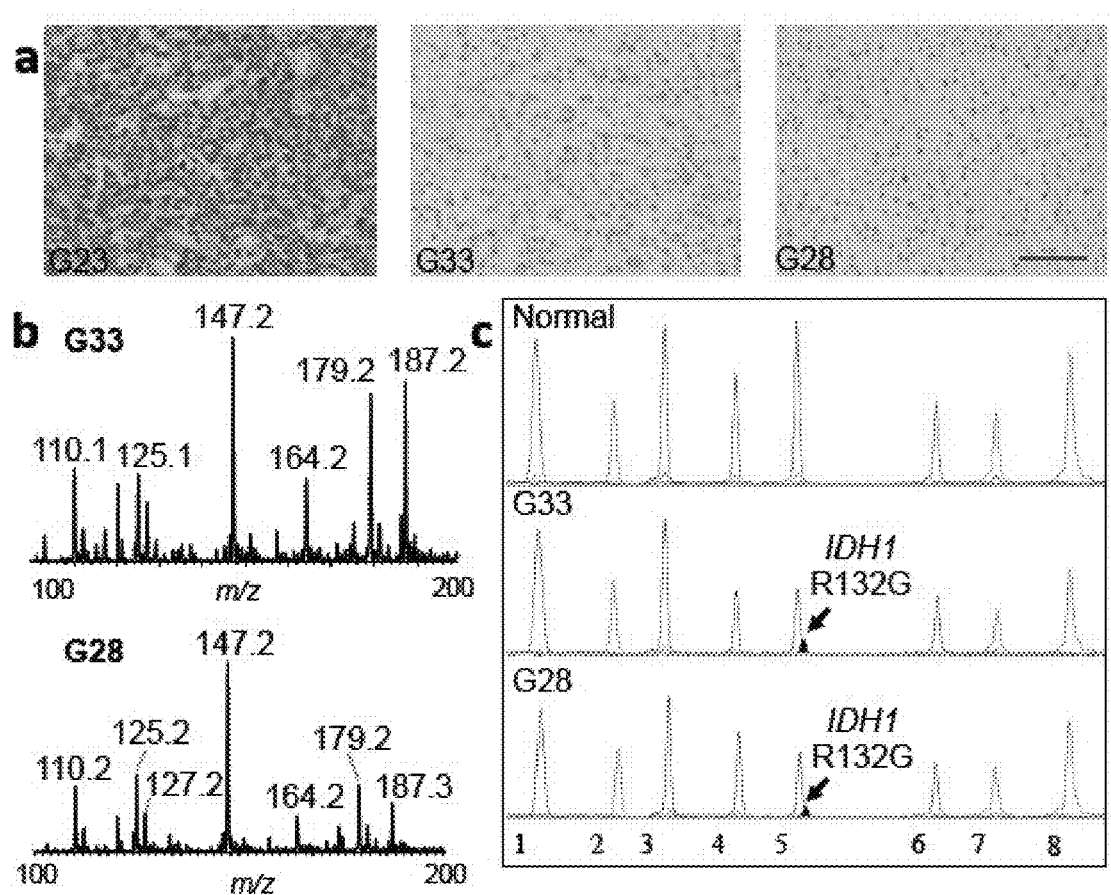
FIG. 35 panels A-C show detecting 2-HG in glioblastoma with IDH1 R132G mutation.

Interestingly, in two of the samples (G28 and G33) that were negative for the IDH1 R132H mutation immunohistochemical staining (FIG. 35 panel A), 2-HG signal was detected (FIG. 35 panel B). The signal from both samples was confirmed to be from 2-HG by tandem MS analysis ($MS^2$). Because other mutations in IDH1 or IDH2 can lead to 2-HG accumulation (Chi et al., J Neurooncol 110, 89-98 (2012); Dias-Santagata et al., PLoS One 6, e17948 (2011); and Hartmann et al., Acta Neuropathol 118, 469-474 (2009)), targeting sequencing (Dias-Santagata et al., EMBO Mol Med 2, 146-158 (2010)) was performed for all of the major mutations in IDH1 and IDH2 that have been described in gliomas (Weller et al., Glia 59, 1200-1204 (2011)). This analysis revealed that both samples G28 and G33 harbored a less common but previously described IDH1 mutation that leads to substitution of amino acid arginine with glycine at position 132 (R132G) (FIG. 35 panel C). These results provide a clear example of how detecting 2-HG with DESI MS allows rapid and accurate determination of IDH1 status in human gliomas. While the diagnostic antibody only recognizes one of the many IDH1 mutants, DESI MS captured the presence of 2-HG independent of the underlying genetic mutation in IDH1. Notably, the data show that DESI MS can detect 2-HG with very high sensitivity and specificity, for example, 2-HG signal were detected in all cases with mutant IDH1 and did not detect 2-HG signal in any of the cases with wild type IDH1.

2D DESI MS Imaging of 2-HG in Glioma Sections Delineates Tumor Margins

To further validate DESI MS as a tool for monitoring 2-HG levels, two-dimensional (2D) DESI MS imaging were turned to for studying the spatial distribution of molecules across a tissue section. DESI MS imaging can be conducted in a manner that does not destroy a sample as it is being analyzed when a histologically compatible solvent system is used, so that the same tissue section can be stained with H&E and the spatial molecular information derived from DESI MS can be overlaid onto the optical image of the tissue. As such, this approach provides a powerful way to correlate 2-HG levels with histopathology.

Figure 36:
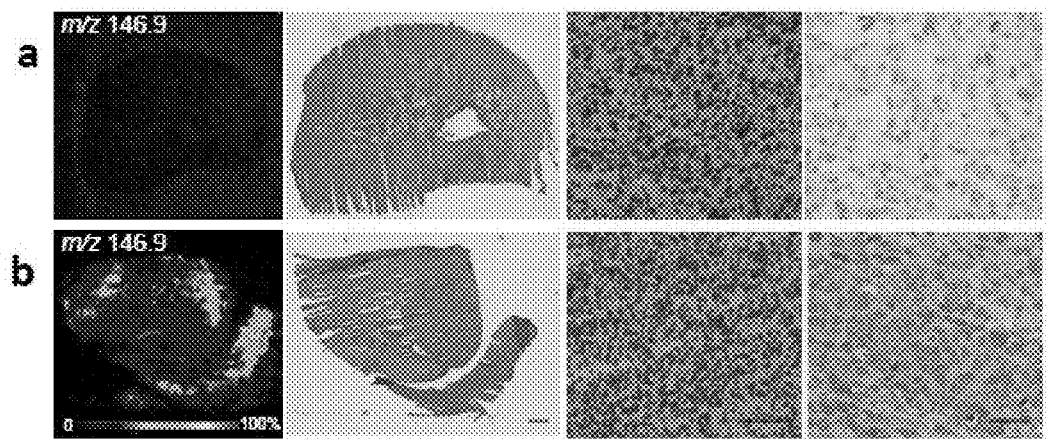
FIG. 36 panels A-B show two-dimensional DESI MS ion images of human glioma cell xenografts in immunocompromised mice.

2D DESI MS data was first acquired from frozen sections of human tumor cell lines that had been implanted into the brains of immunocompromised mice (FIG. 36). A signal for 2-HG was not detected from xenografts of a glioblastoma cell line (BT329) that has wild-type IDH1 (FIG. 36 panel A). Strikingly, however, a strong signal for 2-HG was found throughout the tissue section of the mouse brain that was diffusely infiltrated by a glioblastoma cell line (BT116) that has the IDH1 R132H mutation (FIG. 36 panel B).

Figure 37:
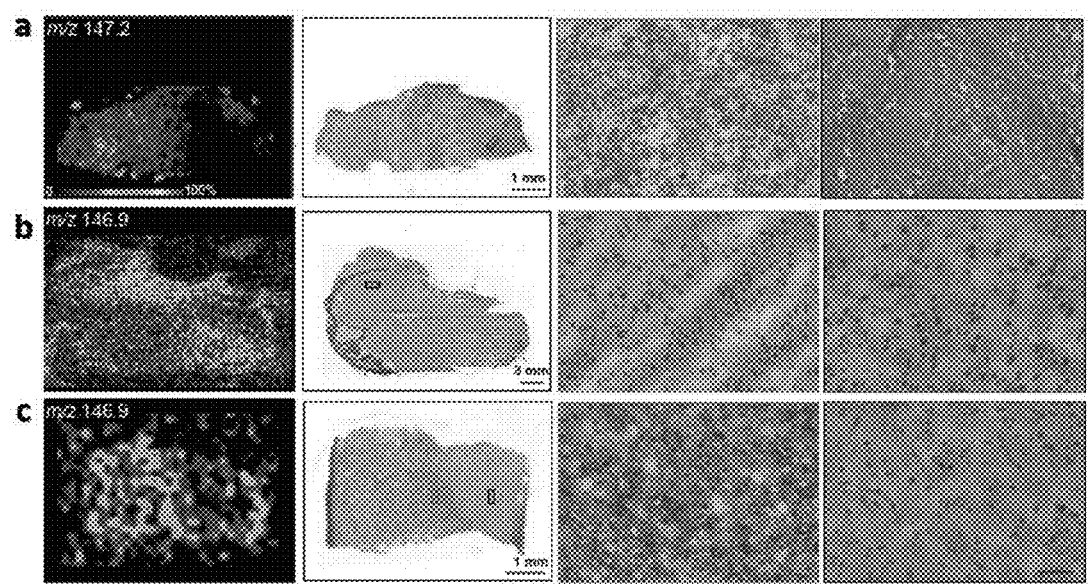
FIG. 37 panels A-C show two-dimensional DESI MS ion images of human glioma resection specimens. The panels show negative ion mode two-dimensional DESI MS images from glioma resection specimens with IDH1 mutations. Panel A shows G30, panel B shows S55, and panel C shows D31. The left panel is an ion map demonstrating the relative signal intensity of peaks at m/z 146.7-147.2, which were each confirmed to be 2-HG by tandem MS analysis (MS2). Mass spectrometry data for sample G30 was acquired using an LTQ Ion Trap (Thermo Fisher Scientific, San Jose, Calif., USA) and for samples S55 and D31 using an amaZon Speed ion trap (Bruker Daltonics, Billerica, Mass., USA). Relative signal intensity (0-100%) is plotted for each specimen using a color scale. Low magnification light microscopy images of HE stained sections show the tissue outline. Red boxed areas indicate regions of higher tumor cell concentration. Black boxed area in panel A indicate blood, and in panels B-C indicate rare infiltrating tumor cells with corresponding high magnifications in the two right most columns. Scale bars as indicated or 100 µm in the panels in the two right most columns.

Tissue sections of human glioma specimens were next turned to that had been surgically resected. Using 2D DESI MS with both an LTQ Ion Trap (Thermo Fisher Scientific, San Jose, Calif., USA) and an amaZon Speed ion trap (Bruker Daltonics, Billerica, Mass., USA), accumulation of 2-HG was observed within a densely cellular glioblastoma with mutated IDH1 (FIG. 37 panel A). 2-HG was absent in an area of hemorrhage abutting the tumor (FIG. 37 panel A). In tissue specimens from two additional glioma resections, areas that contained regions of tumor were identified as well as regions of brain with only scattered infiltrating glioma cells, i.e. the margin on the tumor. DESI MS revealed strong 2-HG signals in the cellular portions of these samples but much weaker signals in the portions of brain with scattered infiltrating tumor cells (FIG. 37 panels B-C). By validating the DESI MS results directly with tissue histopathology, it was show that monitoring 2-HG levels with DESI MS can help to readily discriminate tissue with dense tumor from tissue with only scattered tumor cells. Such discriminatory capacity can help define tumor margins.

3D Mapping of 2-HG onto MRI Tumor Reconstructions

MRI information is critical for planning neurosurgical procedures. During the surgery, neuronavigation systems allow the neurosurgeon to register the position of surgical instruments with pre-operative plans (i.e. confirming where the tools are relative to the imaging findings). Surgeons can therefore digitally mark the site of a biopsy relative to the tumor in the MRI. Two IDH1 mutated gliomas were resected in this manner, using three-dimensional (3D) mapping, marking the positions of multiple biopsies in each case. In both cases, the 2-HG content of each stereotactic specimen was measured and normalized to its lipid signals. This information was then correlated with the tumor cell content of each stereotactic specimen, as determined by review of both H&E and immunostains for IDH1 R132H.

Figure 38:
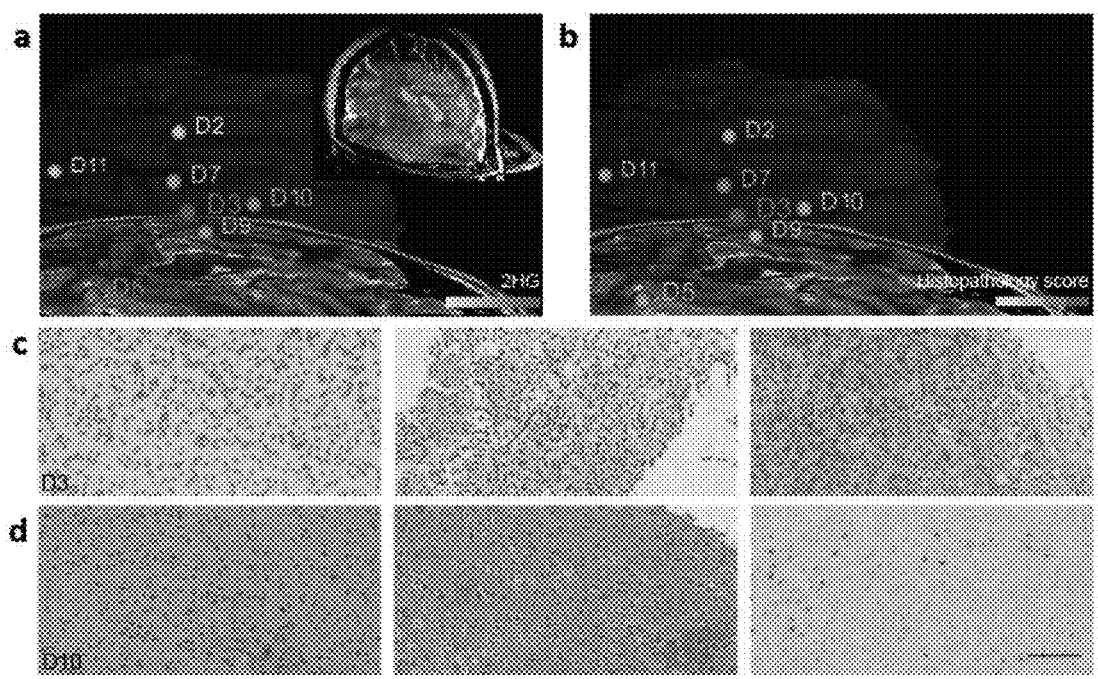
FIG. 38 panels A-D show 3D mapping of 2-HG over MRI volume reconstruction for surgical case 10, an oligodendroglioma grade II.

In the resection of an oligodendroglioma (FIG. 38), strong 2-HG signals were identified in the sample (D3) taken from the center of the tumor mass (FIG. 38 panel A). This sample was comprised of dense tumor (FIG. 38 panels B-C). Biopsies from the margins of the radiographic mass (e.g. D10, FIG. 38 panels B and D) contained low concentrations of infiltrating glioma cells (FIG. 38 panel D). In such samples low levels of 2-HG were detected (FIG. 38 panel D). Consistent with prior findings on a large panel of glioma specimens (FIG. 33 and Table 1), these intraoperative samples demonstrate that the normalized level of 2-HG correlates with the tumor cell concentration and can help define samples that are at the infiltrating border of the tumor.

The second surgical resection was performed (FIG. 39) in the Advanced Multimodality Image Guided Operating (AMIGO) suite at Brigham and Women's Hospital that is a part of the National Center for Image-Guided Therapy. In this advanced surgical and interventional environment, MRI can be performed during the operation to see if additional tumor remains in situ. This residual tumor can then be resected before the procedure is completed.

Figure 39:
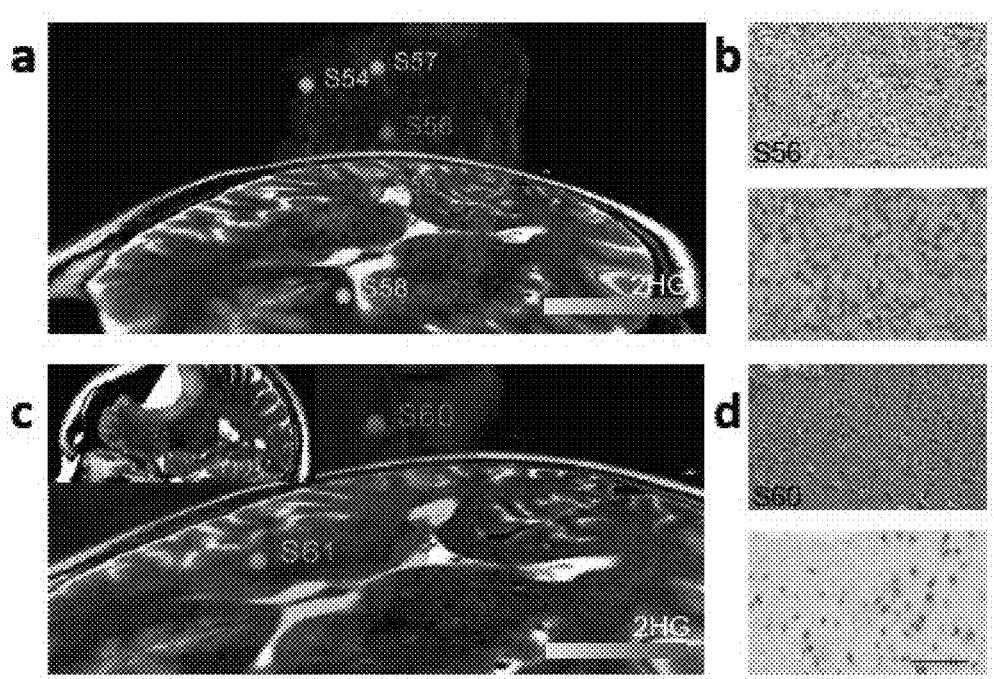
FIG. 39 panels A-D show 3D mapping of 2-HG over MRI volume reconstruction for surgical case 13, an oligoastrocytoma grade II.

An oligoastrocytoma was resected in this second case. Multiple biopsy pieces were mapped and 2-HG levels were measured in each of them (FIG. 39 panel A). The highest levels of 2-HG were detected in specimens that were taken from the center of the tumor mass and that proved to be densely cellular tumor (FIG. 39 panel B). AN MRI of the patient's brain was taken once it appeared that all of the tumor had been removed (i.e. following an apparent gross total resection). The T2 weighted intraoperative image revealed a region that was concerning for residual tumor (FIG. 39 panel C, outlined in green in the inset). Because these areas were close to the premotor cortex, they were carefully sampled to preserve the patient's motor function. Two additional specimens were digitally registered to the intraoperative MR image, samples S60 and S61. An equivocal 2-HG signal was detected from one sample (S61), but robust 2-HG signal was detected from the other (S60) (FIG. 39 panel C). Microscopic review of the HE and IDH1 R132H immunostained sections revealed only scattered tumor cells in sample S61, but numerous tumor cells in sample S60 (FIG. 39 panel D). This clinical example demonstrates a scenario where surveying the resection cavity with DESI MS could identify areas of residual tumor without pausing for intraoperative MRI.

Metabolite Levels Correlated to their Originating Source

Using gliomas with IDH1 mutations as an example, the data show that a single metabolite, that can be monitored during surgery with ambient mass spectrometry (MS) techniques, can rapidly provide highly relevant information: tumor classification (i.e. 2-HG expressing CNS tumors are nearly always gliomas), genotype information (i.e. 2-HG expressing tumors carry mutations in IDH1 or IDH2), and prognostic information (i.e. 2-HG expressing tumors have a more favorable outcome), all with excellent sensitivity and specificity. Unlike more time consuming HPLC-MS approaches that are standardly used for quantifying 2-HG, ambient mass spectrometry techniques enable rapid data acquisition. Because of this, the approach described in this example provides the intraoperative guidance needed to discriminate tumor from normal brain tissue, a distinction that is of utmost importance in neurosurgery.

Because 70-80% of grade II and grade III gliomas as well as the majority of secondary glioblastomas contain IDH1 or IDH2 mutations (Yan et al., N Engl J Med 360, 765-773 (2009)), monitoring 2-HG with intraoperative mass spectrometry (MS) could conceivably become routinely used for surgeries of primary brain tumors, first to classify the tumor and then, if 2-HG is present, to guide optimal resection. The approach described here is applicable for the resection of all 2-HG producing tumors including chondrosarcoma and cholangiocarcinoma.

Other metabolites such as succinate and fumarate, which accumulate in specific tumor types (Linehan et al., Nat Rev Urol 7, 277-285 (2010)), are also valuable metabolite markers for guiding surgery with MS approaches. As metabolomic discovery efforts intensify, the cadre of useful metabolite markers will expand significantly. This will undoubtedly increase the breadth of applications and the diagnostic utility of MS-based approaches that utilize DESI technologies or other ambient ionization methods. Fluidly assessing molecular information, in a rapid timeframe allows surgeons to define tumor margins with molecular cues (i.e. "molecular margins"), enhancing the likelihood of achieving optimal tumor resection.

Additionally, the data show that two-dimensional DESI MS analysis provides adequate spatial resolution without damaging the tissue, which can subsequently be stained with H&E and visualized by standard light microscopy. Because the analyzed tissue remains intact, correlating the amount of metabolite with its originating source (i.e. stroma, blood vessel, tumor or normal non-neoplastic tissue) is achieved These capabilities will allow adjustment of resection during surgery and improve patient outcome. By permitting the integration of molecular and histologic information, DESI MS can now be used to address questions about tumor growth and heterogeneity that are difficult to address with standard tools.

Three-dimensional tumor mapping studies hold similar promise. The information derived with DESI MS, MRI and histology, can be integrated, compared and cross-validated. This rigorous approach helps better understand the clinical and research tools that are used as well as to shed light on tumor growth patterns and pathobiology in situ, for example, directly in the human brain. To date, surgery remains the first and most important treatment modality for patients suffering from brain tumors. The data herein show that metabolite-imaging mass spectrometry is a new tool with broad and powerful clinical and research applications to transform the surgical care of brain and other solid tumors.

What is claimed is:

1. A method for analyzing a tissue section, the method comprising:

depositing the tissue section onto a substrate, wherein the tissue section comprises at least one metabolite indicative of a cancer and a plurality of reference molecules that are not associated with the cancer;

conducting a desorption electrospray ionization (DESI) technique on one or more locations of the tissue section in order to desorb the at least one metabolite and the plurality of reference molecules from the one or more locations of the tissue section and direct the at least one metabolite and the plurality of reference molecules into a mass spectrometer to thereby generate a mass spectral signal of the at least one metabolite and a plurality of reference mass spectral signals at the one or more locations;

normalizing the mass spectral signal of the at least one metabolite at the one or more locations to a combination of the plurality of reference mass spectral signals from the tissue section in order to obtain a relative abundance of the at least one metabolite at the one or more locations within the tissue section; and producing a mass spectral image of the tissue section that comprises a relative abundance of the at least one metabolite at the one or more locations within the tissue section, wherein the relative abundance of the at least one metabolite at the one or more locations within the tissue section is indicative of locations of cancerous tissue or non-neoplastic tissue within the tissue section.

2. The method according to claim 1, wherein the DESI technique uses a solvent that does not destroy native tissue morphology of the tissue section, and wherein the solvent comprises dimethylformamide (DMF), acetonitrile (ACN), tetrahydrofuran (THF) or methanol (MeOH):chloroform (CHCl$_3$).

3. The method according to claim 2, wherein the solvent further comprises at least one of ethanol (EtOH), water (H$_2$O), and acetonitrile (ACN).

4. The method according to claim 2, further comprising performing a histochemistry analysis technique on the tissue sample.

5. The method according to claim 4, wherein the histochemistry analysis technique is H&E staining or immunohistochemistry.

6. The method according to claim 4, further comprising producing an optical image of the tissue section based on data from the histochemistry analysis technique.

7. The method according to claim 6, further comprising overlaying the mass spectral image of the tissue section onto the optical image of the tissue section.

8. The method according to claim 1, wherein the solvent is selected from the group consisting of: acetonitrile (ACN): ethanol (EtOH); and acetonitrile (ACN):chloroform ($CHCl_3$).

9. The method according to claim 1, wherein the plurality of reference molecules are lipids.

10. The method according to claim 1, wherein the DESI technique is performed without prior sample preparation.

11. The method according to claim 1, wherein the tissue section is from a frozen tissue sample.

12. The method according to claim 1, wherein the tissue section is a human tissue section.

13. The method according to claim 12, wherein the human tissue section is a distribution of cells and extracellular matrix that is spread on the substrate.

14. The method according to claim 12, wherein the human tissue section comprises at least a portion of a tumor.

15. The method according to claim 14, further comprising defining one or more tumor margins based on the mass spectral image of the tissue section.

16. The method according to claim 1, wherein the DESI technique is performed in a negative ion mode.

* * * * *